(12) United States Patent
May et al.

(10) Patent No.: US 11,542,136 B1
(45) Date of Patent: Jan. 3, 2023

(54) DISPENSER ACTUATOR ASSEMBLY

(71) Applicant: James Alexander Corporation, Blairstown, NJ (US)

(72) Inventors: Richard James May, Saylorsburg, PA (US); David Robinson, Newton, NJ (US); Jeffrey Rendano, Kunkletown, PA (US)

(73) Assignee: James Alexander Corporation, Blairstown, NJ (US)

( * ) Notice: Subject to any disclaimer, the term of this patent is extended or adjusted under 35 U.S.C. 154(b) by 576 days.

(21) Appl. No.: 16/598,928

(22) Filed: Oct. 10, 2019

Related U.S. Application Data

(60) Provisional application No. 62/744,460, filed on Oct. 11, 2018.

(51) Int. Cl.
*B67B 7/92* (2006.01)
*A61J 1/06* (2006.01)
(Continued)

(52) U.S. Cl.
CPC .................. *B67B 7/92* (2013.01); *A61J 1/065* (2013.01); *A61J 1/16* (2013.01); *A61J 1/2003* (2015.05); *B65D 75/36* (2013.01); *A61M 35/003* (2013.01)

(58) Field of Classification Search
CPC ...... B65B 7/92; A61J 1/065; A61J 1/16; A61J 1/2003; A61M 35/006; A61M 35/003; B65D 75/36
(Continued)

(56) References Cited

U.S. PATENT DOCUMENTS 3,450,319 A 6/1969 Ray et al.
4,784,506 A * 11/1988 Koreska .............. A61M 35/006
401/133

(Continued)

*Primary Examiner* — Ariana Zimbouski
(74) *Attorney, Agent, or Firm* — Paul J. Nykaza; Schacht Law Office, Inc.

(57) ABSTRACT

A dispenser actuator assembly (100) for actuating a dispenser (10) is disclosed. The dispenser (10) is in the form of a glass ampoule assembly (10) having a rupturable glass ampoule (12) containing a flowable material (M). The glass ampoule (12) is contained within an outer container (14) wherein the outer container (14) has a first open end (22) and a second closed end (24). The glass ampoule assembly (10) has an applicator (16) positioned in the first open end (22). The dispenser actuator assembly (100) has a base member (102) configured to mount on the outer container (14). The dispenser actuator assembly (100) also has an actuator assembly (104) operably connected to the base member (102) wherein the actuator assembly (104) has a first actuator arm (132a) and a second actuator arm (132b) each pivotally connected to the base member (102). The first actuator arm (132a) and the second actuator arm (132b) extend from the base member (102) in generally opposed relation defining a first position, or neutral position. The first actuator arm (132a) has a first protrusion (150a) depending therefrom and the second actuator arm (132b) has a second protrusion (150b) depending therefrom. The first actuator arm (132a) and the second actuator arm (132b) are pivotable from the first position towards one another to a second position, or actuating position, that is configured such that the first protrusion (150a) engages the outer container (14) and the second protrusion (150b) engages the outer container (14) to crush the glass ampoule (12) wherein the flowable material (M) is configured to be dispensed from the glass ampoule assembly (10).

14 Claims, 33 Drawing Sheets

(51) Int. Cl.
*A61J 1/20* (2006.01)
*A61J 1/16* (2006.01)
*B65D 75/36* (2006.01)
*A61M 35/00* (2006.01)

(58) Field of Classification Search
USPC .................................... 604/3; 401/132, 133
See application file for complete search history.

(56) References Cited

U.S. PATENT DOCUMENTS

| | | | |
|---|---|---|---|
| 5,538,353 A | 7/1996 | DeHavilland | |
| D386,849 S | 11/1997 | DeHavilland | |
| 5,772,346 A | 6/1998 | Edwards | |
| 6,283,933 B1 | 9/2001 | D'Alessio et al. | |
| 6,315,165 B1 | 11/2001 | Regan | |
| 6,536,975 B1 | 3/2003 | Tufts | |
| 6,539,975 B2 | 4/2003 | Hedenberg | |
| 6,641,319 B2 | 11/2003 | May | |
| 6,729,786 B1 | 5/2004 | Tufts et al. | |
| 6,755,586 B1 * | 6/2004 | Frazier | B05C 17/002 401/133 |
| 6,991,393 B2 | 1/2006 | Tufts et al. | |
| 6,991,394 B2 | 1/2006 | Tufts et al. | |
| 7,182,536 B2 | 2/2007 | Tufts et al. | |
| 7,241,065 B2 | 7/2007 | Tufts et al. | |
| 7,306,390 B2 | 12/2007 | Quintero et al. | |
| 7,422,388 B2 | 9/2008 | Tufts et al. | |
| 7,516,872 B2 | 4/2009 | Boone et al. | |
| 7,581,899 B2 | 9/2009 | May et al. | |
| 7,824,122 B2 | 11/2010 | Flores et al. | |
| 7,909,808 B2 | 3/2011 | Stenton | |
| 7,976,234 B2 | 7/2011 | May | |
| 7,993,066 B2 | 8/2011 | Flores et al. | |
| D651,339 S | 12/2011 | Kirk, III et al. | |
| 8,323,260 B2 | 12/2012 | Stenton | |
| 8,342,765 B2 | 1/2013 | Stenton | |
| 8,403,178 B2 | 3/2013 | May et al. | |
| 8,491,212 B2 | 7/2013 | Castel et al. | |
| 8,518,076 B2 | 8/2013 | Stenton | |
| 8,702,751 B2 | 4/2014 | Stenton | |
| 8,794,858 B2 | 8/2014 | Kirk, III et al. | |
| 8,801,312 B2 | 8/2014 | Guzman et al. | |
| 8,807,859 B2 | 8/2014 | Stenton | |
| 8,864,399 B2 | 10/2014 | Guzman et al. | |
| 9,089,870 B2 | 7/2015 | Frazier | |
| 9,119,946 B2 | 9/2015 | Dokken et al. | |
| 9,265,923 B2 | 2/2016 | Boone et al. | |
| 9,486,829 B2 | 11/2016 | Kirk, III et al. | |
| 9,675,787 B2 | 6/2017 | Guzman | |
| 10,392,163 B2 | 8/2019 | May et al. | |
| 10,518,930 B2 | 12/2019 | May et al. | |
| 10,526,110 B2 | 1/2020 | May et al. | |
| 10,543,956 B2 | 1/2020 | May et al. | |
| 10,603,019 B2 | 3/2020 | Miller et al. | |
| 10,669,065 B2 | 6/2020 | May et al. | |
| 10,689,152 B2 | 6/2020 | May et al. | |
| 10,814,114 B2 * | 10/2020 | Boyajian | A61J 1/2089 |
| 11,241,709 B1 * | 2/2022 | May | A61M 35/006 |
| 11,247,837 B1 * | 2/2022 | May | B65D 83/0055 |
| 2003/0068189 A1 | 4/2003 | Tsaur | |
| 2004/0254561 A1 | 12/2004 | Stenton | |
| 2005/0111900 A1 | 5/2005 | Fazzolari et al. | |
| 2008/0046004 A1 * | 2/2008 | Stenton | A61M 35/003 606/214 |
| 2008/0167681 A1 | 7/2008 | Stenton | |
| 2008/0195040 A1 | 8/2008 | Clark et al. | |
| 2009/0311030 A1 | 12/2009 | Stenton | |
| 2011/0290688 A1 * | 12/2011 | Marcinkowski | B65D 77/26 53/471 |
| 2013/0004230 A1 | 1/2013 | Kirk, III et al. | |
| 2014/0133895 A1 | 5/2014 | Dockery | |
| 2015/0306362 A1 | 10/2015 | Battaglia | |
| 2017/0049210 A1 | 2/2017 | Kirk, III et al. | |
| 2017/0143893 A1 * | 5/2017 | Hasumi | A61M 5/002 |
| 2017/0354406 A1 | 12/2017 | Miller et al. | |
| 2018/0015217 A1 * | 1/2018 | Hasumi | B65D 75/366 |
| 2018/0050858 A1 | 2/2018 | May et al. | |
| 2018/0065776 A1 | 3/2018 | May et al. | |
| 2018/0065783 A1 | 3/2018 | May et al. | |

* cited by examiner

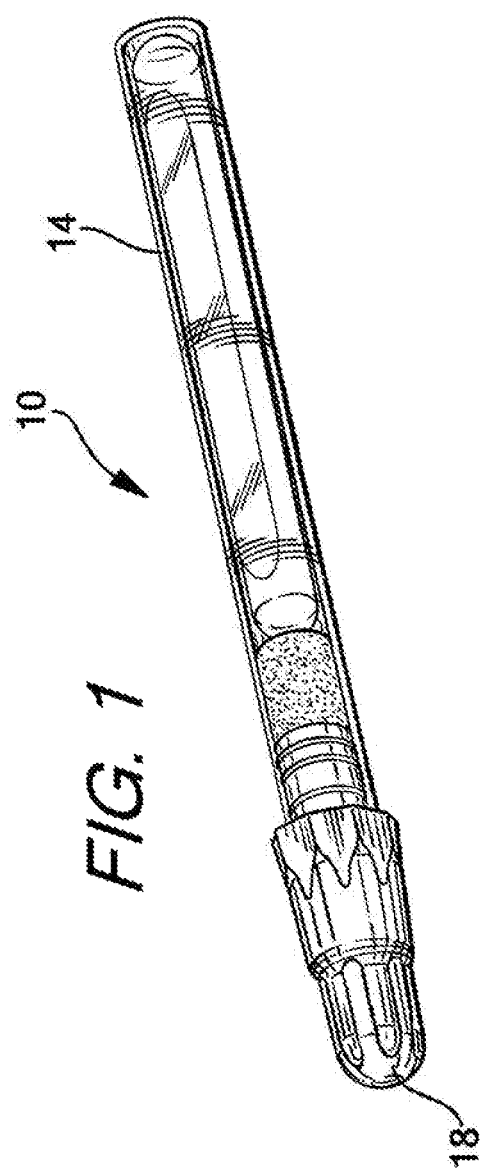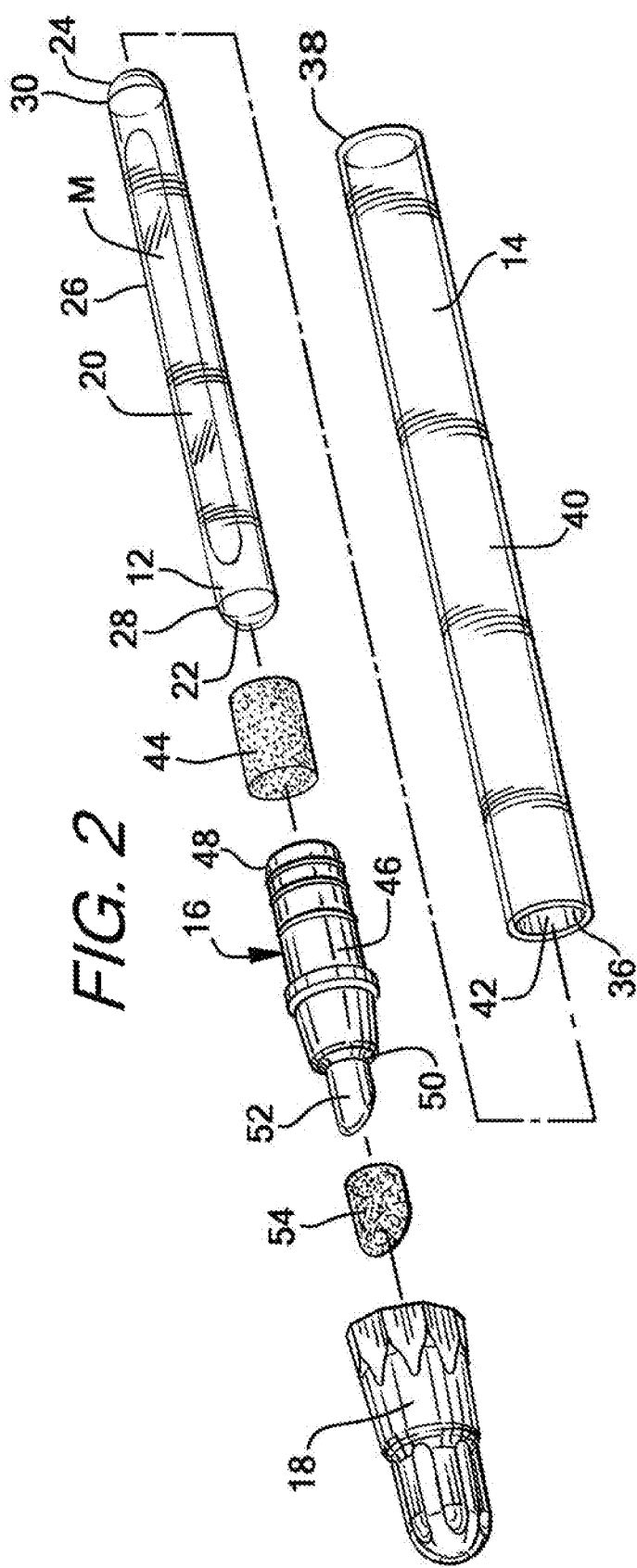

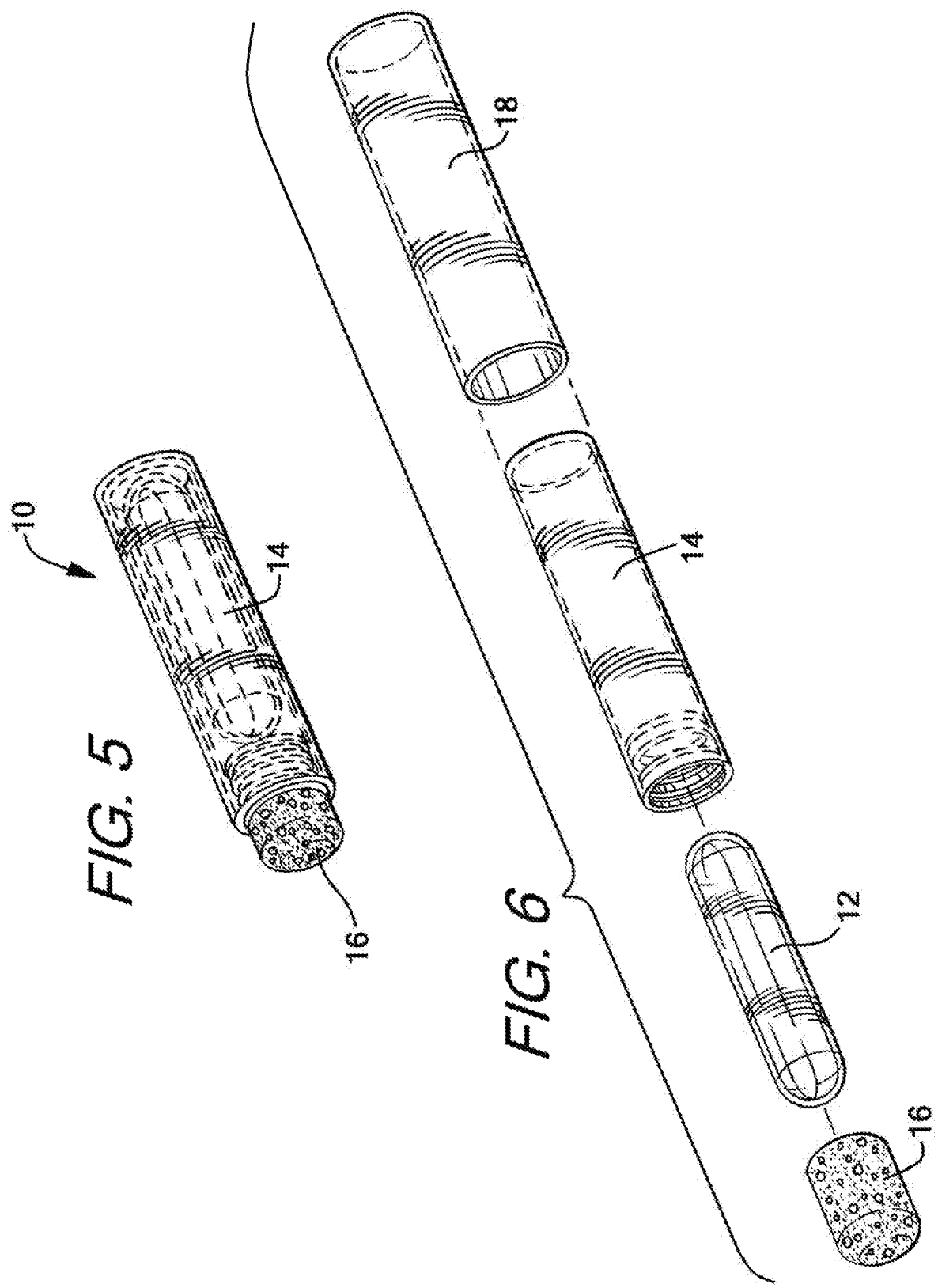

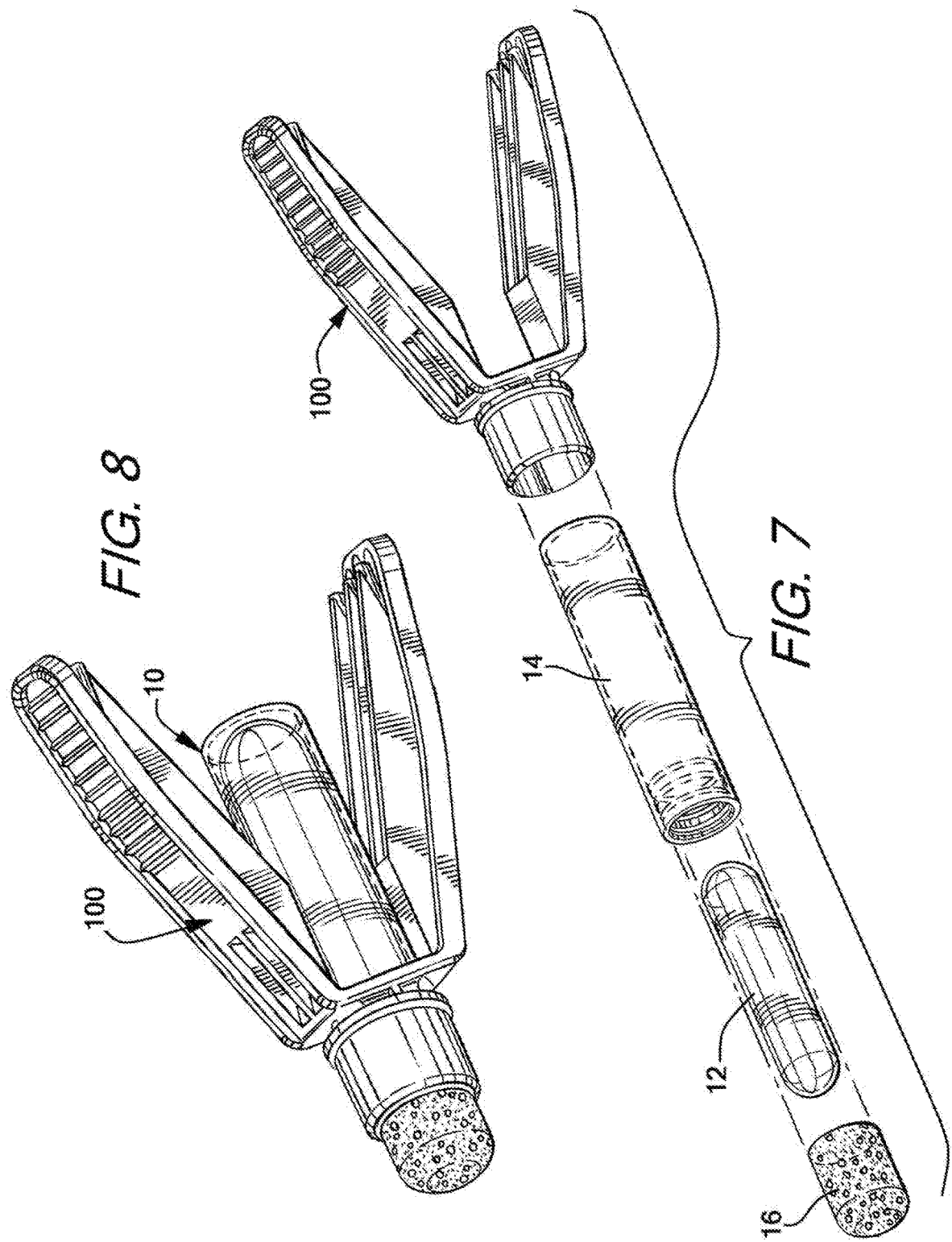

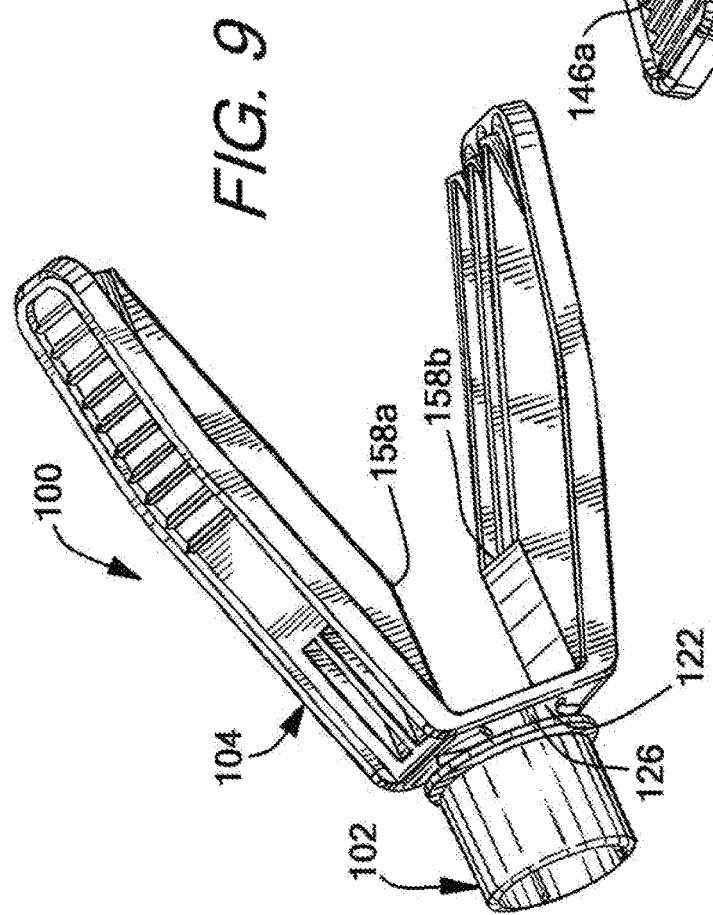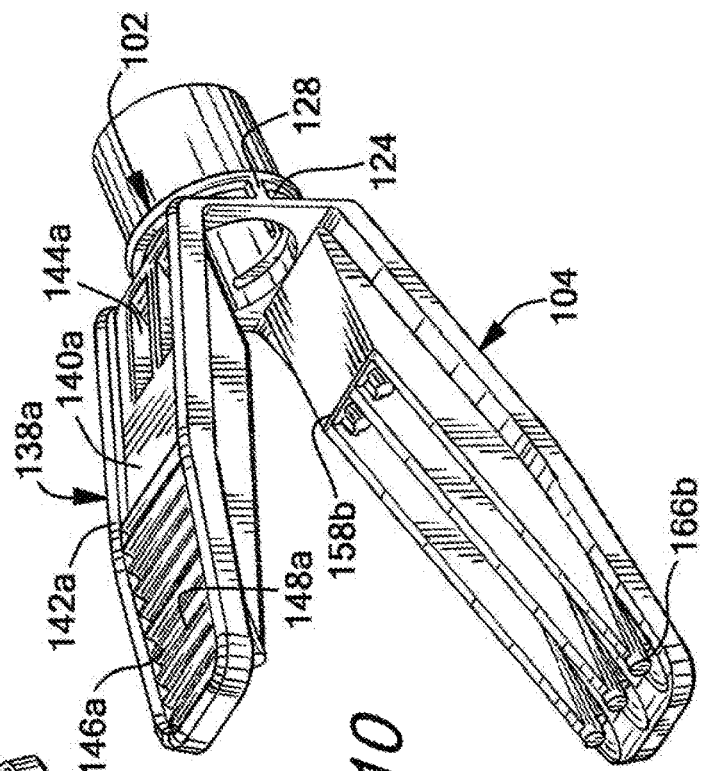

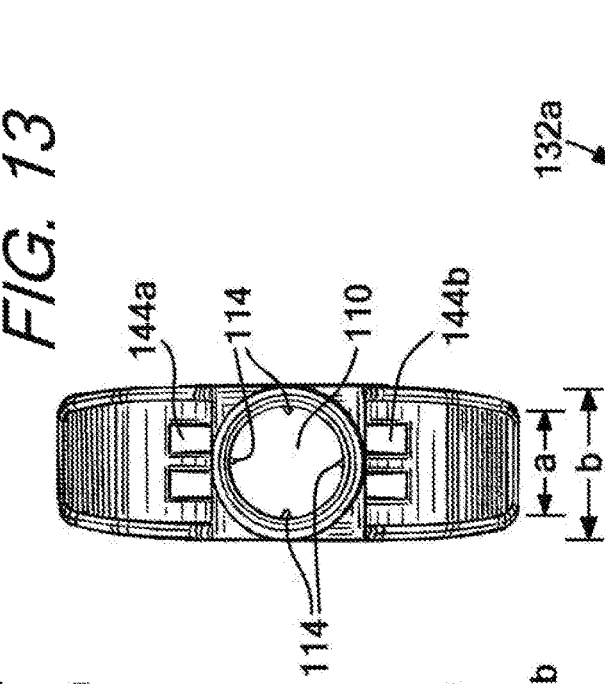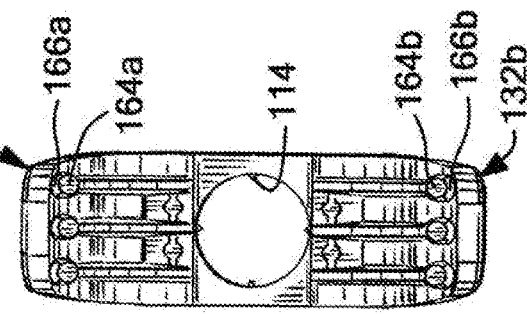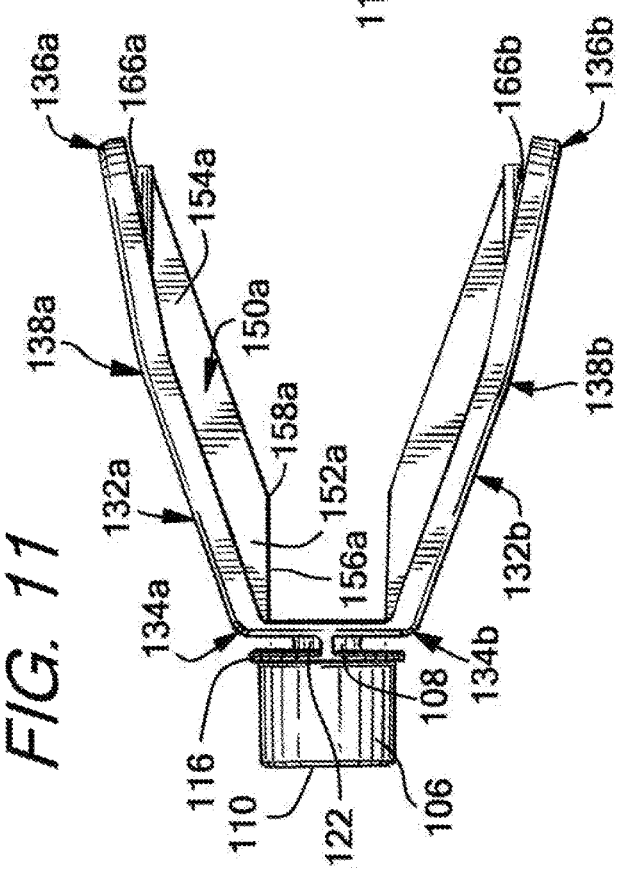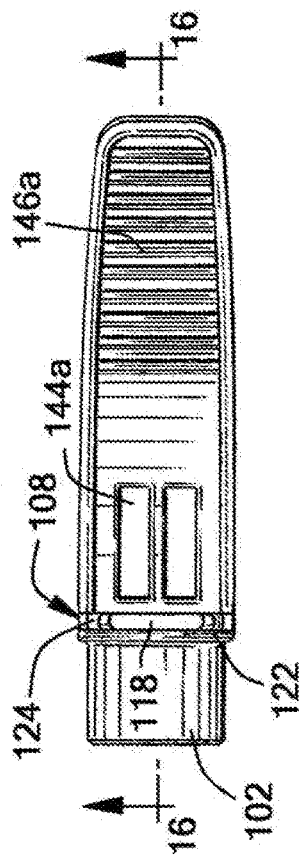

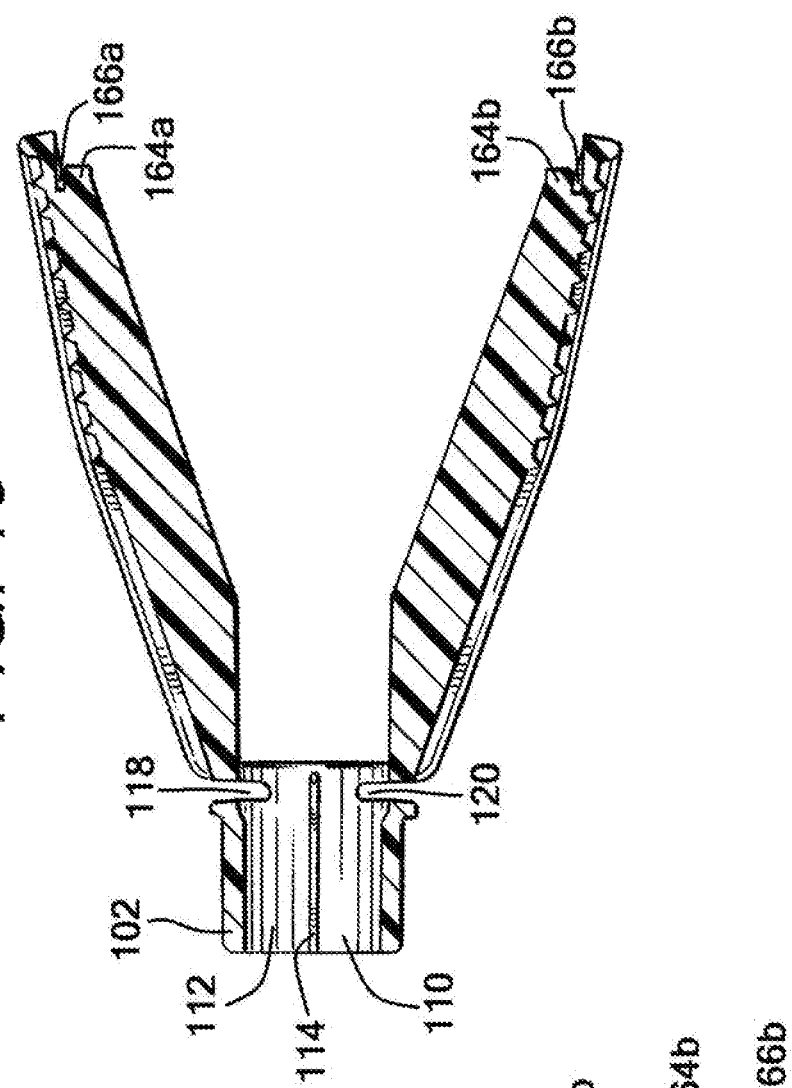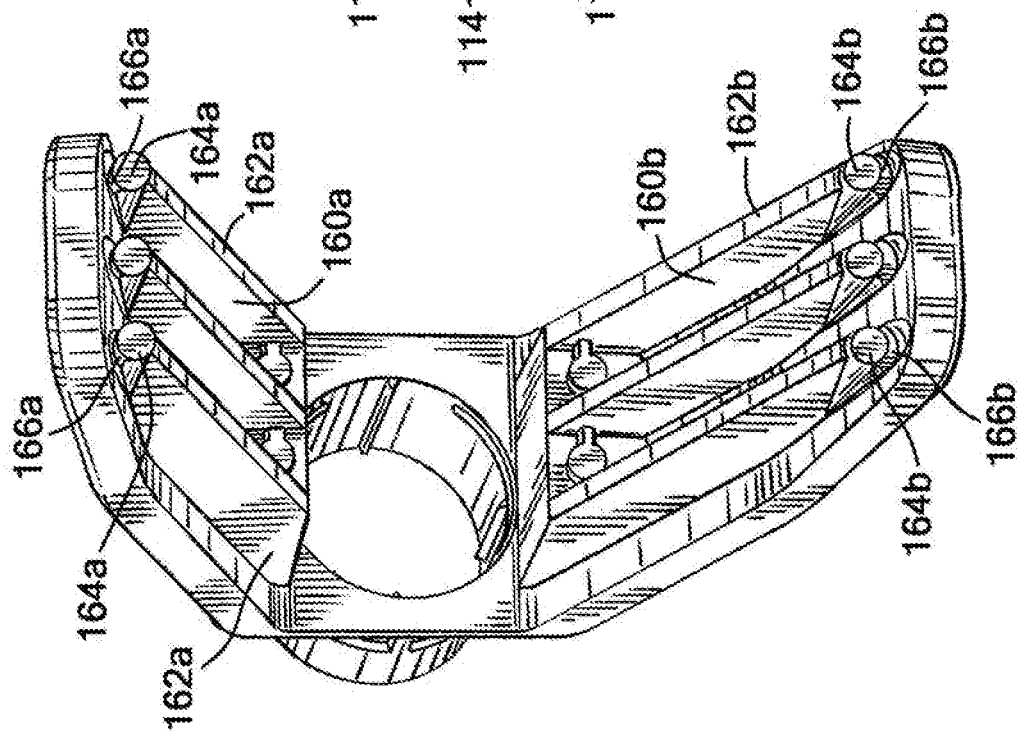

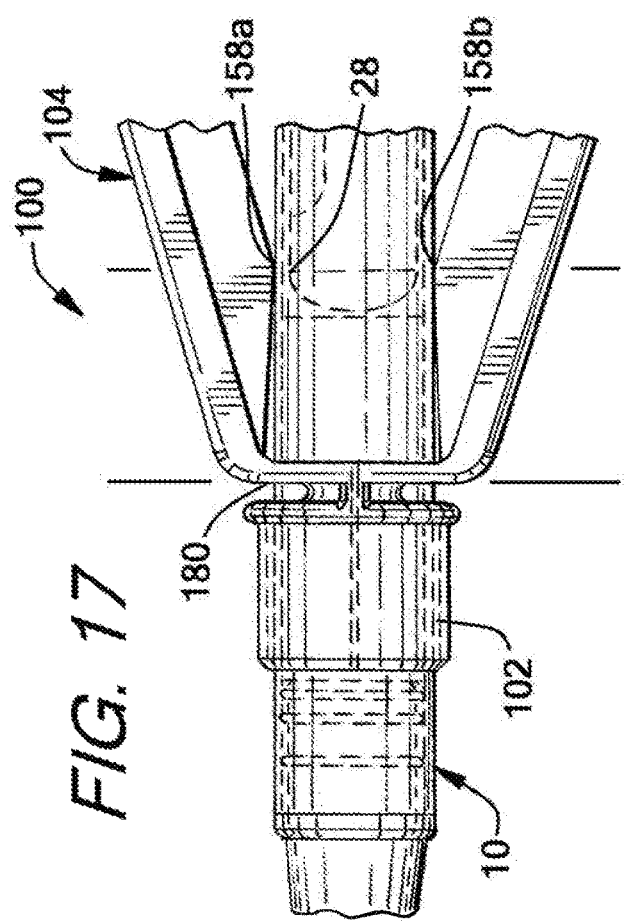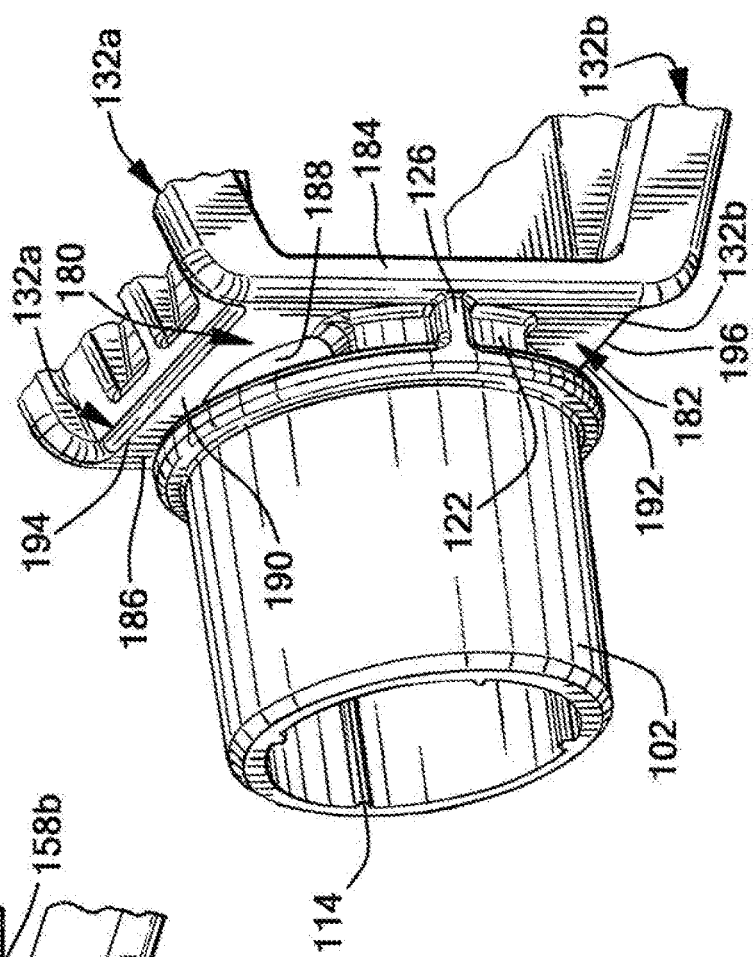

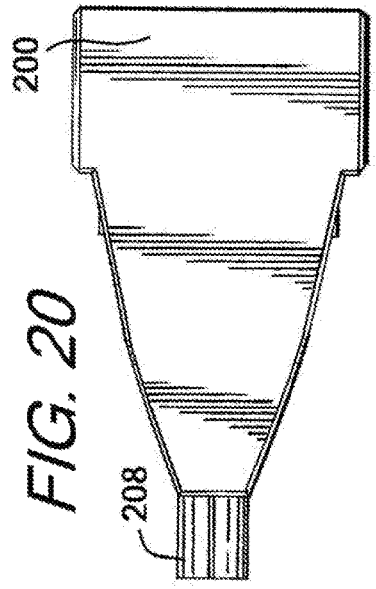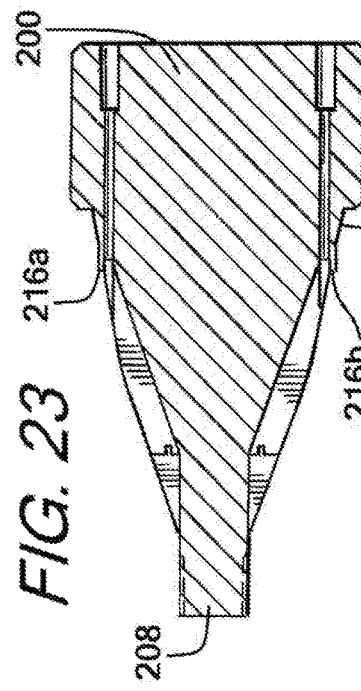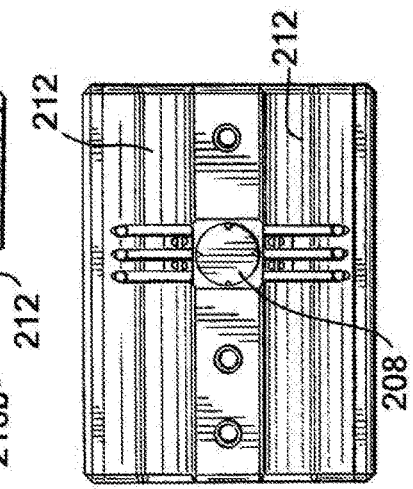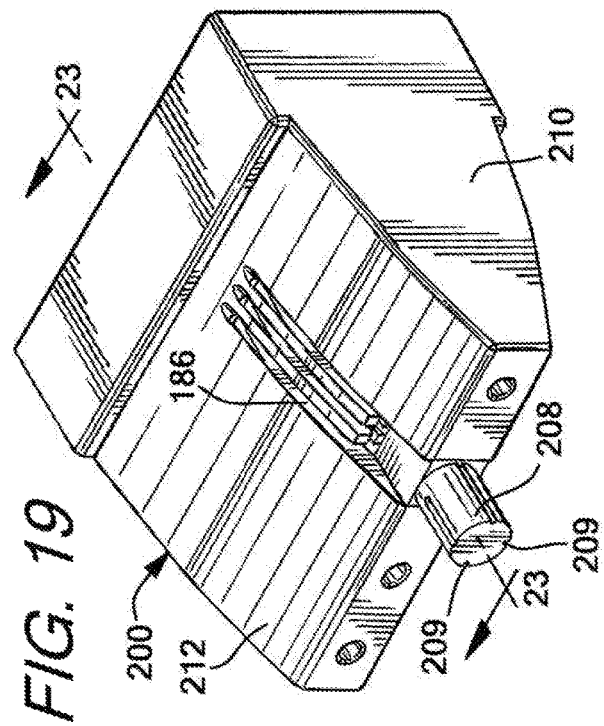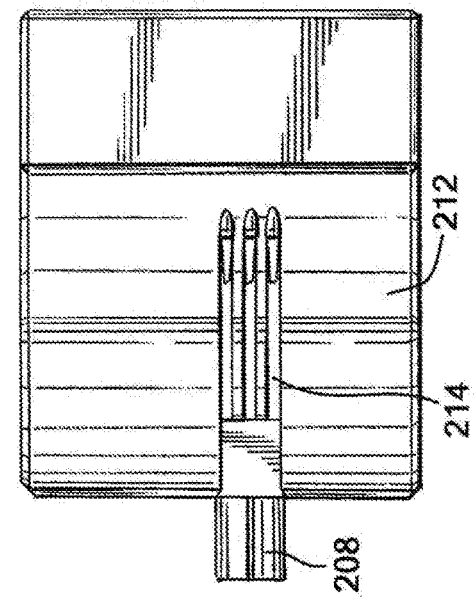

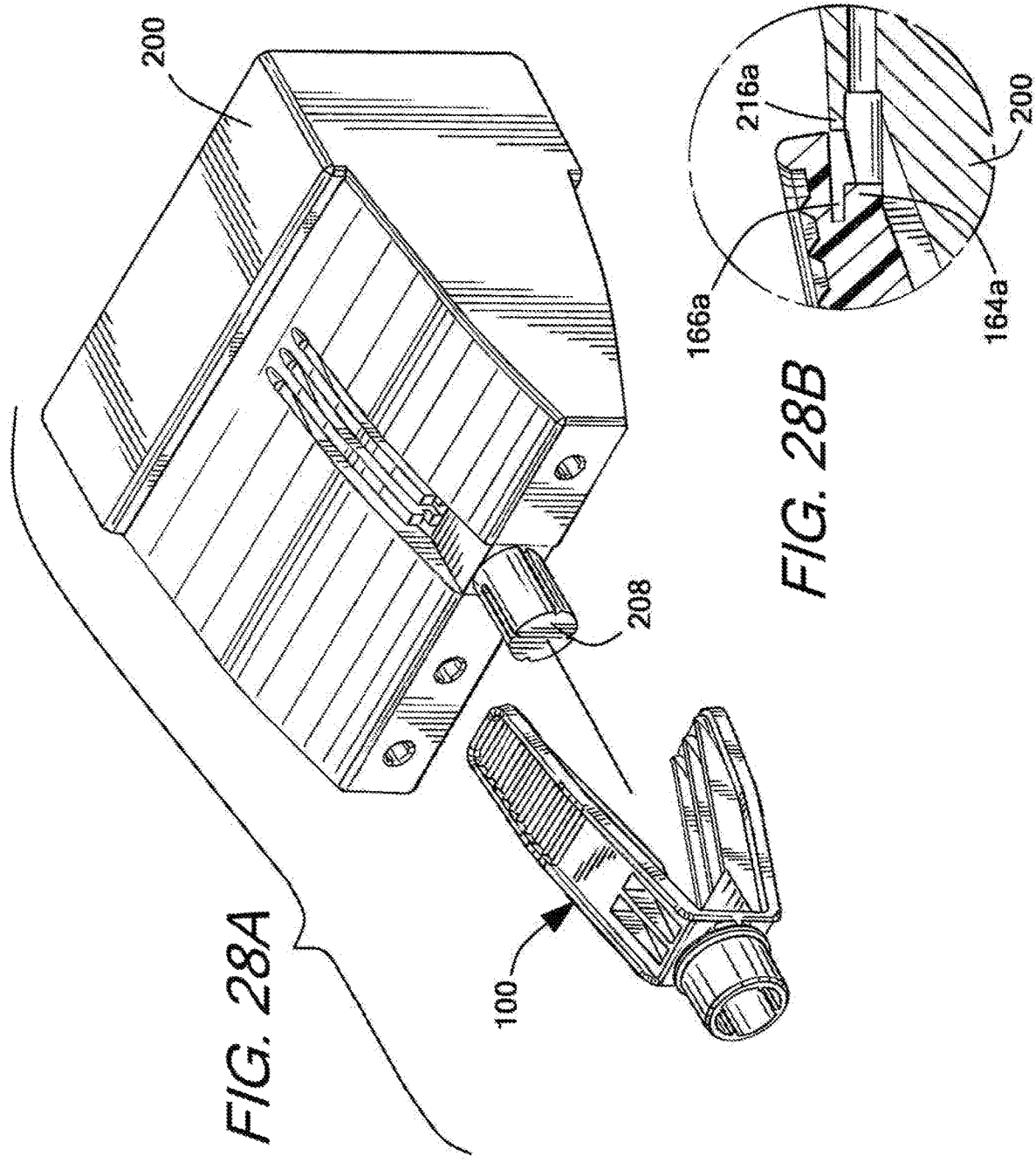

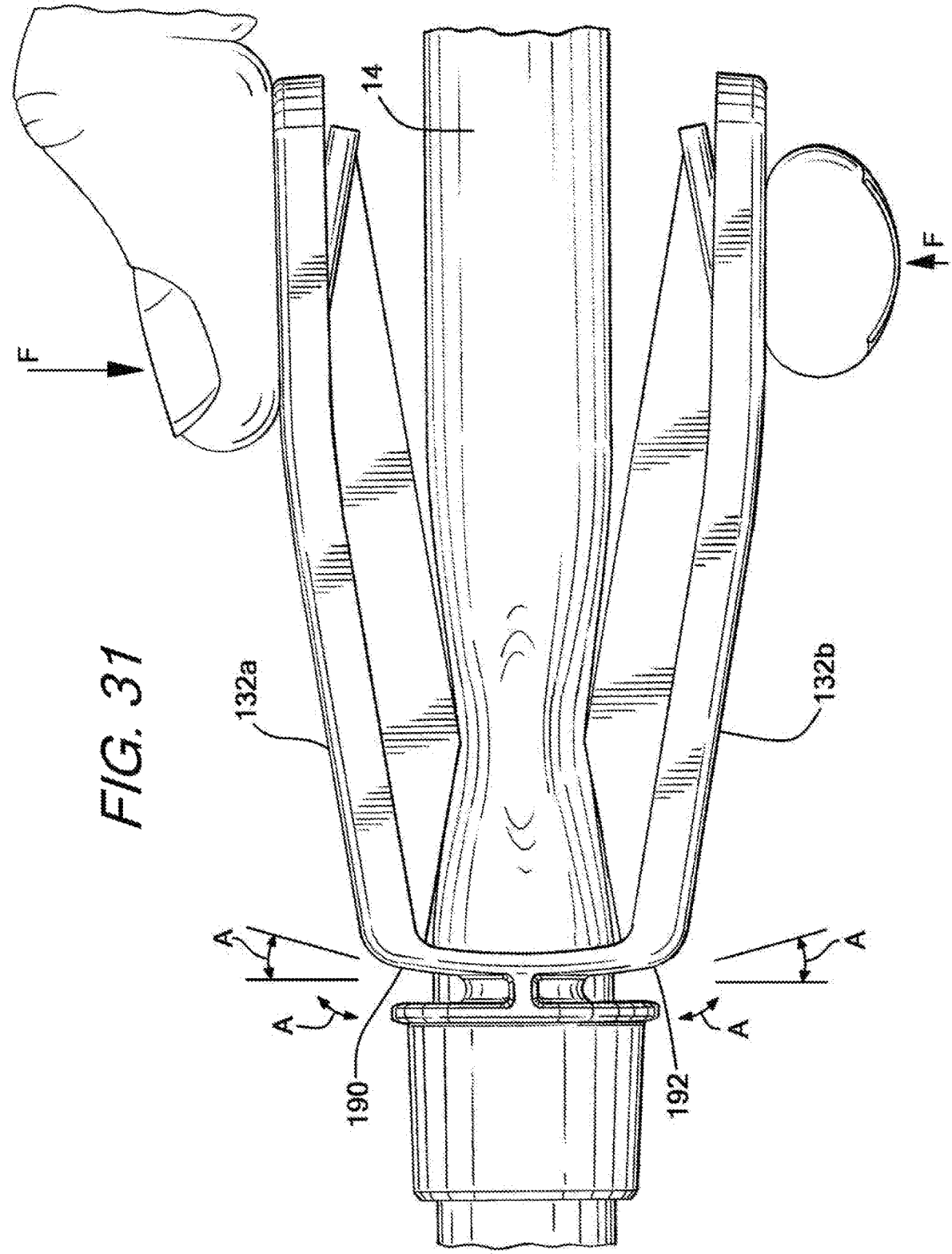

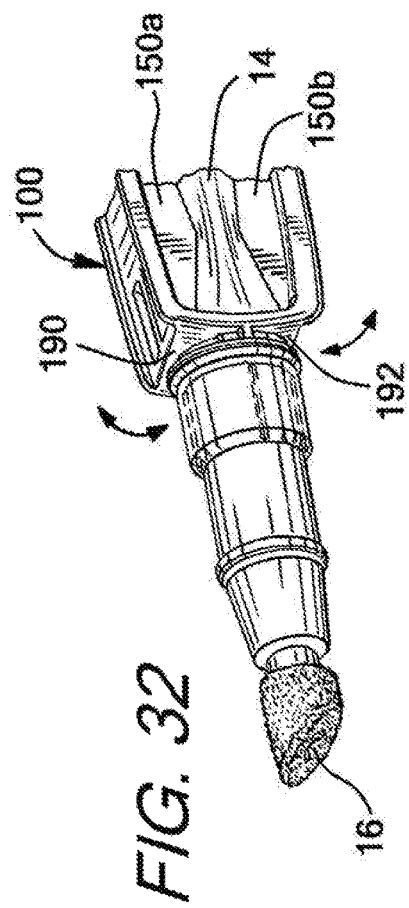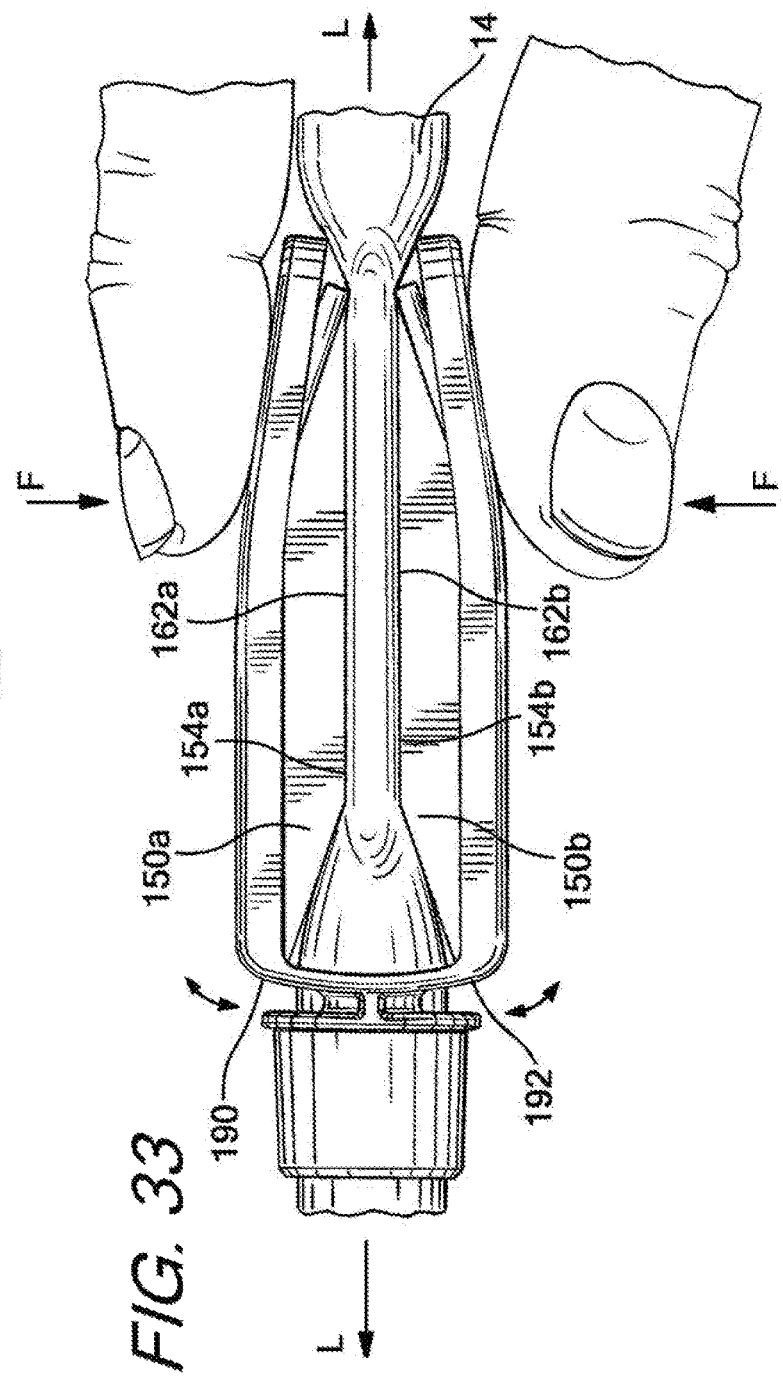

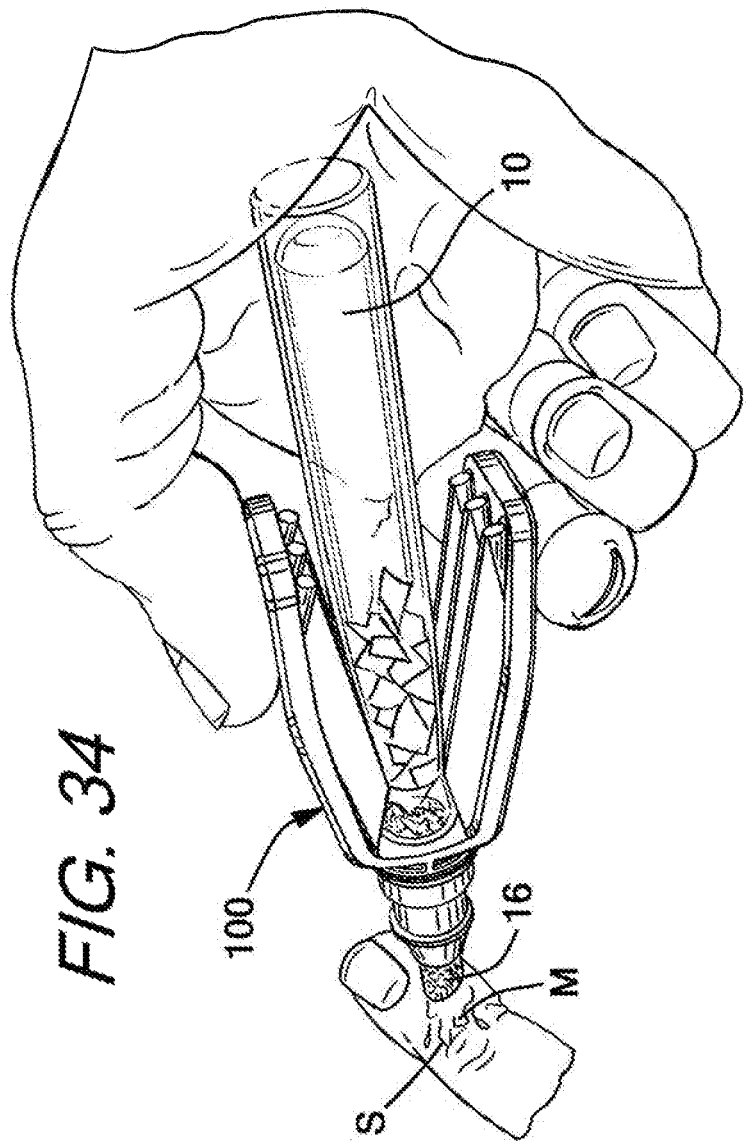

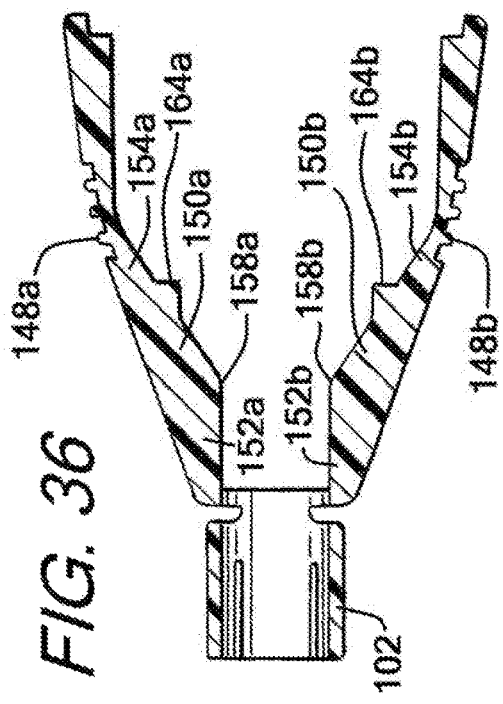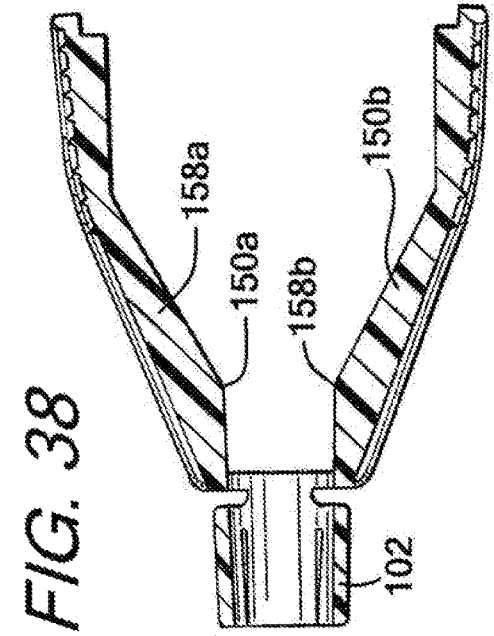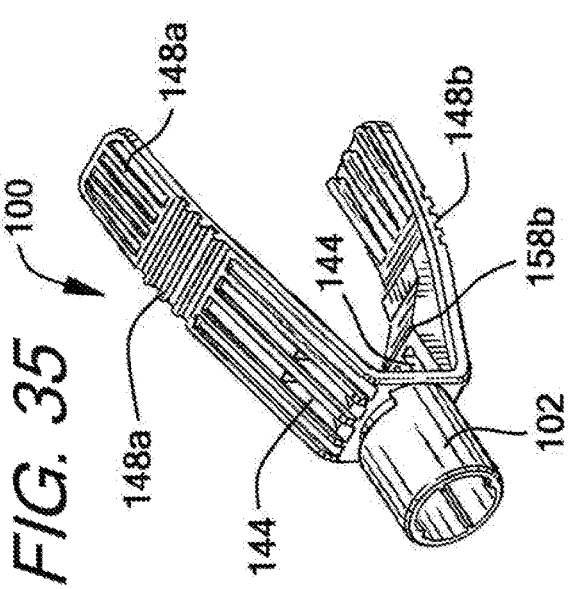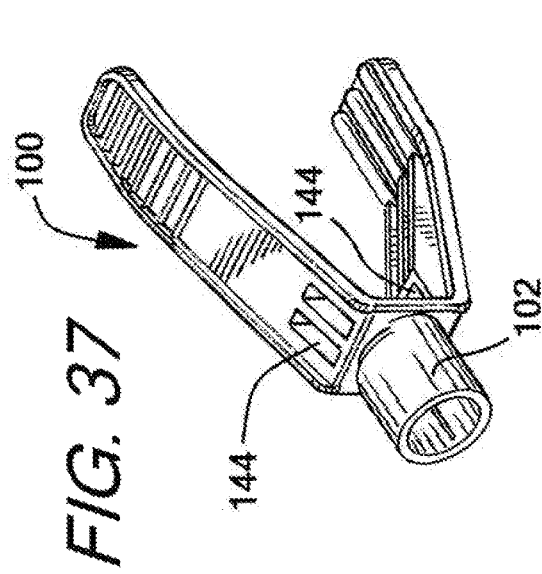

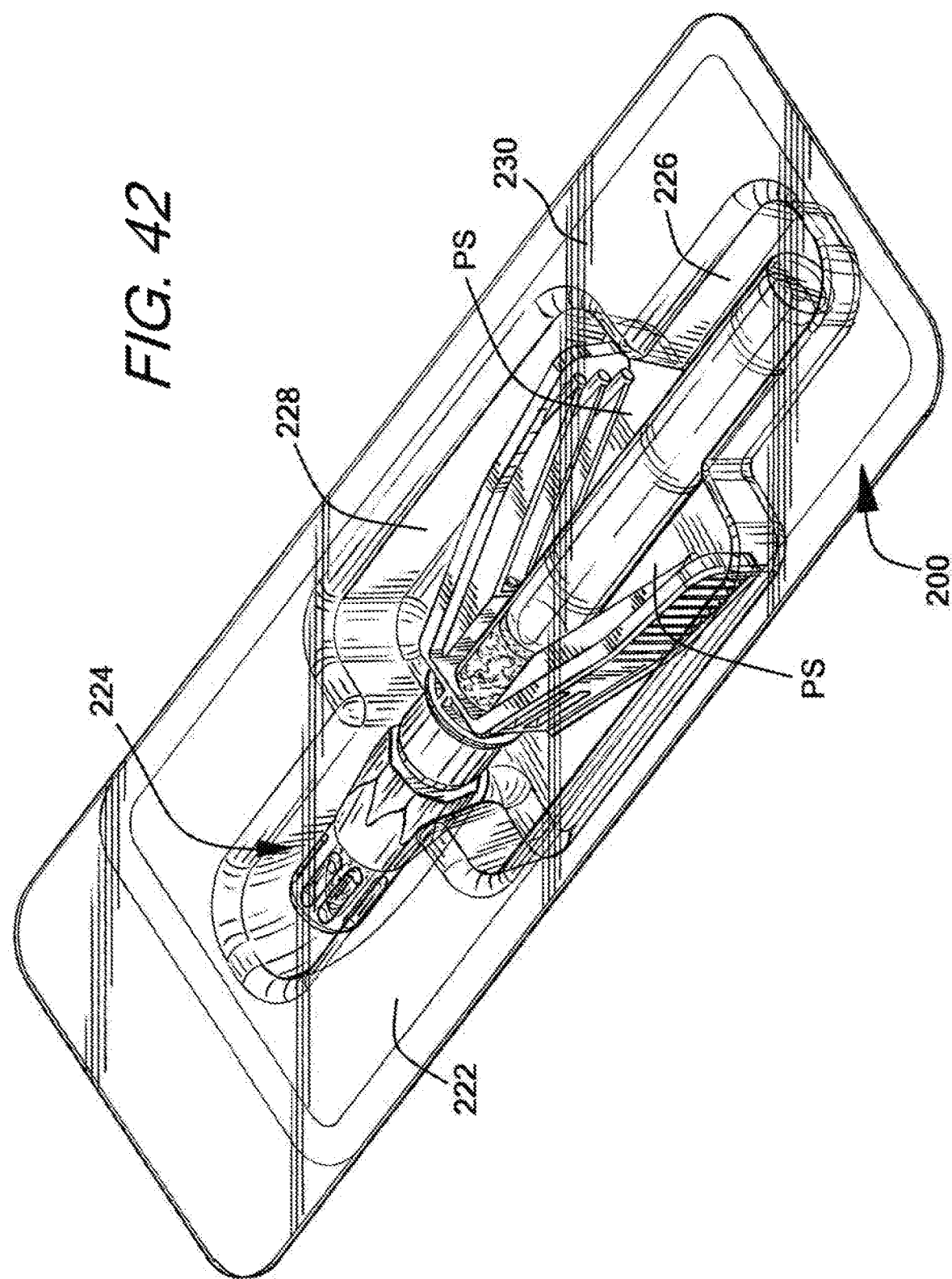

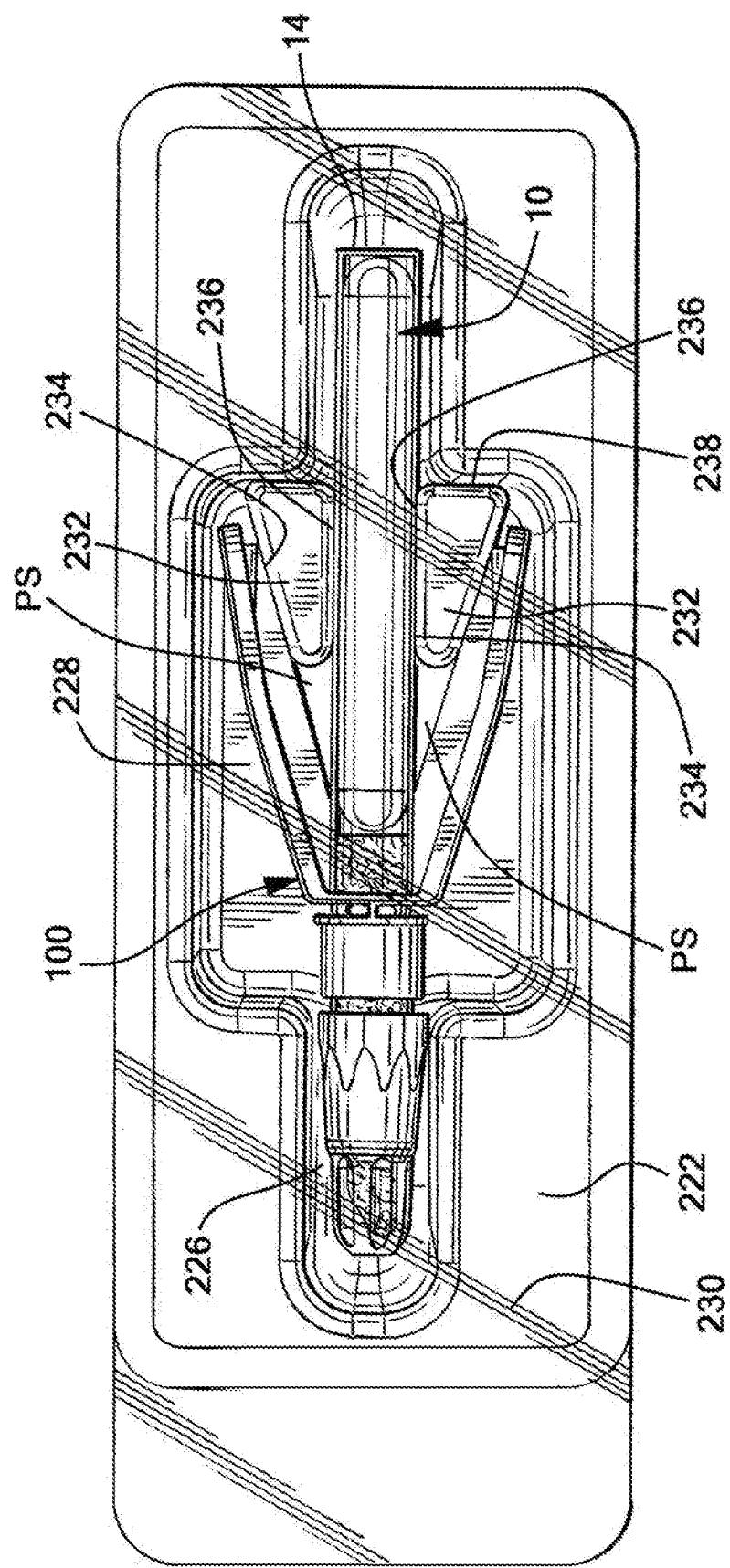

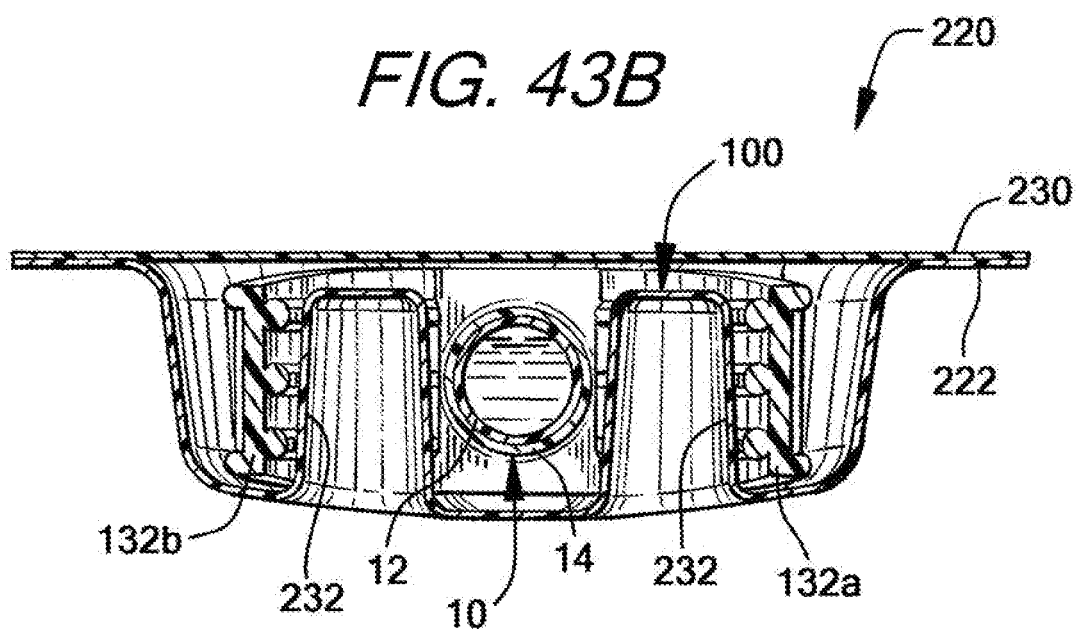
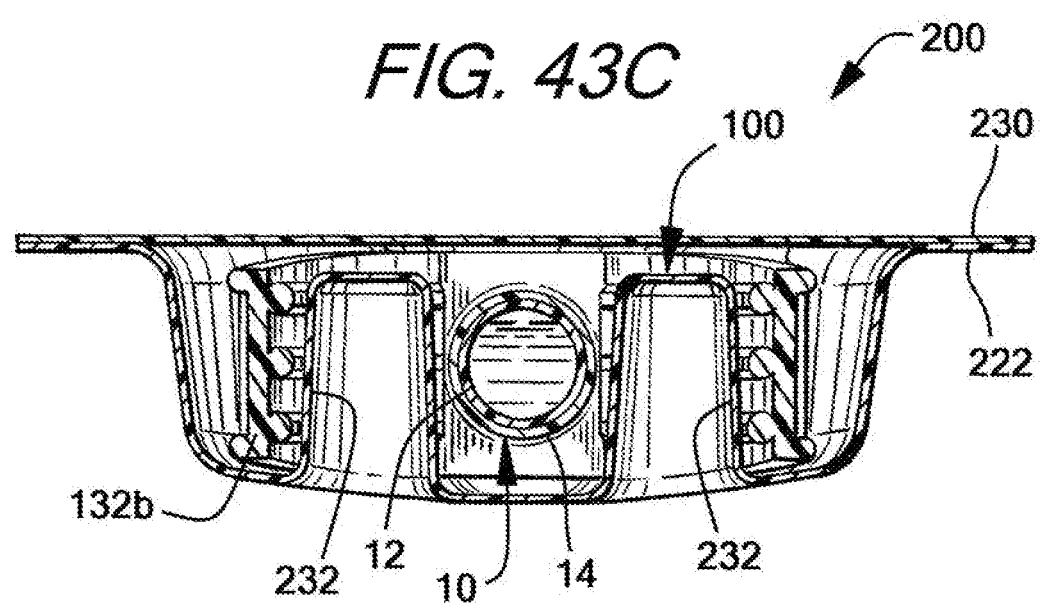

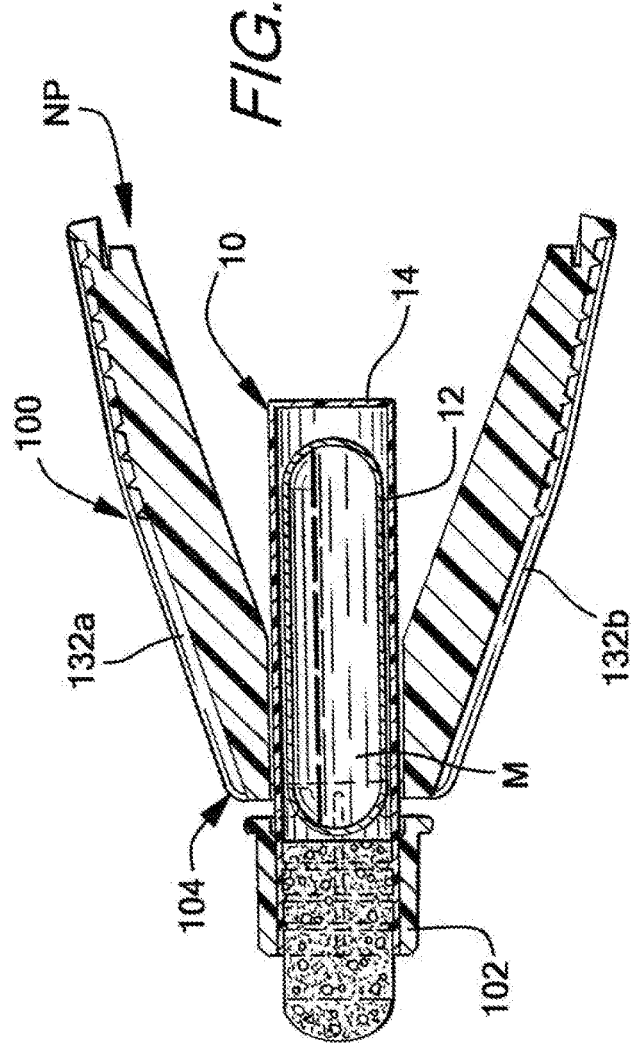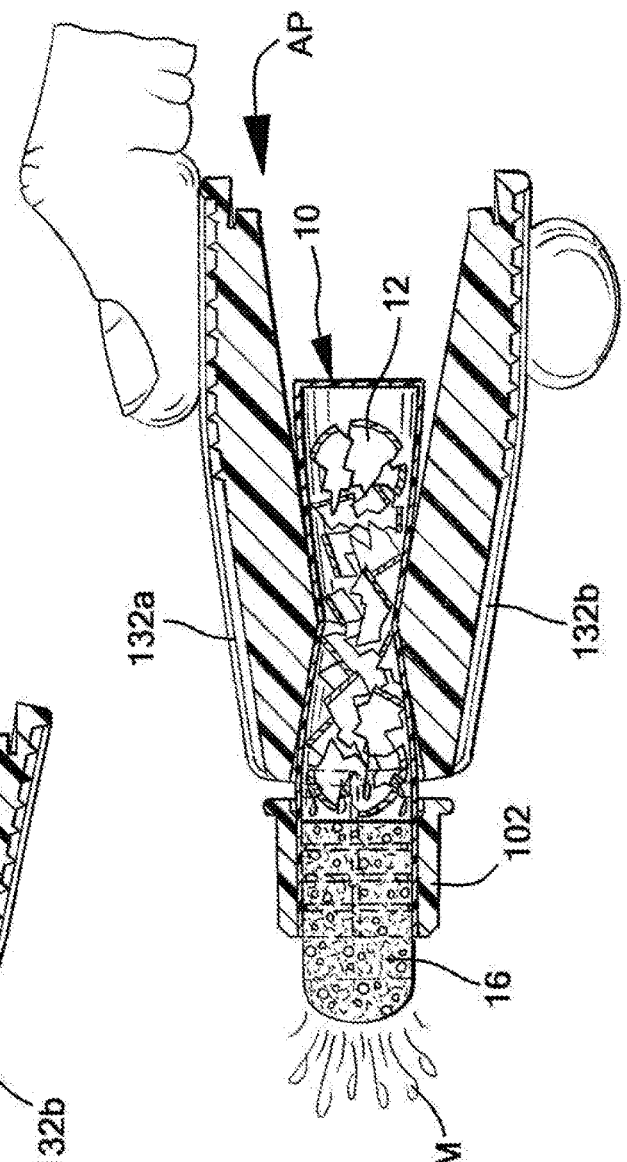

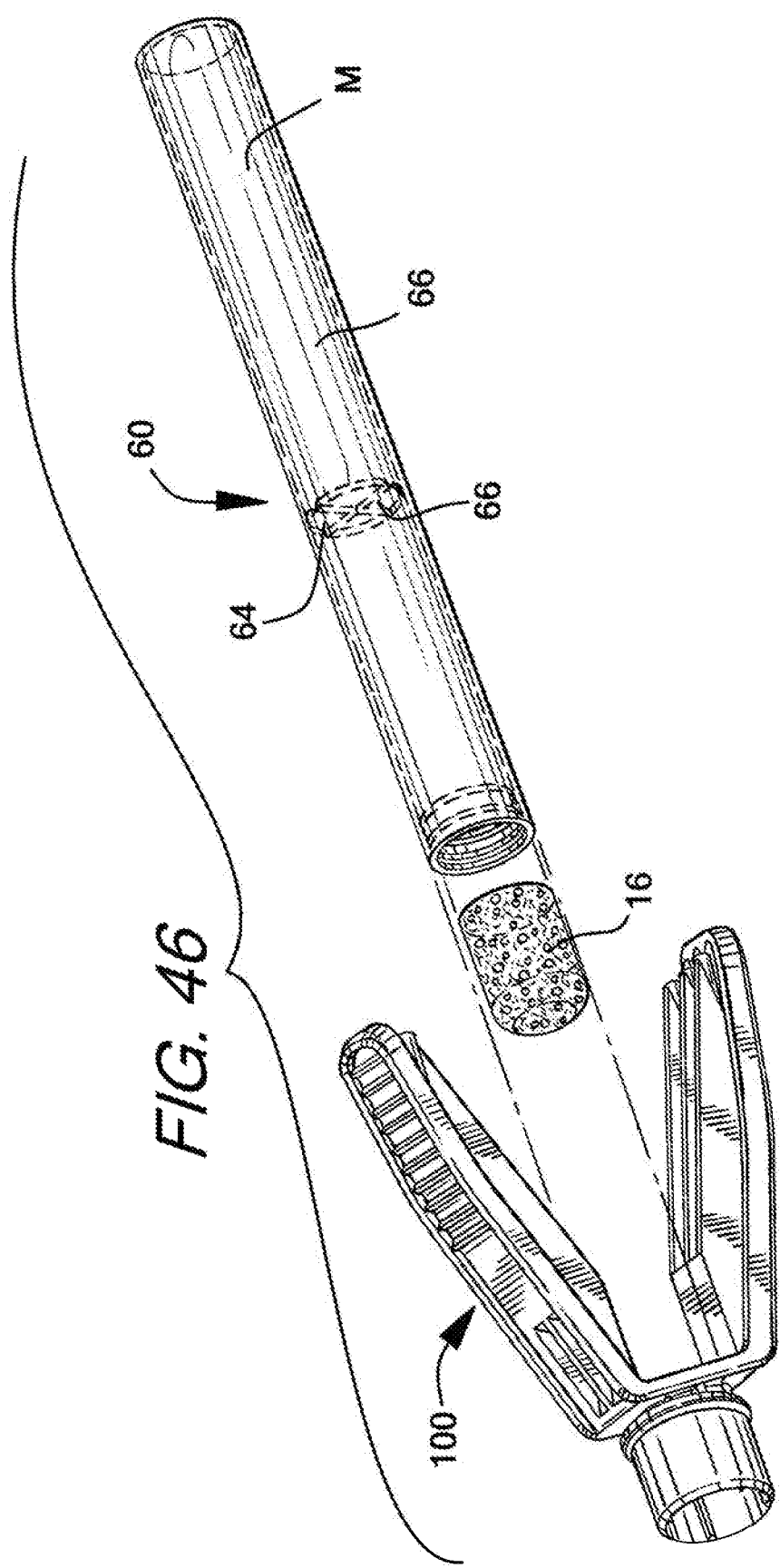

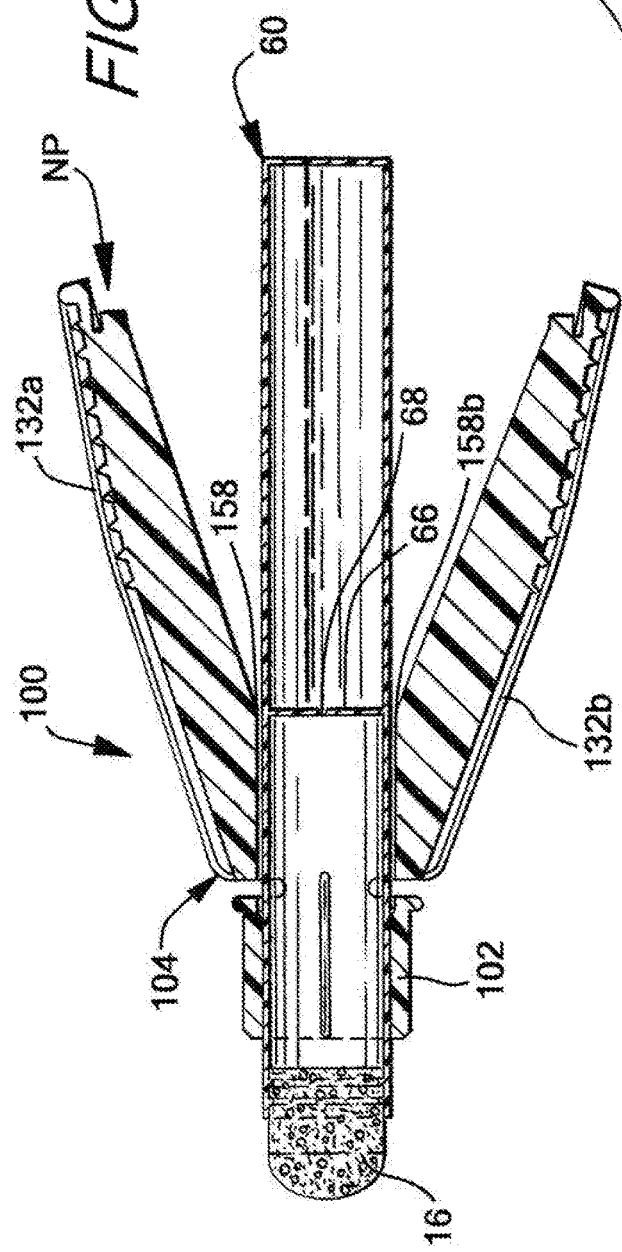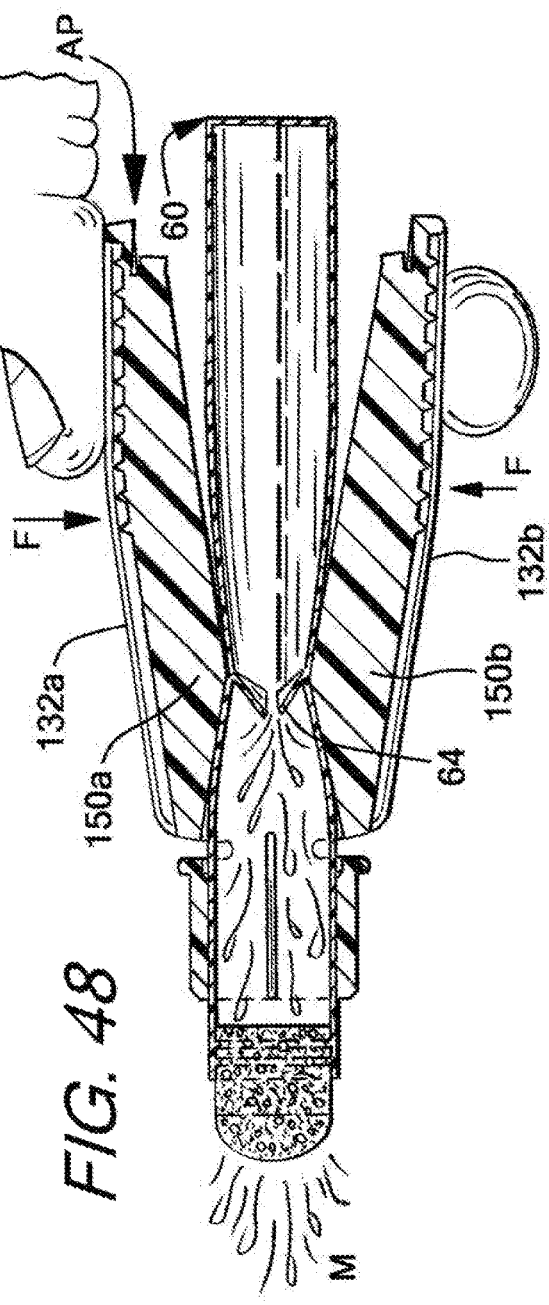

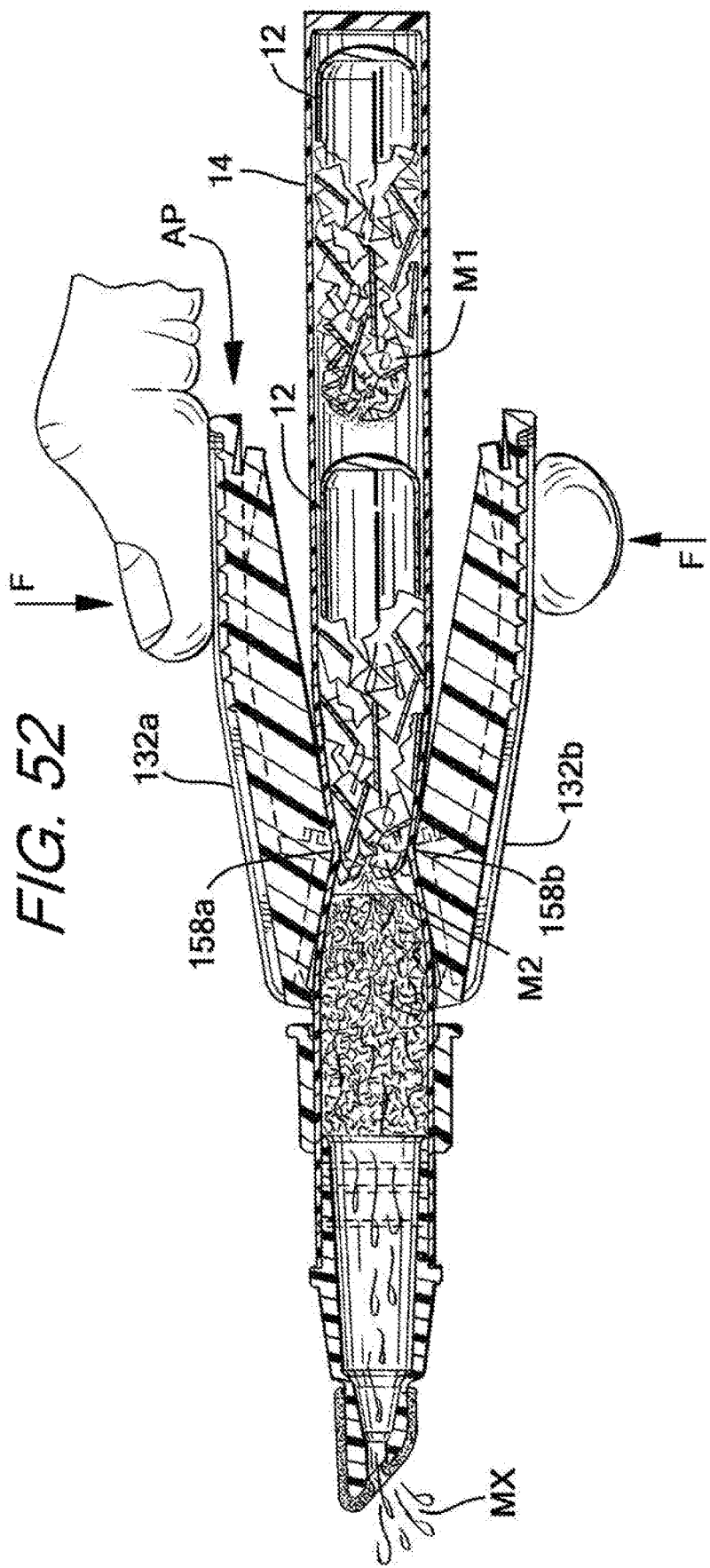

DISPENSER ACTUATOR ASSEMBLY

CROSS-REFERENCE TO RELATED APPLICATIONS

The present application claims the benefit of U.S. Patent Application No. 62/744,460, filed on Oct. 11, 2018, which application is incorporated by reference in its entirety and made a part hereof.

FEDERALLY SPONSORED RESEARCH OR DEVELOPMENT

None.

TECHNICAL FIELD

The invention relates generally to an actuator assembly for a dispenser and more particularly, to an dispenser actuator assembly having a base member configured to mount on a crushable glass ampoule assembly wherein an actuator assembly in the form of a first actuator arm and a second actuator arm are operably connected to the base member and dimensioned to crush the glass ampoule assembly.

BACKGROUND OF THE INVENTION

Dispensers such as glass ampoule assemblies are well known in the art and are often designed to be single-use disposable dispensers. A glass ampoule assembly typically includes a rupturable container such as a glass ampoule that contains a flowable material to be dispensed. The glass ampoule is contained in an outer container that may be made from a plastic material and having an open end and a closed end. The glass ampoule assembly may further include an applicator such as a swab that fits in the open end of the outer container. The applicator assists in dispensing the flowable material after the glass ampoule is ruptured, or crushed. The glass ampoule assembly may also include a cover member such as a cardboard sleeve that is used when initially storing and transporting the glass ampoule assembly wherein the applicator end of the glass ampoule assembly is inserted into the cardboard sleeve. An opposite end of the glass ampoule assembly may be inserted into the cardboard sleeve wherein the applicator extends out of the sleeve. A user may squeeze the cardboard sleeve via finger pressure to deflect the plastic outer container and crush the glass ampoule wherein the flowable material is dispensed from the applicator. Other glass ampoule assemblies may utilize a cap member that fits over the applicator rather than a cardboard sleeve.

Attempts have been made to design ampoule holders that assist in rupturing the ampoule. These designs, however, have been high in cost and cumbersome in design and operation. Furthermore, the glass ampoule is not crushed in an optimum location wherein dispensing of the flowable material becomes problematic because of obstruction from fractured pieces of the glass ampoule.

Additional problems have also been experienced with the glass ampoule assemblies. In some instances, users do not have sufficient finger strength to crush the glass ampoule. For example, users of advanced age oftentimes have arthritis and cannot crush the glass ampoule. In other instances, upon rupturing the glass ampoule, glass shards puncture through the outer container and injure the user. In still other instances, the glass ampoule is typically crushed at a central location of the glass ampoule. Rupturing the ampoule at the central location leaves a dome-shaped end portion of the glass ampoule intact. The dome-shaped end portion may end up positioned at the applicator wherein the flow of the flowable material is restricted from the dispenser. Furthermore, some actuator structures are integral with the overall dispenser assembly and do not provide an ability to be reused.

While glass ampoule assemblies and associated dispenser/ampoule holders/actuator assemblies according to the prior art provide a number of advantageous features, they nevertheless have certain limitations. The present invention seeks to overcome certain of these limitations and other drawbacks of the prior art, and to provide new features and new uses not heretofore available. A full discussion of the features and advantages of the present invention is deferred to the following detailed description, which proceeds with reference to the accompanying drawings.

SUMMARY OF THE INVENTION

The present invention provides a dispenser actuator assembly designed to actuate a dispenser to dispense a flowable material from the dispenser.

According to a first aspect of the invention, a dispenser actuator assembly is provided for actuating a dispenser such as a glass ampoule assembly. The glass ampoule assembly has a rupturable glass ampoule containing a flowable material. The glass ampoule is contained within an outer container. The outer container has a first open end and a second closed end and the glass ampoule assembly has an applicator positioned in the first open end. The dispenser actuator assembly has a base member configured to mount on the outer container. An actuator assembly is operably connected to the base member wherein the actuator assembly has a first actuator arm and a second actuator arm each pivotally connected to the base member. The first actuator arm and the second actuator arm extend from the base member in generally opposed relation defining a first position, or first neutral position. The first actuator arm has a first protrusion depending therefrom and the second actuator arm has a second protrusion depending therefrom. The first actuator arm and the second actuator arm are pivotable from the first position towards one another to a second position, or actuating position, wherein the first protrusion is configured to engage the outer container and the second protrusion is configured to engage the outer container to rupture the glass ampoule wherein the flowable material is configured to be dispensed from the glass ampoule assembly.

According to another aspect of the invention, a dispenser actuator assembly is provided for actuating a dispenser in the form of a glass ampoule assembly. The glass ampoule assembly has a rupturable glass ampoule containing a flowable material. The glass ampoule is contained within an outer container, the outer container having a first open end and a second closed end. The glass ampoule assembly has an applicator positioned in the first open end. The dispenser actuator assembly has a base member having an opening configured to mount on the outer container. An actuator assembly has a flex plate operably connected to the base member, the actuator assembly further having a first actuator arm and a second actuator arm each connected to opposite ends of the flex plate. The first actuator arm and the second actuator arm extend from the flex plate in generally opposed relation to define a first position, or first neutral position. The first actuator arm has a first protrusion depending therefrom and the second actuator arm having a second protrusion depending therefrom. The first actuator arm and the second actuator arm are pivotable from the first position towards one another to a second position, or actuating position, wherein the flex plate flexes wherein the first protrusion is configured to engage the outer container and the second protrusion is configured to engage the outer container to crush the glass ampoule wherein the flowable material is configured to be dispensed from the glass ampoule assembly.

According to another aspect of the invention, the base member is an annular ring dimensioned to be configured to fit circumjacently around the outer container. The annular ring defines an inner surface. The inner surface has a plurality of ribs extending from the inner surface, the ribs configured to engage the outer container when the base member is mounted on the outer container. The opening of the base member extends completely through the base member.

According to a further aspect of the invention, a first slot is defined between the base member and a first end of the flex plate. A second slot is defined between the base member and a second end of the flex plate, the second slot being generally opposite the first slot.

According to a further aspect of the invention, the flex plate has a first end connected to a proximal end of the first actuator arm and the flex plate has a second end connected to a proximal end of the second actuator arm. The flex plate has a first flexion segment positioned adjacent the first end of the flex plate. The flex plate further has a second flexion segment positioned adjacent the second end of the flex plate. When the first actuator arm and the second actuator arm are pivoted to the second position, the flex plate flexes at the first flexion segment and the second flexion segment.

According to another aspect of the invention, the flex plate has a central portion having a flex plate opening therethrough, the flex plate opening being generally aligned with the opening of the base member. The flex plate opening is configured to receive the outer container when the base member is configured to mount on the outer container. In an exemplary embodiment, the flex plate opening has a diameter larger than a diameter of the opening of the base member.

According to another aspect of the invention, the flex plate has a first side rail extending between a proximal end of the first actuator arm and a proximal end of the second actuator arm, and a second side rail extending between a proximal end of the first actuator arm and a proximal of the second actuator arm. The central portion of the flex plate has a thickness less than a thickness of the first side rail and a thickness of the second side rail.

According to a further aspect of the invention, the flex plate has a central portion having a flex plate opening therethrough. The first flexion segment is defined between the flex plate opening and the first end of the flex plate and the second flexion segment is defined between the flex plate opening and the second end of the flex plate.

According to yet another aspect of the invention, the connection of the first end of the flex plate to the proximal end of the first actuator arm defines a first connection line and the connection of the second end of the flex plate to the proximal end of the second actuator arm defines a second connection line. When the first actuator arm and the second actuator arm are in the second position and the first flexion segment and the second flexion segment flex, the first actuator arm does not pivot about the first connection line and the second actuator arm does not pivot about the second connection line.

According to another aspect of the invention, when the first actuator arm and the second actuator arm are in the first position, the flex plate has a generally planar configuration.

According to a further aspect of the invention, the flexing of the first flexion segment and the second flexion segment does not apply force to the base member.

According to another aspect of the invention, the flex plate is operably connected to the base member by a connector member. The connector member has a first segment and a second segment spaced from the first segment. The first segment has a first end connected to the base member and a second end connected to the flex plate. The second segment has a first end connected to base member and a second end connected to the flex plate.

According to a further aspect of the invention, the base member has a flange and the flex plate has a first side rail and a second side rail. The first segment has a first raised tab, the first raised tab having a first end connected to the flange and a second end connected to the first side rail. The second segment has a second raised tab, the second raised tab having a first end connected to the flange and a second end connected to the second side rail.

According to another aspect of the invention, the first actuator arm has a peripheral flange and a floor segment. The floor segment is recessed with respect to the peripheral flange. The second actuator arm has a peripheral flange and a floor segment, and the floor segment of the second actuator arm is recessed with respect to the peripheral flange.

According to a further aspect of the invention, the first actuator arm has a proximal end adjacent to the flex plate, the first actuator arm having an aperture therein proximate the proximal end. The second actuator arm has a proximal end adjacent to the flex plate, the second actuator arm having an aperture proximate the proximal end. In an exemplary embodiment, the apertures do not extend completely through the first actuator arm and the second actuator arm.

According to a further aspect of the invention, the first actuator arm has a floor segment having a plurality of ridges at a distal end of the first actuator arm. The second actuator arm has a floor segment having a plurality of ridges at a distal end of the second actuator arm.

According to a further aspect of the invention, when the first actuator arm and the second actuator arm are in the first position, the first protrusion is configured to be spaced from the outer container and the second protrusion is configured to be spaced from the outer container.

According to another aspect of the invention, the first actuator arm has a distal end and an underside surface opposite a floor segment of the first actuator arm. The first actuator arm has a boss connected to the underside surface and proximate the distal end, wherein an indentation is defined between the boss and the underside surface. The second actuator arm has a distal end and an underside surface opposite a floor segment of the first actuator arm. The second arm having a boss connected to the underside surface and proximate the distal end, wherein an indentation is defined between the boss and the underside surface.

According to another aspect of the invention, the first protrusion has a first segment and a second segment and a first interface edge defined between the first segment and a second segment. The first interface edge is configured to engage the outer container to crush the glass ampoule. The second segment defines an inclined surface from the first interface edge to a distal end of the first actuator arm. In one exemplary embodiment, the second segment comprises a plurality of spaced walls. In a further exemplary embodiment, a slot is defined between a distal end of the spaced walls and an underside surface of the first actuator arm.

According to another aspect of the invention, the second protrusion has a first segment and a second segment and a second interface edge defined between the first segment and a second segment. The second interface edge is configured to engage the outer container to crush the glass ampoule. The second segment of the second protrusion defines an inclined surface from the second interface edge to a distal end of the second actuator arm. In one exemplary embodiment, the second segment of the second protrusion comprises a plurality of spaced walls. In a further exemplary embodiment, a slot is defined between a distal end of the spaced walls and an underside surface of the second actuator arm.

According to a further aspect of the invention, the glass ampoule has an interface area defined generally between a dome-shaped closed end and a generally cylindrical central potion. When the base member is configured to be mounted on the outer container, the first protrusion and the second protrusion are configured to be positioned proximate the interface area of the glass ampoule. When the first actuator arm and the second actuator arm are placed in the second position, the first protrusion and the second protrusion are configured to crush the glass ampoule at the interface area.

According to another aspect of the invention, the base member has a diameter distance wherein the base member is configured to support the glass ampoule assembly across the diameter distance. The first actuator arm and the second actuator arm are connected to the flex plate along connection lines having a lateral distance. The lateral distance is greater than the diameter distance.

According to yet another aspect of the invention, a dispenser and actuator assembly package assembly is provided. A dispenser has a crushable glass ampoule containing a flowable material. The glass ampoule is contained within an outer container, the outer container having a first open end and a second closed end. An applicator is positioned in the first open end. An actuator assembly has a base member mounted on the outer container of the dispenser. An actuator assembly is operably connected to the base member wherein the actuator assembly has a first actuator arm and a second actuator arm each pivotally connected to the base member. The first actuator arm and the second actuator arm extend from the base member in generally opposed relation to define a first position. The first actuator arm has a first protrusion depending therefrom and the second actuator arm has a second protrusion depending therefrom. A blister package has a blister layer defining a recess. The actuator assembly mounted on the dispenser is received by the recess wherein a first recess space is defined in the recess between the first actuator arm and the outer container, and a second recess space is defined in the recess between the second actuator arm and the outer container. A first blocking member is positioned in the first recess space preventing movement of the first actuator arm from the first position towards the outer container. A second block member is positioned in the second recess space preventing movement of the second actuator arm from the first position towards the outer container. A cover member is secured to the blister layer enclosing the actuator assembly, dispenser, first blocking member and the second blocking member in the blister recess.

According to another aspect of the invention, the first blocking member is a separate member from the blister layer. The second blocking member is a separate member from the blister layer.

According to a further aspect of the invention, the first blocking member is integrally formed in the blister layer. The second blocking member is integrally formed in the blister layer.

According to another aspect of the invention, the first protrusion of the first actuator member has a first inclined surface and the outer container has a straight cylindrical outer surface. The first blocking member has a first angled surface and a first primary linear surface. The first inclined surface of the first protrusion confronts and engages the first angled surface of the first blocking member and the straight cylindrical surface of the outer container confronts and engages the first primary linear surface of the first blocking member. The second protrusion of the second actuator member has a second inclined surface, and the second blocking member has a second angled surface and a second primary linear surface. The first inclined surface of the second protrusion confronts and engages the second angled surface of the second blocking member. The straight cylindrical surface of the outer container confronts and engages the second primary linear surface of the second blocking member.

According to a further aspect of the invention, the first blocking member has a circular cross-section, and the second blocking member has a circular cross-section.

According to another aspect of the invention a dispenser and actuator assembly are provided wherein the dispenser is a plastic ampoule assembly. The plastic ampoule assembly has a container having a first chamber and a second chamber. The first chamber contains a flowable material, and the second chamber defines an open end. A membrane is disposed within the container separating the first chamber and the second chamber, the membrane having a thickness and a weld seam, the weld seam having a thickness less than the thickness of the membrane. An applicator is positioned in the open end. An actuator assembly has a base member mounted on the container. An actuator assembly has a flex plate operably connected to the base member. The actuator assembly further has a first actuator arm and a second actuator arm each connected to opposite ends of the flex plate. The first actuator arm and the second actuator arm extends from the flex plate in generally opposed relation to define a first position. The first actuator arm has a first protrusion depending therefrom and the second actuator arm has a second protrusion depending therefrom. The first actuator arm and the second actuator arm are pivotable from the first position towards one another to a second position wherein the flex plate flexes wherein the first protrusion engages and deflects the container inwardly proximate the membrane and the second protrusion engages and deflects the container inwardly proximate the membrane to fracture the weld seam of the membrane wherein the flowable material passes from the first chamber past the membrane and into the second chamber wherein the flowable material is dispensed from the applicator.

According to a further aspect of the invention, the actuator assembly is used with a tandem glass ampoule assembly having multiple crushable glass ampoules contained in an outer container. The actuator assembly is slidably moveable along the container to crush the glass ampoule as respective interface areas of the glass ampoules.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is a front perspective view of a dispenser in the form of a glass ampoule assembly;

FIG. 2 is an exploded front perspective view of the glass ampoule assembly shown in FIG. 1;

FIG. 5 is a front perspective view of another dispenser in the form of an alternative embodiment of a glass ampoule assembly;

FIG. 6 is an exploded front perspective view of the glass ampoule assembly shown in FIG. 5;

FIG. 7 is an exploded front perspective view of the glass ampoule assembly shown in FIG. 5 but with a cover member omitted and also the dispenser actuator assembly;

FIG. 8 is a front perspective view of the dispenser actuator assembly mounted on the glass ampoule assembly of FIG. 5;

FIG. 9 is a front perspective view of the dispenser actuator assembly according to an exemplary embodiment of the invention;

FIG. 10 is a rear perspective view of the dispenser actuator assembly shown in FIG. 9;

FIG. 11 is a side elevation view of the dispenser actuator assembly shown in FIG. 9;

FIG. 12 is a top plan view of the dispenser actuator assembly shown in FIG. 9, a bottom view being general identical;

FIG. 13 is a front elevation view of the dispenser actuator assembly shown in FIG. 9;

FIG. 14 is a rear elevation view of the dispenser actuator assembly shown in FIG. 9;

FIG. 15 is an enlarged rear perspective view of the dispenser actuator assembly shown in FIG. 9;

FIG. 16 is a cross-sectional view of the dispenser actuator assembly taken along Line 16-16 of FIG. 12;

FIG. 17 is a partial side elevation view of the dispenser actuator assembly mounted on the glass ampoule assembly of FIG. 1;

FIG. 18 is a partial front perspective view of the dispenser actuator assembly;

FIG. 19 is a front perspective view of a core mold member used in injection molding the dispenser actuator assembly of FIG. 9;

FIG. 20 is a side elevation view of the core mold member of FIG. 19;

FIG. 21 is a top plan view of the core mold member of FIG. 19;

FIG. 22 is a front elevation view of the core mold member of FIG. 19;

FIG. 23 is a cross-sectional view of the core mold member;

FIG. 28A is a front perspective view of the dispenser actuator assembly ejected from the core mold member;

FIG. 28B is an enlarged partial cross-sectional view showing a pin portion of the core mold member removed from the dispenser actuator assembly;

FIG. 31 is a partial enlarged side elevation view of the dispenser actuator assembly mounted on the dispenser and showing actuation of the dispenser and further showing flexion of a flex plate of the dispenser actuator assembly;

FIG. 32 is a partial front perspective view of the dispenser actuator assembly mounted on the dispenser and showing actuation of the dispenser and further showing flexion of the flex plate of the dispenser actuator assembly;

FIG. 33 is a partial side elevation view of the dispenser actuator assembly mounted on the dispenser and showing actuator of the dispenser and further manipulation of the dispenser in dispensing flowable material from the dispenser;

FIG. 34 is a perspective view of a user engaging the dispenser actuator assembly mounted on the dispenser wherein the dispenser is actuated wherein flowable material is dispensed from the dispenser onto a skin surface;

FIG. 35 is a front perspective view of an alternative embodiment of a dispenser actuator assembly according to an exemplary embodiment of the invention;

FIG. 36 is a side cross-sectional view of the dispenser actuator assembly shown in FIG. 35;

FIG. 37 is a front perspective view of another alternative embodiment of a dispenser actuator assembly according to an exemplary embodiment of the invention;

FIG. 38 is a side cross-sectional view of the dispenser actuator assembly shown in FIG. 37;

FIG. 42 is a perspective view of the dispenser actuator assembly mounted on the dispenser in a blister-type package assembly;

FIG. 43A is a top plan view of the dispenser actuator assembly mounted on the dispenser in a blister package and having wedge members positioned between the actuator arms and dispenser;

FIG. 43B is a cross-sectional view of the dispenser actuator assembly mounted on the dispenser in a blister package wherein the blister package is formed with integral wedge members positioned between the actuator arms and the dispenser;

FIG. 43C is a cross-sectional view of the dispenser actuator assembly mounted on the dispenser in a blister package wherein the blister package is formed with alternative integral wedge members positioned between the actuator arms and the dispenser;

FIG. 44 is a side cross-sectional view of the dispenser actuator assembly mounted on the glass ampoule assembly of FIGS. 5-8;

FIG. 45 is a side cross-sectional view of the dispenser actuator assembly mounted on the glass ampoule assembly of FIGS. 5-8 and showing actuation of the dispenser;

FIG. 46 is an exploded perspective view of the dispenser actuator assembly and an alternative form of the dispenser in the form of a plastic ampoule assembly;

FIG. 47 is a side cross-sectional view of the dispenser actuator assembly mounted on the plastic ampoule assembly of FIG. 46;

FIG. 48 is a side cross-sectional view of the dispenser actuator assembly mounted on the plastic ampoule assembly of FIG. 46 and showing actuation of the plastic ampoule assembly;

FIG. 52 is a side cross-sectional view of the dispenser actuator assembly mounted on the dispenser of FIG. 49 and showing actuation of the dispenser actuator assembly wherein the front glass ampoule in the dispenser is crushed.

DETAILED DESCRIPTION OF THE PREFERRED EMBODIMENT

Figure 3:
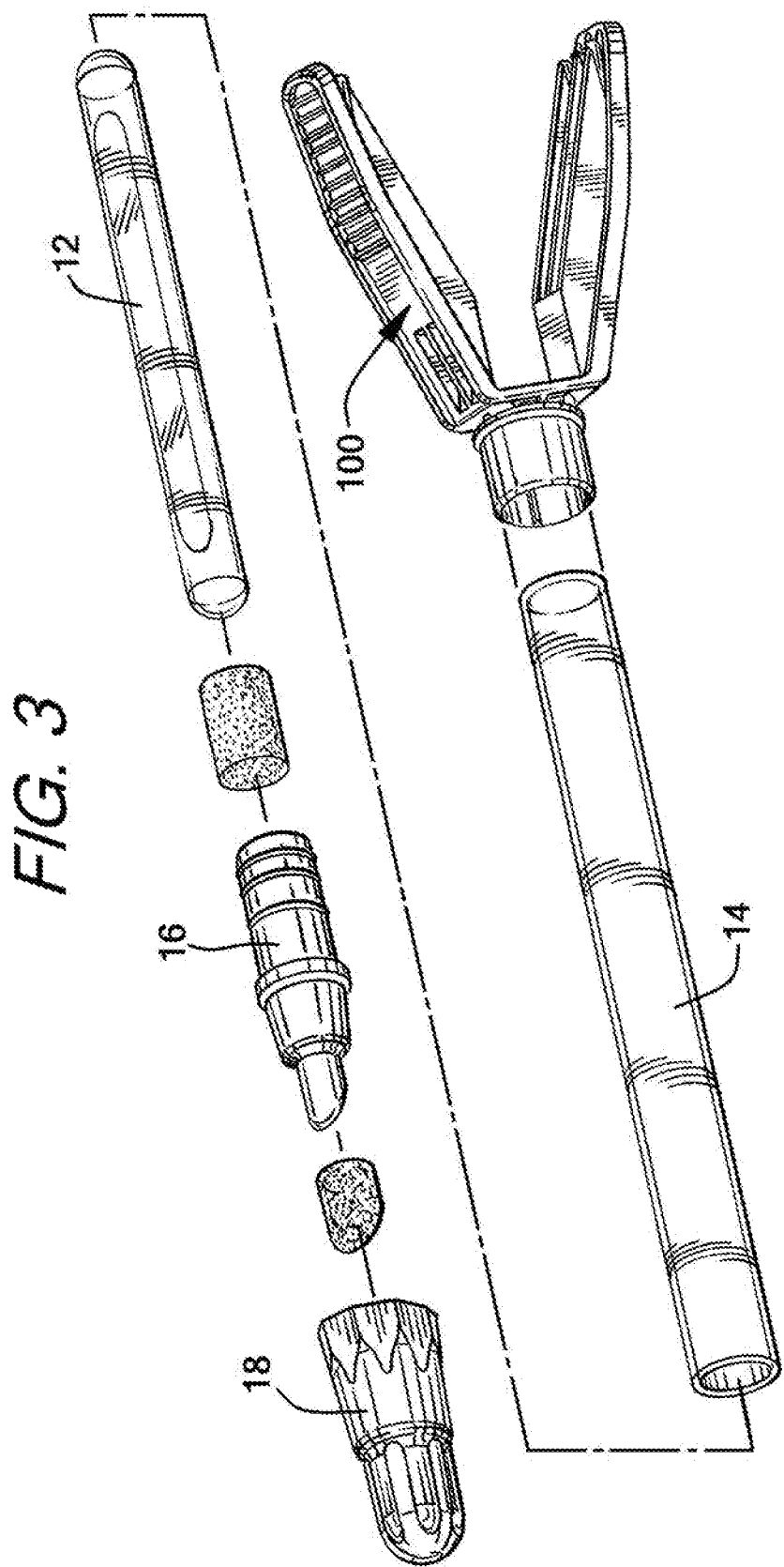
FIG. 3 is an exploded front perspective view of the glass ampoule assembly shown in FIG. 1 and also a dispenser actuator assembly according to an exemplary embodiment of the invention.
Figure 4:
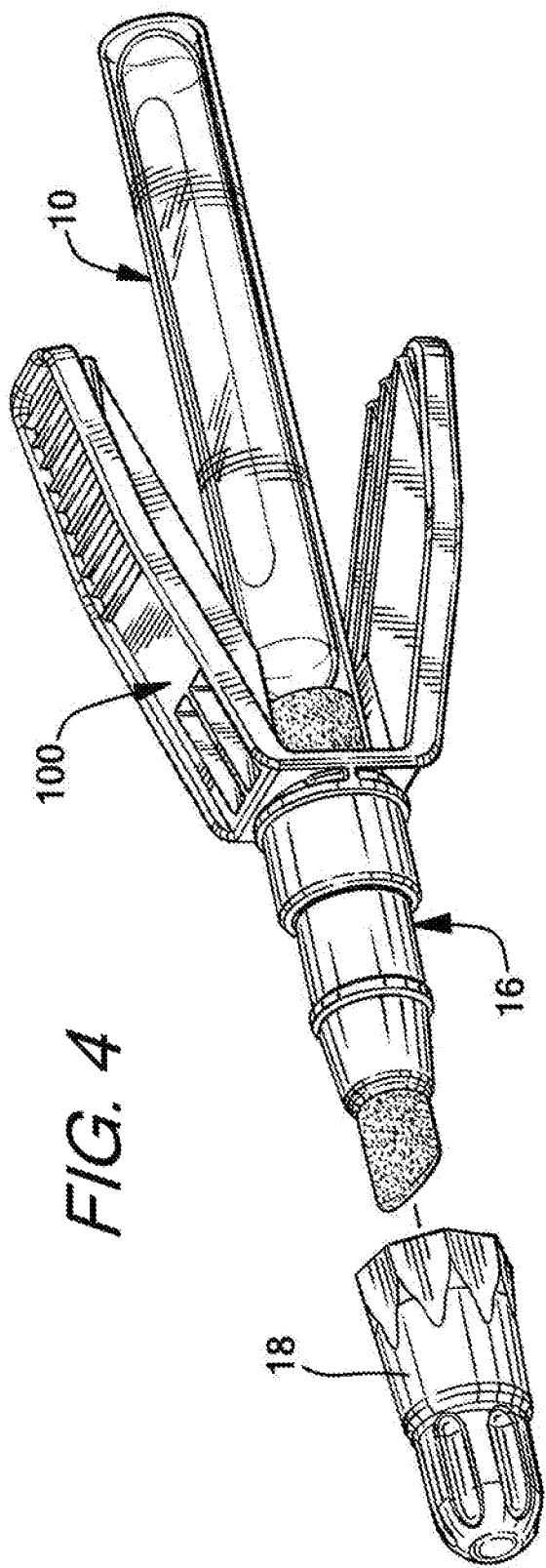
FIG. 4 is a front perspective view of the dispenser actuator assembly mounted on the dispenser in the form of the glass ampoule assembly.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention discloses a dispenser actuator assembly that can be used in conjunction with a dispenser to activate the dispenser and dispense flowable material from the dispenser. The dispenser actuator assembly may also be referred to as an ampoule actuator assembly or a dispenser holder or ampoule holder. The dispenser can take various forms and in one particular application, the dispenser may take the form of a glass ampoule assembly. The dispenser in the form of the glass ampoule assembly will be described followed by describing the dispenser actuator assembly including the connection of the components and actuating the dispenser.

FIGS. 1-4 disclose a dispenser used in accordance with an exemplary embodiment of the invention and generally designated with the reference numeral 10. The dispenser 10 generally includes a first container 12, a second container 14, or outer container 14, and an applicator assembly 16. A cover member 18 or cap member 18 may optionally be utilized as explained in greater detail below. In this configuration, the dispenser 10 may also be referred to as a glass ampoule assembly 10. The glass ampoule assembly 10 generally has an elongated longitudinal axis. It is understood that the dispenser 10 or glass ampoule assembly 10 may take different forms as well such as other devices having rupturable containers.

FIGS. 1-4 further the first container 12. The first container 12 is generally structured to contain the flowable material M to be dispensed from the dispenser 10. The flowable material M is typically a liquid in an exemplary embodiment. It is understood, however, that flowable materials in other forms could be used such as gels or powders etc. The first container 12 defines a chamber 20 therein that contains the flowable material M. The first container 12 has a first end 22 that is closed and also has a second end 24 that is closed as well as an intermediate section 26 therebetween. The intermediate section 26 of the first container 12 is generally cylindrical in shape and has a generally circular cross-section. The first end 22 is generally dome-shaped and the second end 24 is generally dome-shaped. Other configurations are also possible. As further shown in FIGS. 1-4, a first interface area 28 is defined at or proximate the juncture between the first dome-shaped end 22 and an end of the intermediate section 26. Similarly, a second interface area 30 is defined at or proximate the juncture between the second dome-shaped end 24 and the other end of the intermediate section 26. Thus, the first interface area 28 is at the location of the first container 12 that transitions from an end of the intermediate section 26 to the dome shape of the first end 22. Similarly, the second interface area 30 is at the location of the first container 12 that transitions from an end of the intermediate section 26 to the dome shape of the second end 24. The first container 12 may be dimensioned to have a diameter and length to define the first chamber 20 in a size to contain a desired amount of the flowable material M. The first container 12 is designed to be fracturable, frangible, rupturable or crushable as described in greater detail below. In an exemplary embodiment, the first container 12 is made from a rigid frangible or crushable material such as glass. The first container 12 may be a traditional glass ampoule. Glass ampoules are known in the art and provide a hermetically-sealed chamber for containing the flowable material M. In one exemplary embodiment, a single glass ampoule 12 is used. It is understood that the dispenser 10 could be configured to use multiple glass ampoules 12 as described in greater detail below.

FIGS. 1-4 further show the second container 14, or outer container 14, which can be in the form of an applicator body. The second container 14 has an open first end 36 and a closed second end 38, and an outer wall 40 therebetween. The outer wall 40 of the second container 14 defines a second chamber 42. The second chamber 42 is cooperatively dimensioned and configured to receive at least a portion of the first container 12, and typically the entire first container 12 is received in the second container 14. Thus, in an exemplary embodiment, the second container 14 is generally cylindrical and receives the first container 12 in a generally snug-fit configuration. The second container 14 is made from a flexible resilient material such as plastic in an exemplary embodiment. The second container 14 may be transparent or translucent plastic wherein the flowable material M in the first container 12 can be visible through the second container 14 and also through the first container 12.

The second container 14 may also be made from opaque material when the flowable material M or other contents are light sensitive.

FIGS. 1-4 also show the applicator 16 or applicator assembly 16. The applicator assembly 16 assists in dispensing the flowable material M from the dispenser 10 to a receiving surface. Any applicator assembly 16 that performs this function can be used in the dispenser 10. Thus, the applicator assembly 16 can take various forms including a swab assembly, a dropper assembly, a roller ball or a brush assembly. The applicator assembly 16 can further be a sponge, foam applicator, fabric, gauze, pen-type applicator or flocked tip. The swab applicator may also take various forms such as being made from absorbent, porous material, and that relies on a wicking action to dispense the flowable material M. It is also understood that the applicator assembly 16 may have a filter member 44 operably associated therewith. The filter member 44 is structured to allow passage of the flowable material M through the filter member 44 while preventing passage of glass shards from the fractionated glass ampoule 12. The filter member 44 may be positioned between the first end 22 of the first container 12 and the applicator assembly 16. Further, the filter member 44 may be positioned between the glass ampoule 12 and a tip of the applicator assembly 16.

In the exemplary embodiment of the applicator assembly 16 of FIGS. 1-4, the applicator assembly 16 has a hub 46 or base member 46 having a first end 48 and a second end 50. It is understood that the base member 46 has an internal conduit that is in fluid communication with the second container 14 for the flowable material M to pass through the conduit and onto a receiving surface. The first end 48 is dimensioned to fit into the open first end of the second container 36. The second end has a post 52 that receives a tip 54. The tip 54 can be made from the various materials as described above wherein the flowable material M can be dispensed from the tip 54 and onto a receiving surface. In one exemplary embodiment, the tip 54 could be a flocked tip for enhanced dispensing of the flowable material M.

In another exemplary embodiment, the applicator assembly 16 could be in the form of a swab assembly. The swab assembly can be made from material that promotes dispensing of the flowable material M through the swab assembly and onto a receiving surface. The applicator assembly 16 can also include other types of tips capable of applying flowable material onto a receiving surface.

In another exemplary embodiment, the applicator assembly 16 can be in the form of a dropper assembly. The applicator assembly 16 has a base having a protrusion extending therefrom at one end. The base has a dropper tip member extending from an opposite end. The applicator assembly 16 has a central conduit extending therethrough from a distal end of the protrusion to a distal end of the dropper tip member. The protrusion has a generally annular configuration and is dimensioned to be received by the open first end 36 of the second container 14. In an exemplary embodiment, the protrusion and the open first end 36 of the second container 14 are cooperatively dimensioned wherein the protrusion is received in the open first end 36 in an interference fit. As further described below, the applicator assembly 16 is configured to receive the flowable material M from the fractionated or crushed first container 12 and to dispense the flowable material M onto a receiving surface.

To fabricate the dispenser 10, the first chamber 20 of the first container 12 is filled with a desired flowable material M. The open end of the first container 12 through which the flowable material passed to fill the first container 12 is sealed as is known in glass ampoule technology. A sealed glass ampoule 12 having the flowable material M therein is thereby provided. The filled first container 12 is then inserted through the open first end 36 and into the second chamber 42 of the second container 14. Preferably, the first container 12 is positioned in its entirety within the second chamber 42 of the second container 14. The filter member 44, if utilized, is inserted into the open first end 36 of the second container 14 and adjacent the first end of the first container 12. Once the first container 12 is positioned in the second container 14 as well as the filter member 44, the applicator assembly 16 is connected to the second container 14. Thus, the filter member 44 is positioned between the glass ampoule 12 and the applicator assembly 16. As can be appreciated from FIGS. 1-4, the first end 48 of the applicator assembly 16 is inserted into the open first end 36 of the second container 14. This connection may be in an interference fit, snap-fit or connected with adhesives as well. The tip 54 is secured to the post 52.

The cover member 18 is designed to initially cover the applicator assembly 16 prior to activating the dispenser 10. The cover member 18 is dimensioned to fit snugly over the applicator assembly 16, cover the tip 54 and extend over a portion of the dispenser 10. A distal end of the cover member 18 is a closed end. When preparing to activate the dispenser 10, the cover member 18 is removed from the dispenser 10. With the present invention as described in further detail below, the cover member 18 is not used during activation of the dispenser 10. It is also understood that the dispenser 10 can incorporate an identifying label.

It is understood that the dispenser 10 utilizes the cover member 18 in a single-use type container as described above and shown in FIGS. 1-4. The dispenser 10 may also eliminate the cover member 18 and be packaged in other outer packaging such as blister packaging.

FIGS. 5-8 disclose another exemplary embodiment of a glass ampoule assembly. The assembly has generally similar structures as the glass ampoule assembly 10 of FIGS. 1-4 and like structures will be designated with identical reference numerals. As shown in FIGS. 5-8, the glass ampoule assembly 10 generally includes a first container 12, a second container 14, or outer container 14, and an applicator assembly 16. The elements are structured and connected as with the glass ampoule assembly of FIGS. 1-4. An alternative form of the cap member 18 is utilized in the embodiment of FIGS. 5-8.

If desired, the dispenser 10 may also utilize the cover member 18 in the form of a cardboard sleeve, as is known the art. The cover member is designed to initially cover the applicator assembly 16 prior to activating the dispenser 10. The cover member 18 is dimensioned to fit snugly over the applicator assembly 16 and extend over a portion of the dispenser 10. One end of the cover member 18 may be closed although it is understood that both ends of the cover member 18 could be open ends. When preparing to activate the dispenser 10, the cover member 18 is removed from the dispenser 10. In certain prior art applications, an end of the dispenser 10 opposite of the applicator assembly 16 is inserted into the cover member 18. With the present invention as described in further detail below, the cover member 18 is not used during activation of the dispenser 10. As discussed, the cover member 18 is a cardboard or paper-based material in an exemplary embodiment. It is also understood that the dispenser 10 can incorporate an identifying label.

As shown in FIGS. 9-18, the present invention utilizes a dispenser actuator assembly generally designated with the reference numeral 100. The dispenser actuator assembly 100 may also be referred to as an ampoule actuator assembly 100 or dispenser/ampoule holder 100. As explained in greater detail below, the dispenser actuator assembly 100 cooperates with the dispenser 10 to actuate the dispenser 10. The structure of the dispenser actuator assembly 100 will first be described followed by a description of the cooperation and operation of the dispenser actuator assembly 100 with the dispenser 10.

As further shown in FIGS. 9-18, the dispenser actuator assembly 100 generally includes a base member 102 and an actuator assembly 104. The actuator assembly 104 is operably connected to the base member 102 as further described below.

FIGS. 9-16 show the base member 102 of the dispenser actuator assembly 100. The base member 102 is generally a rounded member that fits around at least a portion of the glass ampoule assembly 10. The base member 102 is further an annular member that in one exemplary embodiment is dimensioned to fit over the dispenser or glass ampoule assembly 10 as described in greater detail below.

The base member 102 generally includes an annular ring member 106 and a connector member 108. The annular ring member 106 is a full ring member in an exemplary embodiment that defines an opening 110 therethrough to receive the dispenser as explained in greater detail below. Thus, in an exemplary embodiment, the annular ring member 106 is dimensioned to fit circumjacently around the glass ampoule assembly and, in particular, the second container 14. It is understood that in other exemplary embodiments, the ring member 106 may not be a full ring member and have an interruption, slot or break in the member. The annular ring member 106 has an inner surface 112 that defines the opening 110. The inner surface 112 has a plurality of ribs 114 extending radially inwardly into the opening 110. In an exemplary embodiment, the ribs 114 extend axially or longitudinally along the inner surface 112 of the annular ring member 106. Furthermore, four ribs 114 are utilized and are spaced circumferentially on the inner surface 112 at 12 o'clock, 3 o'clock, 6 o'clock and 9 o'clock positions. It is further understood that a single rib 114 could be employed or other numbers of ribs 114, and further at other annular locations. The ribs 114 could also take the form of ribs extending circumferentially along the inner surface 112 of the annular ring member 106. The ribs 114 assist in providing an interference fit with the second container 14 of the glass ampoule assembly 10 when the base member 102 is mounted on the second container 14. The annular ring member 106 further has a flange 116 extending circumferentially around the ring member 106 at a proximate end of the ring member 106. The flange 116 assists in adding rigidity and strength to the proximal end of the base member 102. The added rigidity and strength provided by the flange 116 also helps when ejector pins push the base member 102 off of the mold member during the injection molding process.

FIGS. 9-16 further show the connector member 108 of the base member 102. The connector member 108 generally connects to the actuator assembly 104. The connector member 108 extends from a proximate end of the annular ring member 106 towards the actuator assembly 104. The connector member 108 has a first slot 118 or upper slot 118 defined therein as well as a second slot 120 or lower slot 120 defined therein. As a result, the connector member 108 has a first segment 122 and a second segment 124 defined between the first slot 118 and the second slot 120. The first segment 122 is positioned generally opposite to the second segment 124. The first slot 118 and the second slot 120 extend partially circumferentially having respective ends that confront in spaced relation to define the first segment 122 and the second segment 124. The first slot 118 and the second slot 120 are generally opposite to one another. As explained in greater detail below, the slots 118, 120 assist in the flexing of the actuator assembly 104, or pivoting movement of the actuator assembly 104. The first segment 122 has a first end connected to the base member 102 and a second end connected to the actuator assembly 104, or a flex plate of the actuator assembly to be described. The second segment 124 has a first end connected to the base member 102 and a second end connected to the actuator assembly 104, or a flex plate of the actuator assembly to be described. The second segment 124 has a second raised tab 126 positioned on a central portion of the first segment 122 and that extends from the flange 116 towards the actuator assembly 104 (or to a flex plate as described in greater detail below). Similarly, the second segment 124 has a second raised tab 128 positioned on a central portion of the second segment 122 and that extends from the flange 116 to the actuator assembly 104. The raised tabs 126, 128 assist in providing rigidity for an enhanced connection between the base member 102 and the actuator assembly 104. The rigidity provided by the raised tabs 126, 128 further help when ejector pins engage the base member 102 proximate the raised tabs 126, 128 to smoothly remove the assembly 100 from a mold member after formation in an injection molding process.

As shown in FIGS. 9-16, the base member 102 is formed as a full annular ring member in one exemplary embodiment. The base member 102 is designed to receive or hold the dispenser 10 or glass ampoule assembly 10, and it is understood that the base member 102 may not have a full ring-shaped configuration. For example, the base member 102 can have certain segments eliminated and not utilized while still having a configuration to receive or hold the glass ampoule assembly 10. The base member 102 could have a slot formed therein to define separate segments that may be resiliently flexible.

The base member 102 further defines the annular ring member 106 that defines the opening 110 for the glass ampoule assembly 10. The inner surface 112 of the base member 102 is tapered such that the entry of the base member is slightly larger at one end. In a particular exemplary embodiment, the base member 102 tapers to a larger dimension towards the actuator assembly 104. This provides for easier insertion of the glass ampoule assembly at that end. In one exemplary embodiment, there is a 2-degree taper of the inner surface 112. In other exemplary embodiments, the taper could be 1-3 degrees. It is further understood that the taper can be in an opposite direction as well. The outer container 14 of the glass ampoule assembly 10 may have a rounded end that also assists insertion/mounting between the dispenser actuator assembly 100 and the glass ampoule assembly 10.

FIGS. 9-16 further show the actuator assembly 104 of the dispenser actuator assembly 100. In one exemplary embodiment, the actuator assembly 104 generally includes a first actuator arm 132a and a second actuator arm 132b. As explained in greater detail below, the first actuator arm 132a and the second actuator arm 132b are connected to the base member 102 via the connector member 108 and, in particular, the first segment 122 and the second segment 124 of the connector member 108. It is understood that the first actuator arm 132a and the second actuator arm 132b are similar in structure and positioned generally symmetrically as described in greater detail below. The first actuator arm 132a and the second actuator arm 132b extend from the base 102 (or flex plate to be described) in generally opposed relation. It is also understood that description regarding the first actuator arm 132a will generally apply to the second actuator arm 132b. The structures of the first actuator arm 132a are referenced with an "a" designation while the structures of the second actuator arm 132b are referenced with a "b" designation.

FIGS. 9-16 further show the first actuator arm 132a. The first actuator arm 132a has a proximal end 134a, a distal end 136a and an intermediate segment 138a. The proximal end 134a is angled to be generally parallel to the flange 116. The proximal end 134a is connected to the first segment 122 of the connector member 108 and the second segment 124 of the connector member 108. As shown further in FIGS. 9 and 10, the intermediate segment 138a defines a floor segment 140a and an outer peripheral flange 142a. The floor segment 140a is recessed with respect to the outer peripheral flange 142a. The intermediate segment 138a has a plurality of apertures 144a extending into the first actuator arm 132a proximate the proximal end 134a. In an exemplary embodiment, the apertures 144a do not extend entirely through the arm 132a. The apertures 144a assist in removing certain material in the formation of the assembly 100 to avoid having large block of material associated with the assembly 100 which is generally undesirable in an injection molding process used to form the assembly 100. The apertures 144a further define additional walls to add further rigidity and strength to the assembly 100. The floor segment 140a further has a finger pad 146a in the form of a plurality of raised ridges 148a. The recessed features of the floor and ridges with respect the flange provide for a tactile feel for the user for more proper finger/digit placement, as well as helping to maintain engagement of the fingers/digits with the actuator arms 132a, 132b. It is understood that the structures of the first actuator arm 132a apply to the second actuator arm 132b with the "b" designations.

As shown in FIGS. 9-22, the first actuator arm 132a further has a depending protrusion 150a positioned on an underside of the first actuator arm 132a. The depending protrusion 150a has a first segment 152a and a second segment 154a. The first segment 152a defines a platform 156a proximate to the proximal end of the first actuator arm 132a. The second segment 154a extends from the first segment 152a at an interface edge 158a. The interface edge 158a may be considered as defining a lined projection to be described in greater detail below. The lined projection is useful in providing a concentrated force against the glass ampoule assembly 10 as described in greater detail below. The second segment 154a has a plurality of channels 160a defined therein wherein the second segment 154a defines a plurality of spaced walls 162a. In an exemplary embodiment, the second segment 154a has a pair of channels 160a that define three spaced walls 162a. The walls 162a add stiffness to the actuator arm 132a. The second segment 154 and the walls 162a are dimensioned such that they follow the extension of the first actuator arm 132a. The second segment 154a inclines upward towards the distal end 136a of the arm 132a, thus the second segment 154a defines an inclined surface. As explained in greater detail below, this configuration allows the second segment 154 to be generally parallel to a longitudinal axis of the glass ampoule assembly 10 when a user manipulates material from the assembly 10 by further squeezing the actuator arm 132a. With the walls 162a depending from an underside surface of the floor segment 140a of the actuator arm 132a, the actuator arm 132a is designed similar to an I-beam wherein the structure provides strength, rigidity and stiffness to the actuator arm 132a. The walls 162 depend from an underside surface of the actuator arm 132a. The top of the actuator arm 132a remote from the proximal end remains a solid structure without openings to provide tactile feel while the spaced walls 162a provide strength etc. to the actuator arm 132a.

As shown in FIG. 15, a boss 164a is defined at a distal end of the second segment 154a of the depending protrusion 152a. In an exemplary embodiment, a boss 164a is defined at the distal end of each spaced wall 162a. The boss 164a is configured to be engaged by ejector pins in ejecting the molded part from a mold during an injection molding process used to form the dispenser actuator assembly 100 as described in greater detail below. As further shown in FIGS. 15 and 16, an indentation 166a, or indentation slot 166a is defined in the actuator arms 132a adjacent the bosses 164a. The indentation 166a is generally defined between an underside surface of the actuator arm 132a and the boss 164a. As described in greater detail below, during the injection molding process used to form the assembly 100, fingers defined in the mold part extend into the mold cavity to define the indentations 166a. The fingers will maintain the actuator arms 132a, 132b against an internal mold part until ejector pins can engage the bosses 164a. This minimizes the chance for the actuator arms 132a, 132b to prematurely come off of the internal mold piece which could affect later operation of the assembly. The shape of the second segment 154a allows the second segment 154a to manipulate the glass ampoule assembly 10 to provide an enhanced pumping action to expel more fully the flowable material M from the glass ampoule assembly. As discussed, the above description of the structure of the first actuator arm 132a is applicable for the structure of the second actuator arm 132b and having "b" designations.

The dispenser actuator assembly 100 is used with a dispenser 10 such as the glass ampoule assembly 10 to crush the glass ampoule assembly 10 and dispense flowable material from the glass ampoule assembly 10. As can be appreciated from FIG. 8, the glass ampoule assembly 10 is prepared such as by removing a cardboard sleeve if the sleeve is being used or removing the glass ampoule assembly 10 from any blister packaging. Alternatively, the glass ampoule assembly 10 may use the cover member 18 which is removed in preparation for dispensing flowable material from the glass ampoule assembly 10. As can be appreciated from FIGS. 29-34, the glass ampoule assembly 10 is inserted into the base member 102. The opening 110 defined by the base member 102 receives the glass ampoule assembly 10 wherein the base member 102 slides onto the second container 14. Thus, the actuator assembly 100 is slidably movable along the second container 14. In one exemplary embodiment, the base member 102 slides onto the second container 14 in a frictional interference fit. The ribs 114 assist in engaging the outer surface of the outer container 14 of the glass ampoule assembly 10 to achieve a snug interference fit. In one exemplary embodiment, the glass ampoule assembly 10 is inserted into a distal end of the base member 102 opposite the flange 116. Even if the taper is such that the distal end of the base member 102 is more narrow, the outer container 14 of the glass ampoule assembly 10 has a rounded edge that assists in smooth insertion/ mounting. It is also understood that the dispenser actuator assembly 10 could also be slid over the glass ampoule assembly 10 at the proximal end of the base member 102. Regardless of the insertion, the actuator arms 132a, 132b extend away from the applicator 16 of the ampoule assembly 10.

Figure 29:
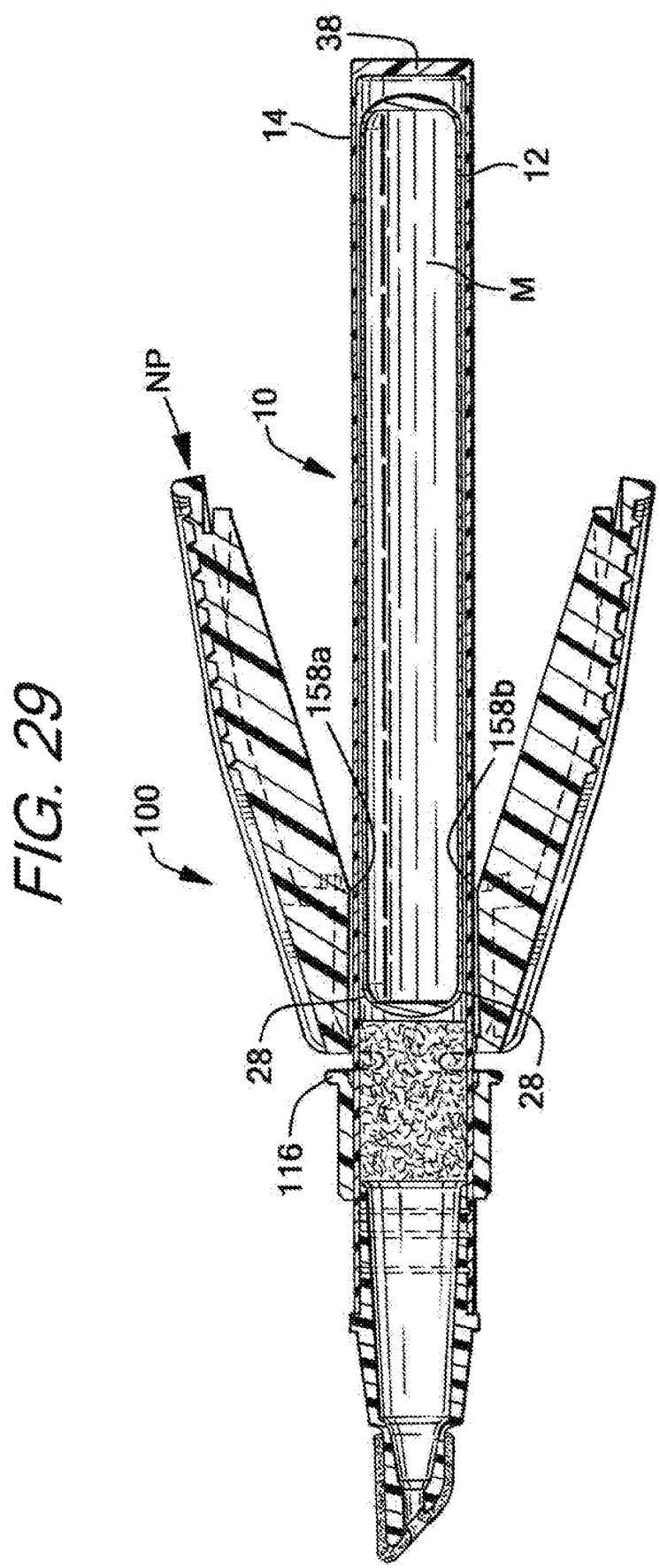
FIG. 29 is a side cross-sectional view of the dispenser actuator assembly mounted on the dispenser in the form of a glass ampoule assembly of FIG. 1.
Figure 30:
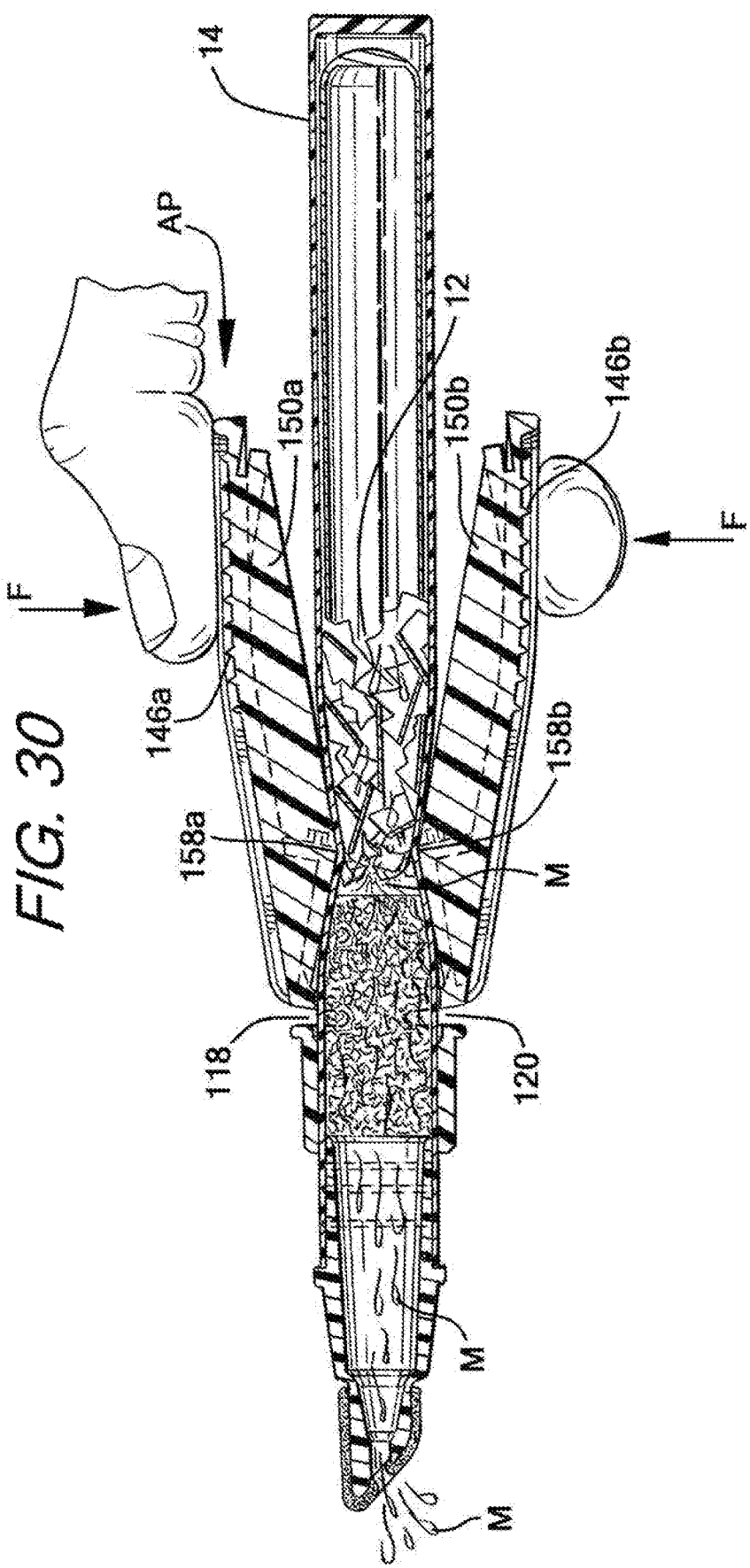
FIG. 30 is a side cross-sectional view of the dispenser actuator assembly mounted on the dispenser and showing actuation of the dispenser actuator assembly wherein a glass ampoule in the dispenser is fractured.

As further shown in FIGS. 29-30, when the dispenser actuator assembly 100 is properly located on the glass ampoule assembly, the first depending protrusion 150*a* and the second depending protrusion 150*b* are positioned proximate the first interface area 28 of the glass ampoule 12. In particular, the interface edge 158*a* of the first depending protrusion 150*a* and the interface edge 158*b* of the second depending protrusion 150*b* are positioned at the first interface area of the first container 12 of the glass ampoule assembly 10. In addition, the first actuator arm 132*a* and the second actuator arm 132*b* extend towards the closed end 38 of the second container 14 of the glass ampoule assembly 10.

It is understood that the one of the dispenser actuator assembly 100 and the glass ampoule assembly 10 could have a locating structure thereon to properly position the dispenser actuator assembly 100 on the glass ampoule assembly 10 so that the actuator arms 132*a*, 132*b* are properly positioned to crush the glass ampoule 12. The location structure can also take the form of a cooperative structure on one of or both of the dispenser actuator assembly 100 and the glass ampoule assembly 10. For example, the second container 14 of the glass ampoule assembly 10 could have an annular, radially-inwardly formed indentation that the base member 102 is received therein to automatically locate the dispenser actuator assembly 100 on the proper location on the glass ampoule assembly 10. Similarly, an outwardly extending protrusion could be located on the second container wherein the base member 102 slides over the protrusion until the actuator assembly 100 fits adjacent the protrusion to be properly located. Multiple protrusions could also be used such as outwardly extending spaced protrusions wherein the actuator assembly 100 fits within spaced protrusions to be properly located.

FIGS. 29 and 30 show the dispenser actuator assembly 100 positioned on and operably connected to the glass ampoule assembly 10. The glass ampoule assembly 10 is now ready to be actuated. The first container 12, or glass ampoule 12, is in a position to be crushed wherein the flowable material M can be dispensed from the assembly 10. As further shown in FIG. 29, the first depending protrusion 150*a* of the first actuator arm 132*a* and the second depending protrusion 150*b* of the second actuator arm 132*b* are spaced from the second container 14 and positioned over and proximate the first interface area 28. Thus, a gap or space is initially maintained between the protrusions 130*a*, 130*b* and the second container 14. In such position as shown in FIG. 29, the actuator arms 132*a*, 132*b* are in a first position, or first neutral position NP.

As can be further appreciated from FIGS. 29-30, a user holds the dispenser actuator assembly 100 wherein a forefinger wraps around an underside of the base member 102 and engages the second actuator arm 132*b*. A thumb of the user engages the first actuator arm 132*a*. In particular, a user's forefinger and thumb engage the respective finger pads 146*a*, 146*b* of the first actuator arm 132*a* and the second actuator arm 132*b*. The user squeezes the actuator assembly 100 thereby applying a compressive force F (FIG. 30) to the first actuator arm 132*a* and the second actuator arm 132*b*. Thus, the actuator arms 132*a*, 132*b* are pivotable about the base 102 from the first neutral position to a second position or an actuating position AP. In response to this compressive force, the depending protrusion 150*a* of the first actuator arm 132*a* is deflected towards and engages the second container 14 and the depending protrusion 150*b* of the second actuator arm 132*b* is deflected towards and engages the second container 14. As the user continues to depress the first actuator arm 132*a* and the second actuator arm 132*b*, the depending protrusion 150*a* of the first actuator arm 132*a* deflects the second container 14 wherein the second container 14 engages the glass ampoule 12 at proximate a top or upper portion of the first interface area 28, and the depending protrusion 150*b* of the second actuator arm 132*b* deflects the second container 14 wherein the second container 14 engages the glass ampoule 12 at proximate a bottom or lower portion of the first interface area 28 (e.g. opposite ends of the first interface area 28), wherein the glass ampoule 12 is crushed at the first interface area 28. In particular, it is understood that the first interface area 28 is engaged by the protrusion interface edge 158*a*, 158*b* (ridge) of the protrusions 150*a*, 150*b* of the actuator arms 132*a*, 132*b*. The protrusion interface edges 158*a*, 158*b* assist in concentrating the force F onto the outer container 14 and glass ampoule 12.

It is further understood that the first slot 118 or upper slot 118 and the second slot 120 or lower slot 120 assist on providing sufficient flexibility for the actuator arms 132*a*, 132*b*. As the slots 118, 120 separate the actuator arms 132*a*, 132*b* from the base member 102, the actuator arms 132*a*, 132*b* can pivot independently from the base member 102. This allows the base member 102 to continue to provide support for holding the glass ampoule assembly 10 independently of the pivoting of the actuator arms 132*a*, 132*b*. It is further understood that the actuator arms 132*a*, 132*b* themselves do not generally bend or flex as the arms 132*a*, 132*b* are more rigid, but the arms 132*a*, 132*b* flex or pivot. Upon crushing or rupture, the flowable material M passes from the glass ampoule 12 and into the applicator 16. Because force F is applied to the glass ampoule 12 at the first interface area 28, the domed portion of the glass ampoule 12 breaks into multiple pieces allowing enhanced flow of the flowable material M out of the glass ampoule 12 and into the second container 14 and to the applicator assembly 16. It has been determined by the inventors that if the glass ampoule 12 is crushed at the interface area 28, the domed-section will break into multiple pieces rather than remaining intact while breaking away from the intermediate section of the glass ampoule 12. The flowable material M passes from the second container 14 and into the applicator assembly 16. FIGS. 31 and 32 disclose partial views of the actuation of the glass ampoule assembly 10 wherein the depending protrusions 150*a*, 150*b* of the first and second actuator arms 132*a*, 132*b* engage the second container 14 of the glass ampoule assembly 10.

As further can be appreciated from FIGS. 30 and 33, the user can continue to squeeze the actuator assembly 100 wherein the user engages the first actuator arm 132*a* and the second actuator arm 132*b* thereby continuing to apply the compressive force F wherein the depending protrusions 150*a*, 150*b* are further deflected towards and engage the second container 14. As the user continues to depress first and second actuator arms 132*a*, 132*b*, the respective second segments 154*a*, 154*b* of the protrusions 150*a*, 150*b* deflect the second container 14 wherein the second container 14 engages the glass ampoule 12 further along the glass ampoule 12. In this configuration such as shown in FIG. 33, the respective segments 154*a*, 154*b* are generally positioned parallel to one another. In certain embodiments, the glass ampoule 12 may be sized such that the respective second segments 154*a*, 154*b* can be positioned at proximate the second interface area 30 wherein the glass ampoule 12 further ruptures. Upon this additional rupture, the flowable material M more easily passes from the glass ampoule 12 and into the second container 14 and into the applicator 16.

Because force F is applied to the glass ampoule 12 at the second interface area 30, the domed portion of the glass ampoule 12 breaks into multiple pieces allowing enhanced flow of the flowable material M out of the glass ampoule 12 and into the second container 14 and to the applicator assembly 16. It is further understood that the user can use the actuator arms 132a, 132b and second segments 154a, 154b to further deflect and manipulate the second container 14 and force the flowable material M through the applicator assembly 16 and, therefore, to enhance dispensing of the flowable material M from the glass ampoule assembly 10.

It is understood that the applicator assembly 16 assists in minimizing the chance of glass shards from the ruptured glass ampoule 12 from passing out of the glass ampoule assembly 10. In addition, the outer wall of the second container 14 prevents glass shards from cutting fingers of the user thereby protecting the user's fingers from injury by the fractionated glass shards of the glass ampoule 12 that remain in the second container 14. Because a user engages the actuator assembly 100 to crush the glass ampoule assembly 10 rather than engaging the glass ampoule assembly 10 directly, the chance of cutting a user's fingers/thumb from glass shards is further minimized. It is understood that additional structures could be incorporated into the glass ampoule assembly 10 such as filter assemblies 44 to minimize the chance of glass shards from passing through the applicator assembly. As shown in FIG. 34, the flowable material M can be dispensed from the glass ampoule assembly 10 and onto a receiving surface. The receiving surface S can vary depending the particular type of flowable material M being dispensed. In one exemplary embodiment, the flowable material M may be a medicine that is dispensed onto a skin surface S of a patient.

As further appreciated from the figures, the user dispenses the flowable material M from the glass ampoule assembly 10 with the aid of the dispenser actuator assembly 10. Once the flowable material M is emptied from the glass ampoule assembly 10, the dispenser actuator assembly 100 can be removed from the glass ampoule assembly 10. In this fashion, the dispenser actuator assembly 10 can be reused with multiple dispenser assemblies 10 or glass ampoule assemblies 10. In this configuration, the dispenser actuator assembly 100 can be formed from a more robust and higher-cost material. In other configurations, the material used to form the dispenser actuator assembly 100 could be a lower cost material that is designed as a one-time use wherein the dispenser actuator assembly 100 is disposable. In such case, the location structured used to position the dispenser actuator assembly 100 on the glass ampoule assembly 10 could be structured to permanently attach the dispenser actuator assembly 100 to the glass ampoule assembly 10. Once the flowable material M is fully dispensed from the glass ampoule assembly, the attached structures can be simply discarded together.

It is understood that the dispenser actuator assembly 100 can be formed in an injection molding process to form a unitary one-piece member. A wide variety of materials can be used to form the dispenser actuator assembly 100 wherein the actuator arms 132a, 132b are resiliently pivotable to actuate the glass ampoule assembly and then be reused on additional glass ampoule assemblies. As discussed, it is understood that in an exemplary embodiment, the actuator arms 132a, 132b are generally rigid and do not bend or flex themselves, but rather pivot about the connector members or in relation to the base member 102. Similarly, the depending protrusions 150a, 150b are rigid and do flex themselves. In an exemplary embodiment, the dispenser actuator assembly is made from one of the polyolefin family of resins.

As discussed herein, the dispenser actuator assembly 100 has been described herein as having a base member 102 and an actuator assembly 104 having a first actuator arm 132a and a second actuator arm 132b. A connector member 108 has been described that connects the base member 102 and the actuator assembly 104. It is understood that the actuator arms 132a, 132b pivot towards one another, and pivot with respect to the base member 102 and connector member 108. It is understood that the assembly 100 could also be considered that the first actuator arm 132a and the second actuator arm 132b are connected by a central hub member 180 or flex plate 180, or torsion plate 180. In particular, a proximal end 134a of the first actuator arm 132a is connected to a top portion or first end of the flex plate 180, and a proximal end 134b of the second actuator arm 132b is connected to a bottom portion or second end of the flex plate 180. The first end of the flex plate 180 is generally opposite to the second end of the flex plate 180. In one exemplary embodiment, the flex plate 180 is then considered to be part of the actuator assembly 104. The flex plate 180 is generally connected between the actuator arms 132a, 132b and, as discussed, the first end, or upper end of the flex plate 180 is connected to the proximal end 134a of the first actuator arm 132a, and an opposite second end, or lower end of the flex plate 180 is connected to the proximal end 134b of the second actuator arm 132b. In this configuration, the base member 102 is still operably connected to the actuator assembly 104 by the connector member 108. The flex plate 180 serves as a transition structure from the base member 102 to the actuator arms 132a, 132b.

FIG. 18 shows the flex plate 180 in greater detail. The flex plate 180 has a central portion 182 and a first side rail 184 and a second side rail 186, generally opposite the first side rail 184. The central portion 182 of the flex plate 180 has an opening 188 therethrough. The flex plate opening 188 is generally aligned with the opening 110 of the base member 102 as further described below. The flex plate opening 188 may be slightly larger than the opening 110 of the base member 102 or the same size. Thus, the flex plate opening has a diameter larger than a diameter of the opening of the base member 102. The central portion 182 further has a first flexion segment 190 or upper flexion section 190, and a second flexion segment 192 or lower flexion segment 192 as further described below. An upper portion of the first flexion segment 190 is adjacent the proximal end 134a of the first actuator arm 132a at a first connection line 194, generally at the first end of the flex plate 180. A bottom portion of the second flexion segment 192 is adjacent the proximal end 134b of the second actuator arm 132b at a second connection line 196, generally at the second end of the flex plate 180. As further shown in FIG. 18, the central portion 182 of the flex plate 180, including the first flexion segment 190 and the second flexion segment 192, have a lesser thickness than the thickness of the first side rail 184 and the second side rail 186. As further shown in FIGS. 29 and 33, it is understood that the first flexion segment 190 is positioned generally between a midpoint of the vertical length of the flex plate 180 and the location where the first actuator arm 132a is connected to the flex plate 180. Similarly, the second flexion segment 192 is positioned generally between a midpoint of the vertical length of the flex plate 180 and the location where the second actuator arm 132b is connected to the flex plate 180. The flex plate 180 generally flexes or bends at positions between where the connector member 108 connects to the flex plate (the first segment 122 and the second segment 124) and where the actuator arms 132a, 132b connect to the flex plate 180. As discussed, the first slot 118 is defined between the first end of the flex plate 180 and the base 102. The second slot 120 is defined between the second end of the flex plate 180 and the base 102.

As can be further appreciated from FIG. 18, the flex plate 180 is connected to the first actuator arm 132a and the second actuator arm 132b. In this exemplary embodiment of the invention, the flex plate 180 and the first actuator arm 132a and the second actuator arm 132b define the actuator assembly 104. The upper portion of the first flexion segment 190 and upper portions of the first and second side rails 184, 186 are connected to the proximal end 134a of the first actuator arm 132a at the first connection line 194. Similarly, the lower portion of the second flexion segment 192 and lower portions of the first and second side rails 184, 186 are connected to the proximal end 134b of the second actuator arm 132b. As further shown in FIG. 18, the first segment 122 of the connector member 108 is connected to the central portion of the flex plate 180 and also to the base 102. Thus, the first segment 122 has a first end connected to the base 102 and a second end connected to the flex plate 180. The first raised tab 126 is connected to the first side rail 184 and also connected to the flange 116 of the base 102. The second segment 124 of the connector member 108 is connected to the central portion of the flex plate 180 and also to the base 102. Thus, the second segment 124 has a first end connected to the base 102 and a second end connected to the flex plate 180. The second raised tab 128 is connected to the second side rail 186 and also to the flange 116 of the base 102. With these connections, the flex plate opening 188 is generally aligned with the opening 110 of the base member 102. Accordingly, the connector member 108 operably connects the base member 102 to the actuator assembly 104. As discussed, the segments 122, 124 of the connector member 108 are connected to the flex plate 180. It is further understood that the flex plate 180 could have location structures thereon to properly position the dispenser actuator assembly 100 on the glass ampoule assembly 10. It can further be appreciated from FIGS. 18 and 31, for example, that the flex plate 180 is dimensioned to extend beyond the outer periphery of the base member 102.

As previously discussed and as shown in FIGS. 17 and 29, the dispenser actuator assembly 100 is mounted on the glass ampoule assembly 10 and in a position wherein the protrusions 150, 152 can crush the glass ampoule 12. This configuration may be considered the first position or neutral position. In this configuration, the flex plate 180 is unflexed and is generally in a planar configuration such as shown in FIGS. 17 and 29. Similar to the description above, a user engages the first actuator arm 132a and the second actuator arm 132b and applies a force F wherein the arms 132a, 132b are forced towards one another. Thus, the arms 132a, 132b move from the first neutral position to an actuating position AP. The flex plate 180 flexes generally at the first flexion segment 190 and the second flexion segment 192. This flexion of the flex plate 180 is shown in FIGS. 30-33. The first flexion segment 190 and the second flexion segment 192 provides for flexion over a greater radius, which lessens the stress on the assembly 100. If the actuator arms 132a, 132b pivoted specifically at, for example, the first connection line 194 and the second connection line 196, stresses are more locally focused at a smaller area, which is undesirable as it can promote plastic deformation of the material. The first flexion segment 190 and the second flexion segment 192 provide elastic deformation of the flex plate 180, which allows the flex plate 180 to return to its first or neutral position NP. Thus, the flex plate 180 is resiliently deflectable. FIG. 31 shows the flexion of the first flexion segment 190 and the second flexion segment 192 represented by the angular configuration "A" and which further provides for the majority of the flexing of the flex plate 180. Additional arrows A in FIG. 31 further show the flexion of the flex plate 180. It is understood that the actuator arms 132a, 132b are generally more rigid and do not pivot around the first connection line 194 and the second connection line 196. The flexion is concentrated at the flex plate 180 as shown.

As further shown in FIG. 33, a user can continue to press the actuator arms 132a, 132b to manipulate flowable material from the glass ampoule assembly 100 wherein the second segments 154a, 154b of the actuator arms 132a, 132b are configured to be generally parallel to one another to further deform the outer container 14 of the glass ampoule assembly 10. Furthermore, the walls 162a, 162b engage the outer container 14 and further manipulate the glass ampoule 12 wherein the walls 162a, 162b are generally parallel to the longitudinal axis of the glass ampoule assembly 100. It is further understood that the dispenser actuator assembly 10 can be slid along the outer container 14 to reposition the assembly 10 and further manipulate the outer container 14 with the second segments 154a, 154b to expel flowable material M from the assembly 10.

The base member 102 utilizing the slots 118, 120 or the flex plate 180 and slots 118, 120 provides structural and functional advantageous features. As discussed, the actuator arms 132a, 132b do not pivot or flex towards one another at a specific point or location. The flex plate 180 flexes as shown in FIGS. 30-33 and such flexing occurs over a greater distance, e.g., a more substantial distance associated with the flex plate 180. In particular, much of the bending or flexing occurs at the first flexion segment 190 and the second flexion segment 192. This distributes stresses associated with the flexing over a greater distance on the flex plate 180 as opposed to a flexing configuration at a point such as a living hinge. With flexing and distributed stresses over a greater distance, any breaking point is minimized wherein the material of the assembly 100 is not pushed past its elastic limits. This allows the actuator arms 132a, 132b to return to the first or neutral position NP wherein the assembly 100 can be used with further glass ampoule assemblies 10. If the flexing structure was a living hinge structure, force would be focused at a more localized point, which would promote a failure or breaking of the actuator arm 132a, 132b from the base member 102. This configuration further provides for substantially rigid actuator arms 132a, 132b that have little flexing from the arms 132a, 132b themselves. While the material of the actuator arms 132a, 132b provide for minimal flexing, the flex plate 180 flexes to allow the substantially rigid actuator arms 132a, 132b to pivot or move towards one another, which allows for the depending protrusions 150a, 150b to provide a more direct, localized force to the glass ampoule assembly 10. This configuration also provides for flexing/movement of the actuator arms 132a, 132b independently of the support of the outer container 14 by the base member 102. The base member 102 supports the outer container 14 of the glass ampoule assembly 10 as the outer container 14 is inserted through the base member 102. With the slots 118,120 and the flex plate 180, the actuator arms 132a, 132b pivot via the flexing of the flex plate 180, which is independent of the support the base member 102 provides to the outer container 14. In other designs where wings or arms project directly from or an integral connection to a base, the base member can distort or deform in response to the movement of the arms 132a, 132b. As a result, the support for the ampoule assembly 10 can be lessened, altered or otherwise adversely affected. With the present design, the support of the glass ampoule assembly 10 by the base member 102 is isolated from the actuator arms 132a, 132b and not affected by the movement of the actuator arms 132a, 132b.

Finally, the structural features of the flex plate 180 and actuator arms 132a, 132b minimize unwanted lateral movement of the actuator arms 132a, 132b. The actuator arms 132a, 132b are connected laterally across the entire lateral dimension of the flex plate 180, e.g., the first and second connection lines 194, 196, which connection generally resists lateral movement of the actuator arms 132a, 132b. Minimizing any lateral movement of the actuator arms 132a, 132b is desirable as it can affect the proper crush of the glass ampoule 12 as the protrusion 150a, 150b may slip to the side of the glass ampoule 12 preventing crushing. As shown in FIG. 13, the base member 12 supports the glass ampoule assembly 10 across a lateral distance "a" that may generally correspond to a diameter of the glass ampoule assembly 10, e.g. a diameter dimension. The actuator arms 132a, 132b are connected along connection lines 194, 196 across a lateral dimension "b" that is greater than the diameter dimension "a." Thus, the lateral dimension of the flex plate 180 extends beyond the diameter of the glass ampoule assembly 10. With a greater dimension "b", the actuator arms 132a, 132b move towards the glass ampoule assembly in a generally perpendicular or normal direction to the elongated longitudinal axis L (FIG. 33) of the glass ampoule assembly 10. These structural and functional features of the dispenser actuator assembly 100 provide benefits over prior assemblies.

Figure 24A:
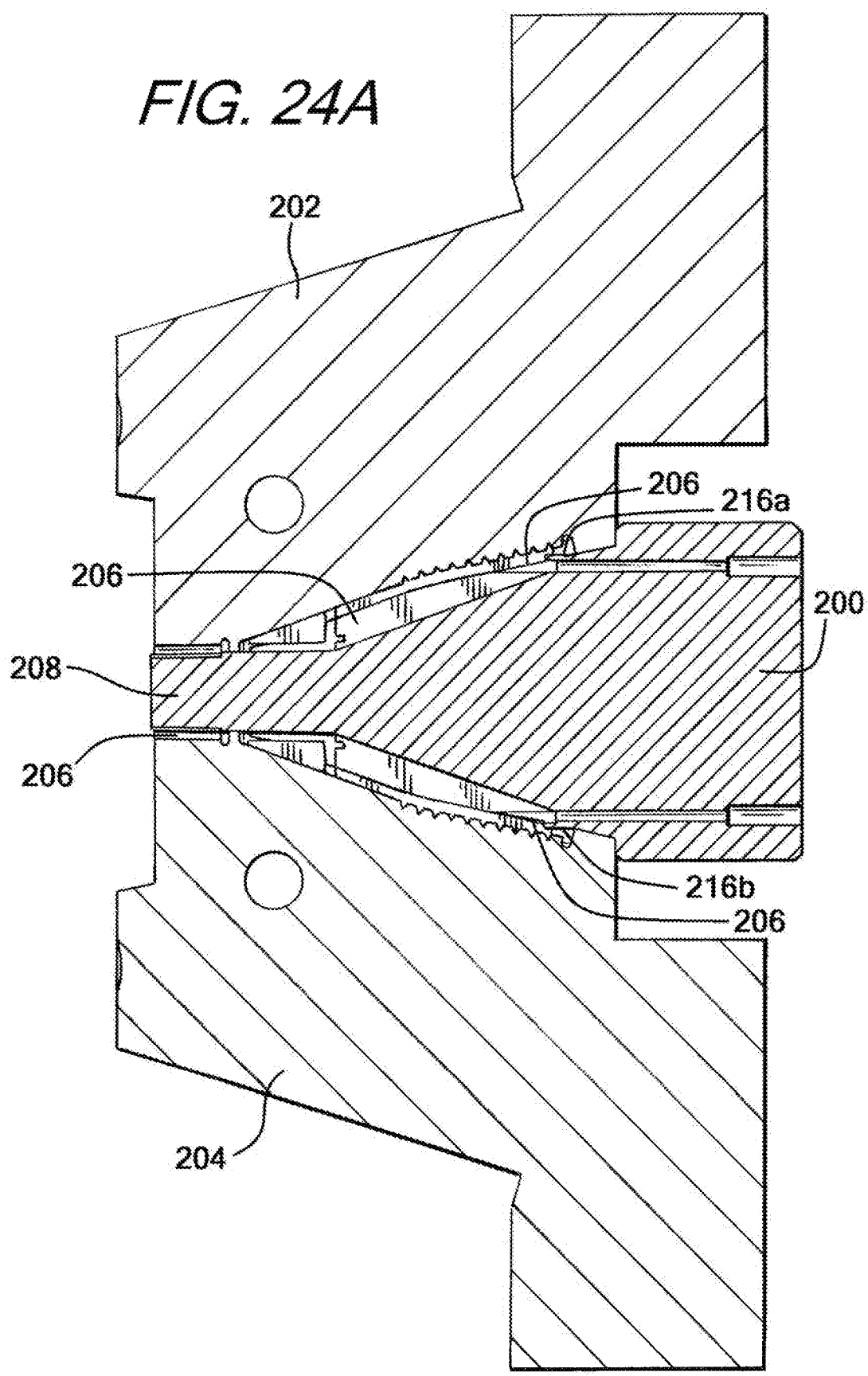
FIG. 24A is a side cross-sectional view of the core mold member and additional mold members defining a mold cavity corresponding to the dispenser actuator assembly of FIG. 9.
Figure 24B:
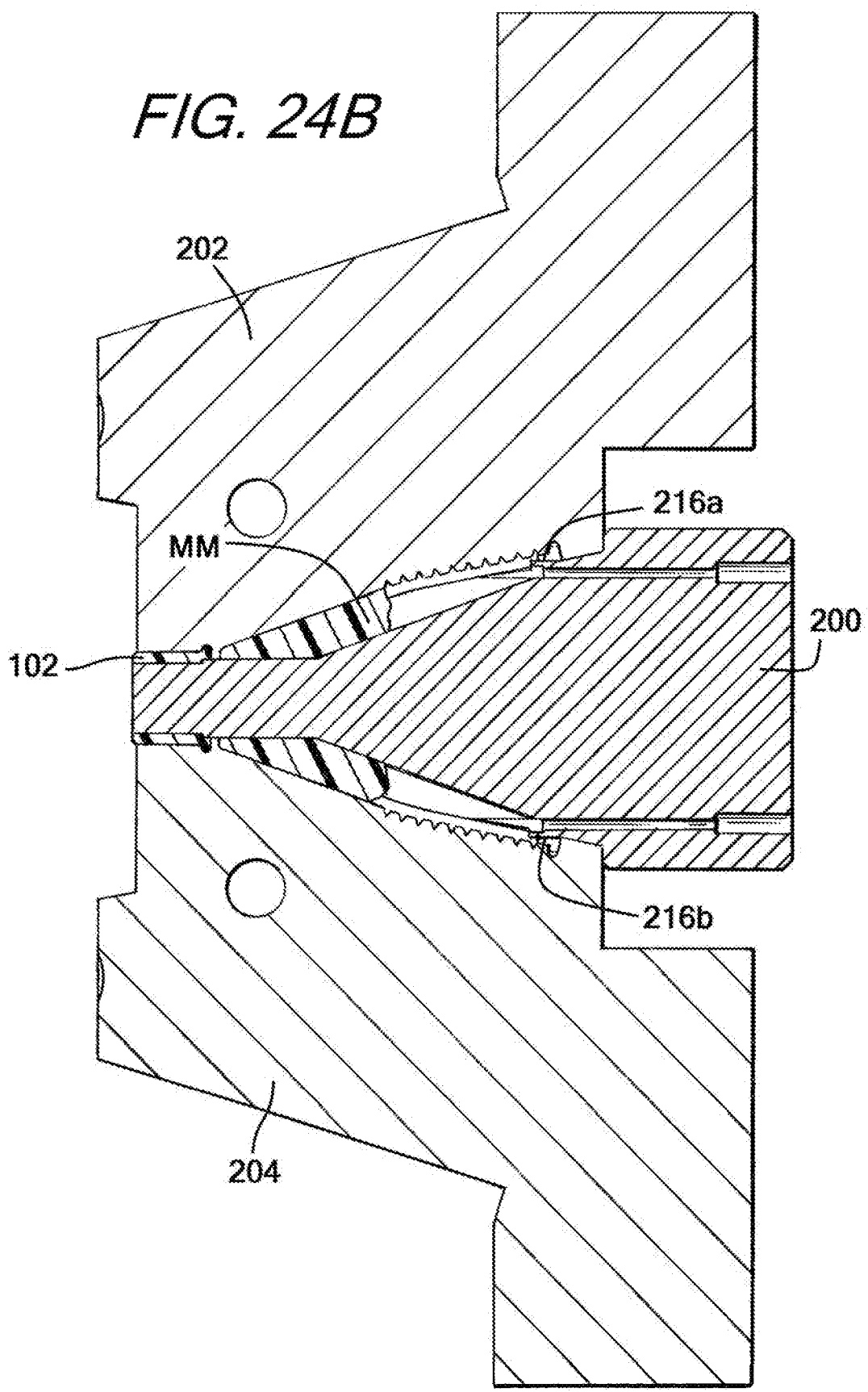
FIG. 24B is a side cross-sectional view of the core mold member and additional mold members of FIGS. 24B with injected material moving through a portion of the mold cavity.
Figure 25:
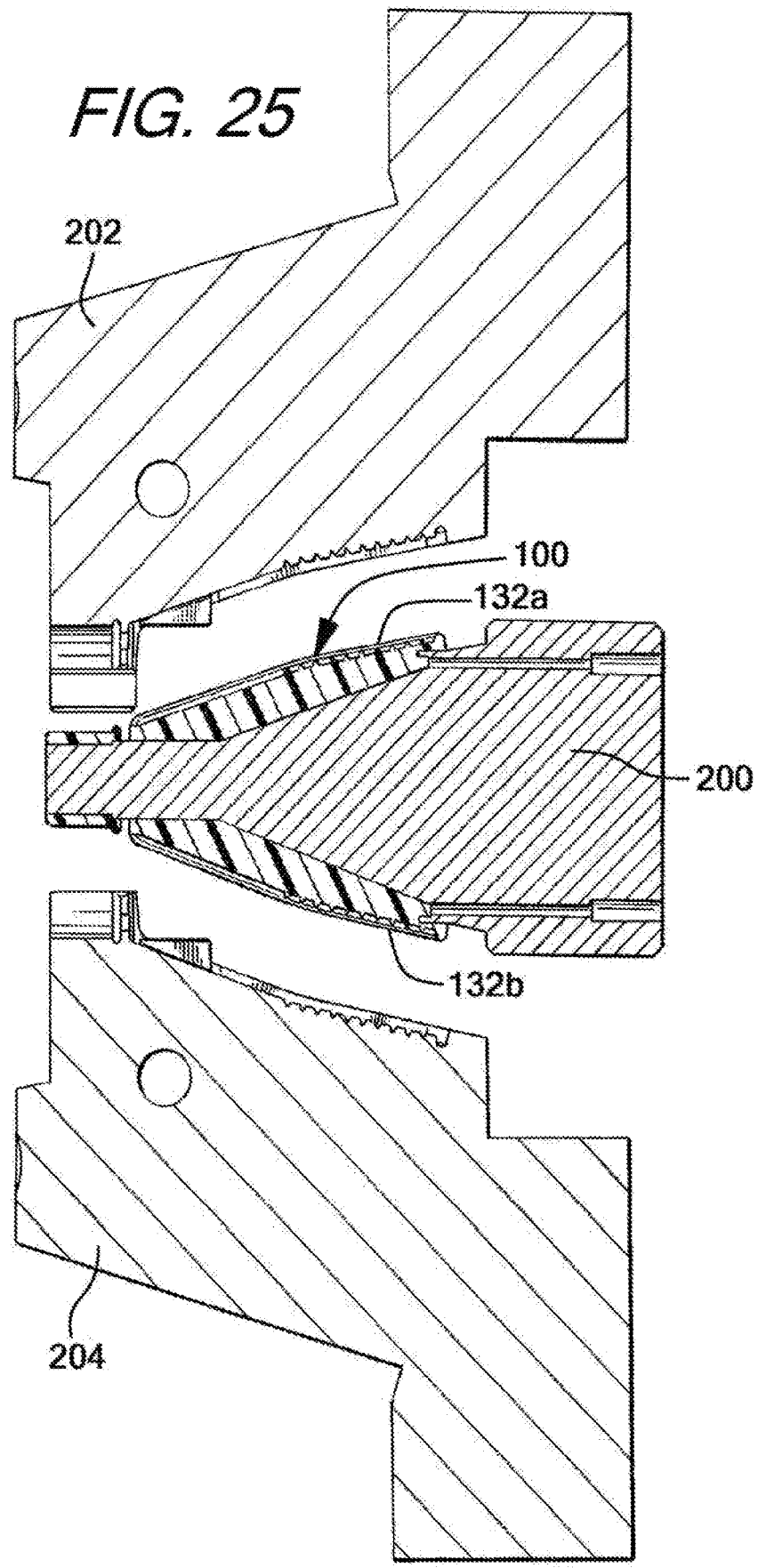
FIG. 25 is a side cross-sectional view of the core mold member and additional mold members wherein the mold members are separated and wherein the dispenser actuator assembly is on the core mold member.

As discussed, in an exemplary embodiment, the dispenser actuator assembly 100 is formed as a single unit in an injection molding process. FIGS. 19-28B disclose multiple mold members used to injection mold the dispenser actuator assembly 100. FIGS. 19-23 disclose a core mold member 200 used in making the dispenser actuator assembly 100. FIGS. 24-25 show an upper mold member 202 and a lower mold member 204. The core mold member 200, the upper mold member 202 and the lower mold member 204 are positioned in adjacent spaced relation to cooperate to define and form a mold cavity 206 (FIG. 24A) to receive the injected molded material. It is understood that additional mold members can be used as well as other structures and mechanisms such as gates known in the art of injection molding.

FIGS. 19-22 show the core mold member 200. The core mold member 200 has a central post 208 extending from a main body 210 having inclined surfaces 212 each having slotted indentations 214. The central post 208 helps form the base member 102 and the slotted indentations 186 help form portions of the actuator assembly 104. The central post 208 has channels 209 therein corresponding to the longitudinal ribs 114 on the base 102. It is understood that the central post 208 may be designed to be screwed into the main body 210 or otherwise removably attached to the main body 210. In such design, the central post 208 can comprise multiple types of central posts 208 each having channels 209 of different depths. In such case, the longitudinal ribs 114 can be made of varying sizes to accommodate differently-sized glass ampoule assemblies 10. The main body 210 has certain openings or conduits through the body 210 used to assist in ejecting the form part at the end of the injection molding process. As shown in FIG. 23, the main body 210 has pair of finger projections 216a, 216b that extend toward the central post 208.

FIGS. 24-25 further show the upper mold member 202 and the lower mold member 204. The mold members 202, 204 are positioned adjacent and in spaced relation to the core mold member 200 to define the mold cavity 206. It is understood that the mold members 200-204 cooperate to correspond to surfaces of the dispenser actuator assembly 100. For example, the core mold member 200 and portions of the upper mold member 202 and the lower mold member 204 cooperate to define the first and second actuator arms 132a, 132b. The finger projections 216a, 216b on the core mold member 200 extend into the mold cavity 206.

As discussed, the mold members 200, 202, 204 cooperate with a gate that receives a source of injection molded material and delivers the material into the mold cavity 206. FIG. 24B schematically shows molded material MM in the process of being injected into the mold cavity 206. It is understood that the molded material MM is injected into the entire mold cavity 206 to form the dispenser actuator assembly 100. It is understood that the molded material MM cools and hardens in the mold cavity 206 wherein the dispenser actuator assembly 100 is formed. Once formed and properly cooled, the dispenser actuator assembly 100 can be removed from the mold.

Figure 26:
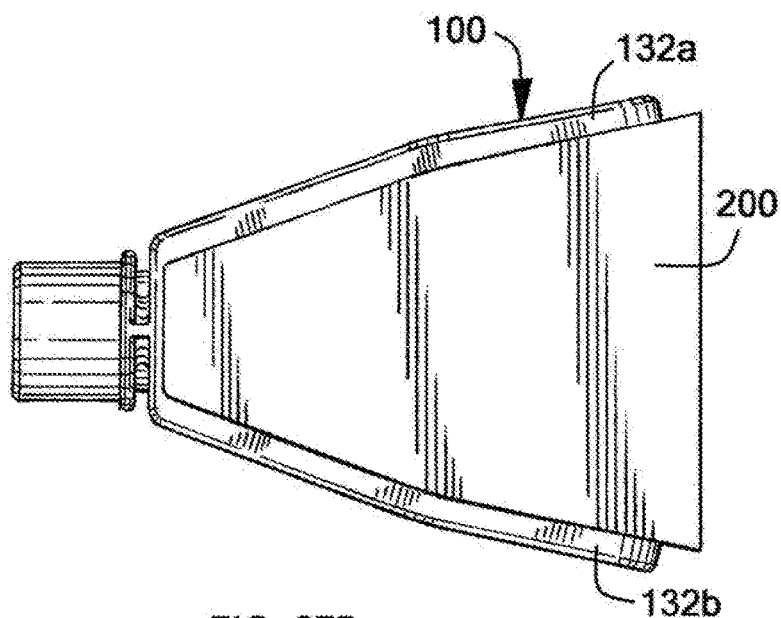
FIG. 26 is a side view of the dispenser actuator assembly post-molding on the core mold member.
Figure 27A:
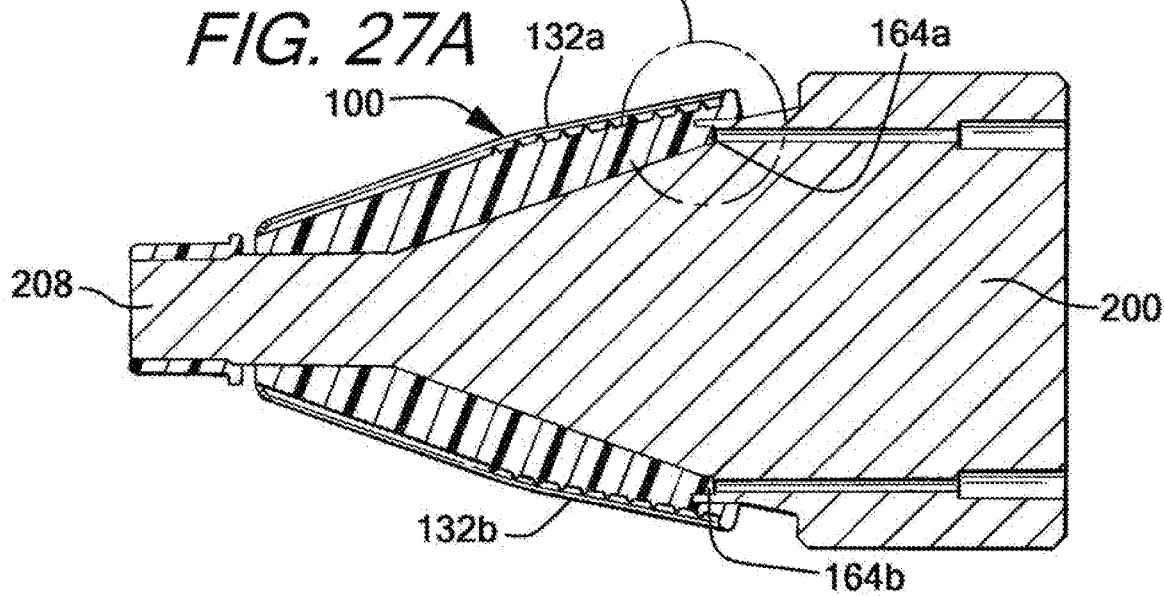
FIG. 27A is a cross-sectional view of the dispenser actuator assembly on the core mold member.
Figure 27B:
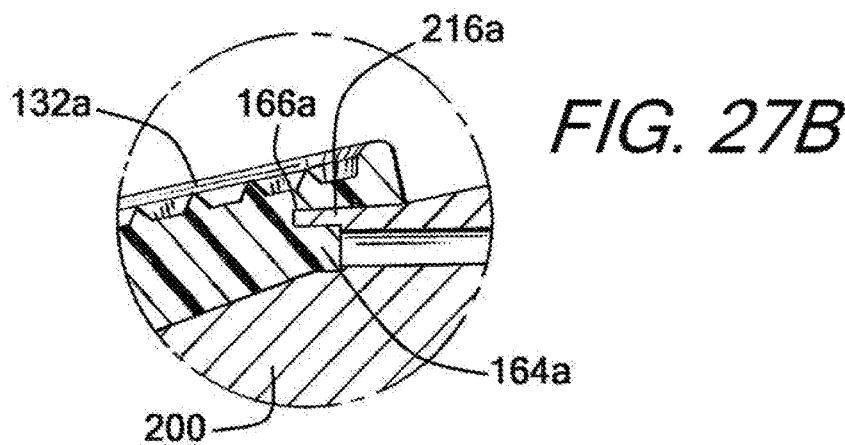
FIG. 27B is an enlarged partial cross-sectional view of the area indicated in FIG. 27B showing a pin portion of the core mold member within the dispenser actuator assembly.

It is understood that the dispenser actuator assembly 100 is formed in the mold cavity including the first actuator arm 132a and the second actuator arm 132b. As shown in FIG. 25, the upper mold member 202 and the lower mold member 204 are spaced away from the core mold member 200. It is desirable for the actuator arms 132a, 132b to maintain contact with the core mold member 200 until the assembly 100 can be ejected from the core mold member 200. With such movement of the mold members 202, 204, the actuator arms could "stick" to the mold members 202, 204 where the actuator arms 132a, 132b will pivot upwards following movement of the mold members 202,204. This premature flexing of the actuator arms 132a, 132b will have a detrimental effect on operation of the actuator arms in actuating a dispenser 10. FIGS. 26-27B show the dispenser actuator assembly 100 still on the core mold member 200 after removal of the upper mold member 202 and the lower mold member 204 (The mold members 202, 204 are not shown for clarity.). As previously discussed, the finger projections 216a, 216b extend into the mold cavity 206. The finger projections 216a, 216b are positioned above the bosses 164a, 164b and, therefore, keep the actuator arms against the core mold member 200. The finger projections 216a, 216b are positioned between the bosses 164a, 164b and the underside surface of the actuator arms 132a, 132b. As can be appreciated from FIGS. 28A and 28B, ejector pins are inserted through passageways in the core mold member 200 to engage the bosses 164a, 164b and eject the assembly 100 from the core mold member 200. As shown in FIG. 28B, the finger projections 216a, 216b are removed from the respective indentations 166a, 166b of the assembly 100. Once removed, it is understood that the indentation slots 166a, 166b are revealed. The dispenser actuator assembly 100 is then properly formed and ready for further processing and use.

It is understood that additional features can be incorporated into the molding process. The gates for injecting molded material MM into the mold cavity 206 can be varied to achieve desired characteristics in the assembly. In a further exemplary embodiment, a multi-shot molding process could be utilized. For example, a two-shot molding process could be utilized wherein the flex plate structure is molded from a more flexible material while other structures of the assembly 100 such as the base member 102 and the actuator assembly 104 are formed from a more rigid material.

The dispenser actuator assembly 100 can be formed in the injection molding process from a variety of different injected molded materials. Selection of the material will depend on the desired operational characteristics of the assembly 100 such as the amount of rupturing force to be generated. The assembly 100 could be formed from polyolefin family of resins. The material could be polyethylene or polypropylene and a combination thereof. The material could also be nylon. Because of the structural features described above, it is possible to use more rigid/brittle materials as well as materials having a higher flexural modulus. The material could also be amorphous polymers including acrylic, acrylonitrile butadiene styrene, or polycarbonate. The material for the assembly 100 could further be a polyvinylidene fluoride (PVDF) material. With the broader selection of materials possible, the assembly 100 can also be used in a broader range of applications requiring rupturing of different types of containers. The dispenser actuator assembly 100 could also be made of materials for specialty application such as materials that are capable of being autoclavable.

It is understood that the dispenser actuator assembly 100 can have certain modified structures to enhance the operability of the assembly 100.

FIGS. 35-36 disclose another alternative embodiment of the dispenser actuator assembly 100 according to an exemplary embodiment of the invention. The structure of the dispenser actuator assembly 100 of FIGS. 35-36 is similar to the structure of the dispenser actuator assembly 100 of FIGS. 9-19. The description of FIGS. 9-19 is applicable to the dispenser actuator assembly 100 of FIGS. 35-36 regarding structure and operation. Certain differences are discussed herein. In this embodiment, the apertures 144 extend completely through the actuator arms 132a, 132b. Thus, the apertures 144 extend through the first segments 152a, 152b of the protrusions 150a, 150b. In addition, the ridges 148a, 148b of the finger pads 146a, 146b have different segments. For example, one segment of the ridges 148a, 148b on the intermediate segment 138a, 138b of the actuator arms 132a, 132b are generally transverse to other ridges 148a, 148b on the actuator arms 132a, 132b. In addition, the depending protrusions 150a, 150b also have a different configuration. The second segment 154a, 154b of the protrusion 150 tapers towards a minimal dimension generally at an intermediate portion on an underside of the actuator arm 132a, 132b. An additional boss 164 (FIG. 36) is also included at an intermediate portion of the second segment 152a, 152b of the depending protrusion 150a, 150b. The description of FIGS. 9-19 is applicable to the dispenser actuator assembly 100 of FIGS. 35-36 regarding structure and operation.

FIGS. 37-38 disclose another alternative embodiment of the dispenser actuator assembly 100 according to an exemplary embodiment of the invention. The structure of the dispenser actuator assembly 100 of FIGS. 37-38 is similar to the structure of the dispenser actuator assembly 100 of FIGS. 9-19. Similar to the embodiment of FIGS. 35-36, the apertures 144 extend completely through the actuator arms 132a, 132b. The depending protrusions 150a, 150b are rigid and have a similar configuration to the previous embodiments and also have a thinner dimension at the second segments 154a, 154b. The description of FIGS. 9-19 is applicable to the dispenser actuator assembly 100 of FIGS. 37-38 regarding structure and operation.

Figure 39:
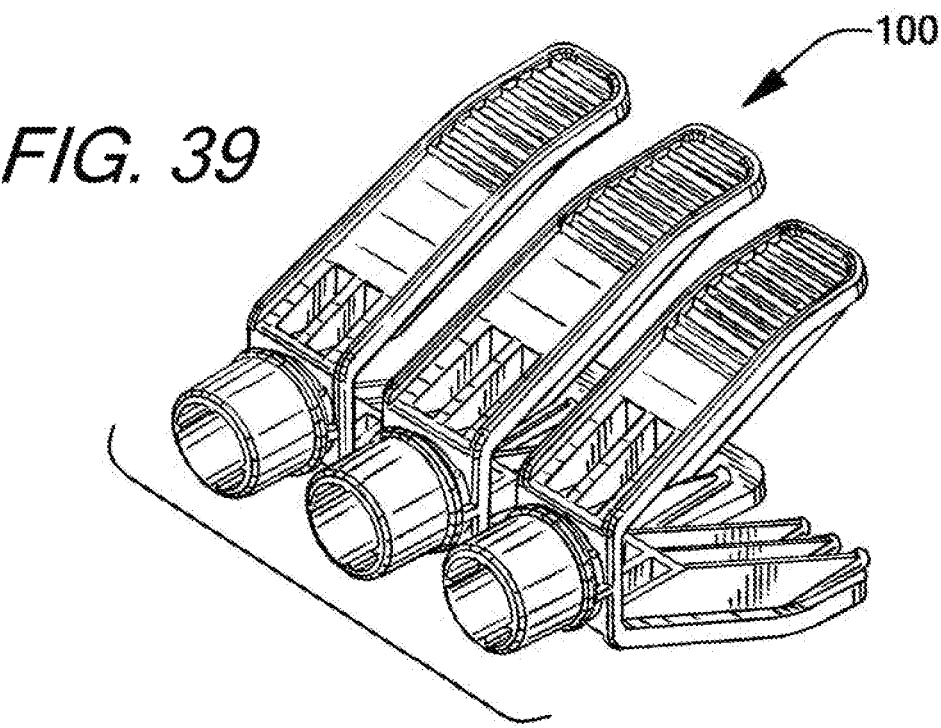
FIG. 39 is a front perspective view of a series of alternative embodiments of the dispenser actuator assembly wherein the assemblies have actuator arms of varying lengths.
Figure 40:
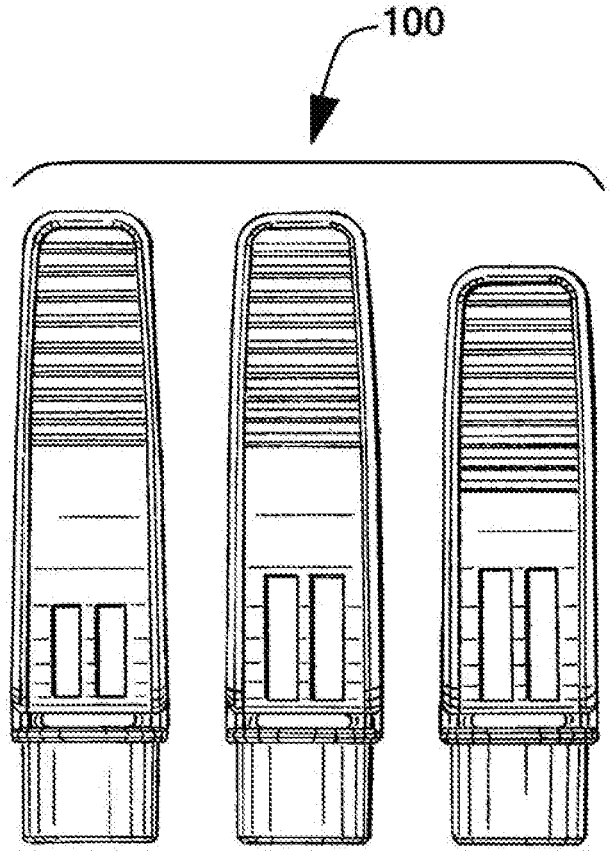
FIG. 40 is a top plan view of the alternative embodiments shown in FIG. 39.

FIGS. 39-40 show a plurality of dispenser actuator assemblies 100. It is shown that the length of the first and second actuator arms 132a, 132b can vary such as for adjusting the moment arms and desired forces required to deflect the arms 132a, 132b. Also, the actuator arms 132a, 132b could have a change in angle formed at an intermediate portion of the arms 132a, 132b. It is understood that such angle could vary as desired. Other structures of the dispenser actuator assembly 100 in FIGS. 39-40 are similar to the dispenser actuator assembly 100 of FIGS. 9-19. The description of FIGS. 9-19 is applicable to the dispenser actuator assembly 100 of FIGS. 39-40 regarding structure and operation.

Figure 41:
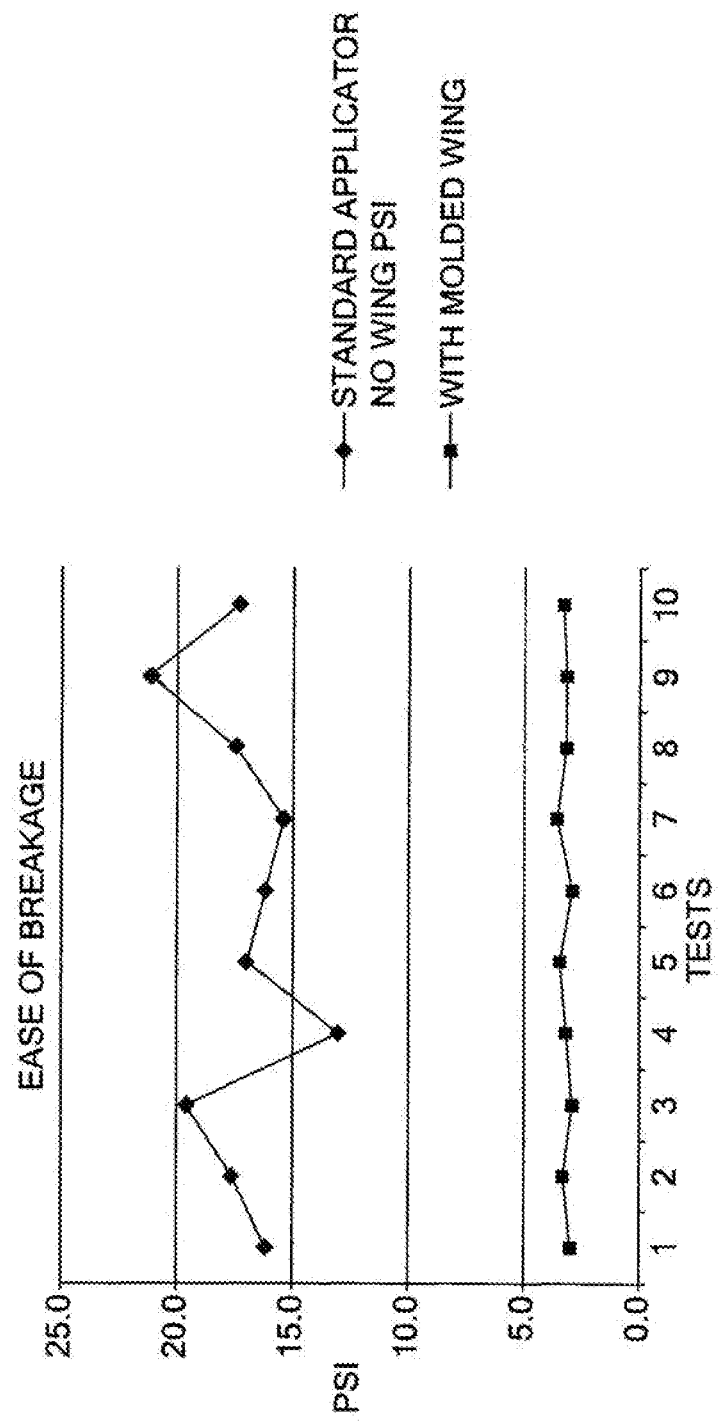
FIG. 41 is a graphical representation of the breakage pressure (force) required to break the glass ampoule assembly via finger pressure (e.g. no actuator assembly) and via use with the dispenser actuator assembly.

Prior to the invention, a user typically must squeeze, via finger pressure, the outer container 14 of the glass ampoule assembly 10 to crush the glass ampoule 12. The squeezing thumb/fingers provides a force to deform the outer container 14 and crush the glass ampoule 12. The required finger pressure could be considered significant for certain users having limited strength in their respective digits. The dispenser actuator assembly 100 provides mechanical advantage from the actuator arms 132a, 132b wherein the required finger pressure can be reduced. FIG. 41 shows graphically, the reduction in finger pressure required to crush the glass ampoule. The upper line represents the finger pressure required to crush the glass ampoule assembly 10 when a user directly squeezes, via finger pressure, the outer container 14 of the glass ampoule assembly 10. The required pressure is typically approximately 15-20 psi. The lower line represents the finger pressure required to crush the glass ampoule assembly 10 when the dispenser actuator assembly 100 is used. As can be seen, the finger pressure required is typically less than 5 psi and could be approximately 3-4 psi. A significant reduction in required psi is achieved with the dispenser actuator assembly 100. A lower, more constant and predictable breakage force is also achieved. It is understood that the dispenser actuator assembly 100 could include alternative features to provide further reduction is required psi as desired. It is understood that the angle that the actuator arms 132a, 132b extend from the base member 102 or flex plate 180 can vary and set at a greater angle that would allow more force to be generated. This can lead to a more difficult grip for certain users and, therefore, a sufficient angle is determined to provide the necessary rupturing force with an ergonomically-friendly grip of a user.

It is understood that the dispenser actuator assembly 100 and the glass ampoule assembly 10 may be distributed or sold as a kit, e.g., together as a single unit package. FIG. 42 shows a representative package assembly 220, which may be a blister package 220. The blister package 220 containing the dispenser 10 and actuator assembly 100 may be referred to as a dispenser and actuator assembly package assembly. The dispenser actuator assembly 100 is mounted on the glass ampoule assembly 10 generally proximate a central intermediate segment of the outer container 14 of the glass ampoule assembly 10 to form a tandem unit. The package assembly 200 is provided having a bottom member 222 or blister layer 222. The blister layer 222 has a blister recess 224 dimensioned to receive the tandem unit. The recess 224 has a first recess section 226 and a second recess section 228. The first recess section 226 has a greater longitudinal dimension than a lateral dimension to receive and accommodate the glass ampoule assembly 10. The second recess section 228 is generally rectangular and intersects the first recess section 226 at generally a central portion of the first recess section 226. The second recess section 228 defines an outer wall 229. The second recess section 228 is generally dimensioned to receive the dispenser actuator assembly 100 mounted on the glass ampoule assembly 10. When the tandem unit is placed in the recess 224, package spaces PS are defined between the actuator arms 132a, 132b and the glass ampoule assembly 10. The bottom member 222 can be formed from materials that resist inadvertent forces being placed onto the actuator arms of the dispenser actuator assembly inside the package. The blister layer 222 can be made from a variety of different materials. In one exemplary embodiment, the blister layer 222 is made of a thermoplastic material, such as polyvinyl chloride or polyolefin. Still other materials are possible and the blister layer 222 can also be laminated with other layers such as a tear resistant layer.

As discussed, the package assembly 220 may be considered a blister package wherein a cover member 230 or film member 230 is adhered over the blister layer 222 to seal the tandem unit in the package assembly 200 until ready to be used. The cover member 230 can also be made from a variety of materials including a paper material, a thermoplastic film layer or a foil layer or still other materials. The foil member could be an aluminum foil. The cover member 230 could also be formed from a laminate material of a paper and a metal foil layer. The foil layer could also be coated with a film of a thermoplastic material such as polyethylene, polystyrene or the like. The cover member 230 is secured to the blister layer 222 by sealing through the application of heat and pressure. Other sealing techniques between the cover member 230 and the blister layer 222 can also be utilized. In one exemplary embodiment, the cover member 230 is releasably secured or releasably sealed to the blister layer 222. The cover member 230 may define a pull tab for a user to pull the cover member 230 from the blister layer 222. In other exemplary embodiments, the cover member 230 can be punctured or torn to gain access to the dispenser and actuator assembly tandem unit. The tandem unit in the package assembly 220 can then be further packaged, boxed, shipped or otherwise transported in preparation for use.

FIGS. 43A-C show additional features associated with the package assembly 220. FIG. 43A shows the package assembly 220 containing the tandem unit of the dispenser actuator assembly 100 mounted on the glass ampoule assembly 10. The tandem unit is positioned in the blister recess 224. As further shown in FIG. 43A, wedge members 232, or first and second blocking members 232, can be utilized between the glass ampoule assembly 10 and the actuator arms 132a, 132b of the dispenser actuator assembly 100. The blocking member 232, or wedge member 232, generally has a right-triangle-type shape having an angled surface 234 and a primary linear surface 236, as well as a secondary linear surface 238. A right angle is defined between the linear surfaces 236, 238. In this exemplary embodiment, two wedge members 232 are utilized, e.g. a first blocking member 232 and a second blocking member 232. As further shown in FIG. 43A, a first blocking member 232 is positioned in the package space PS or recess space PS in the second recess section 228 generally between the first actuator arm 132a and the second container 14 of the glass ampoule assembly 10. In particular, the first angled surface 234 of the first blocking member 232 is positioned in confronting relation to the second segment 154a of the depending protrusion 150a. The second segment 154a of the first depending protrusion 150 defines an inclined surface as shown in FIG. 43A. In an exemplary embodiment, the respective surfaces of the angled surface 234 of the blocking member 232 and depending protrusion 150 engage one another. It is understood that a small gap could be present if desired. The primary linear surface 236 engages the outer surface of the second container 14 of the glass ampoule assembly 10, e.g. the straight cylindrical surface of the second container 14. The secondary linear surface 238 engages a rear wall portion of the second recess section 228. Thus, the first blocking member 232 is confined or wedged between the first actuator arm 132a and the second container 14 of the glass ampoule assembly 10.

Similarly, a second blocking member 232 is positioned in the package space PS or recess space PS in the second recess section 228 generally between the second actuator arm 132b and the second container 14 of the glass ampoule assembly 10 (e.g., generally opposed to the first blocking member 232). In particular, the second angled surface 234 of the second blocking member 232 is positioned in confronting relation to the second segment 154b of the depending protrusion 150b, that defines a second inclined surface of the second actuator arm 132b. In an exemplary embodiment, the respective surfaces of the second angled surface 234 and depending protrusion 150 engage one another. It is understood that a small gap could be present if desired. The primary linear surface 236 of the second blocking member 232 engages the outer surface of the second container 14 of the glass ampoule assembly 10, e.g. the straight cylindrical surface of the second container 14. The secondary linear surface 238 engages a rear wall portion of the second recess section 228. Thus, the second wedge member 232 is confined or wedged between the second actuator arm 132b and the second container 14 of the glass ampoule assembly 10. As further shown in FIG. 43A, the respective distal ends 136a, 136b of the first and second actuator arms 132a, 132b confront and engage outer walls 229 of the second recess section 228 of the blister recess 224.

As can be appreciated from FIG. 43A, in this configuration, the first blocking member 232 and the second blocking member 232 prevent movement of the actuator arms 132a, 132b towards one another to prevent premature crushing of the glass ampoule 12 of the glass ampoule assembly 10. Even if a small gap is provided between the actuator arms 132a, 132b and the angled surfaces 234 of the blocking members, the gap is controlled such that the actuator arms 132a, 132b cannot move enough to crush the glass ampoule 12. Thus, in this configuration, the package assembly 220 can be further packaged, shipped and transported wherein any jostling of the package will not allow for inadvertent or premature actuation of the glass ampoule assembly 10.

FIG. 43B shows an alternative embodiment of the package assembly 220. In this embodiment, the first blocking member 232 and the second blocking member 232 are integrally formed in the blister layer 222 of the package assembly 220. In an exemplary embodiment, the blocking members 232 can be pressed to be integrally formed such as in the shape of the blocking member 232 shown in FIG. 43A. Other processes can be used to form the integral blocking members 232 such as blow molding or the like. Thus, the integral blocking member 232 formed in the blister layer 222 can have the angled surface 234, primary linear surface 236 and the second linear surface 238. The integral blocking members 232 are positioned between the actuator arms 132a, 132b and the glass ampoule assembly 10 as described above. As can be appreciated from FIG. 43B, in this configuration, the blocking members 232 prevent movement of the actuator arms 132a, 132b towards one another to prevent premature crushing of the glass ampoule 12 of the glass ampoule assembly 10. Thus, in this configuration, the package assembly 220 can be further packaged, shipped and transported wherein any jostling of the package will not allow for inadvertent or premature actuator of the glass ampoule assembly 10. It is appreciated that the integral blocking members 232 in FIG. 43B would look the same as in FIG. 43A.

FIG. 43C shows a further alternative embodiment of the package assembly 200. The blister layer 222 further has integral blocking members 232 formed therein. In this configuration, the blocking members 232 are generally round or circular members, e.g. having a circular cross-section. Similar to the other embodiments, the blocking members 232 are formed and dimensioned to be positioned between the actuator arms 132a, 132b and the second container 14 of the glass ampoule assembly 10. As can be appreciated from FIG. 43C, in this configuration, the blocking members 232 prevent movement of the actuator arms 132a, 132b towards one another to prevent premature crushing of the glass ampoule 12 of the glass ampoule assembly 10. Thus, in this configuration, the package assembly 220 can be further packaged, shipped and transported wherein any jostling of the package will not allow for inadvertent or premature actuator of the glass ampoule assembly 10.

The kit described above may include the dispenser 10, the dispenser actuator assembly 100 and the package assembly 220 including any desired blocking members 232. It is understood that the kit could include different combinations of such elements or additional elements. For example, the kit could contain multiple applicator assemblies 16 to be used for dispensing flowable materials in different applications. The applicator assembly 16 may also be provided having different tips 54 for different applications.

As discussed above, the dispenser actuator assembly 100 can be utilized to actuate a glass ampoule assembly such as shown in FIGS. 1-4. The dispenser actuator assembly 100 can also be used with other types of glass ampoule assemblies such as the assembly 10 shown in FIGS. 5-8. FIGS. 44-45 show the dispenser actuator assembly 100 mounted on the glass ampoule assembly of FIGS. 5-8, and in the first neutral position NP. It is understood that the cardboard sleeve 18 is not utilized in this connection where the cardboard sleeve 18 has been previously removed. The glass ampoule assembly 10 is actuated similar as described above and shown in FIG. 45. A user engages the first actuator arm 132a and the second actuator arm 132b and applies a force F wherein the arms 132a, 132b move towards one another from the neutral position NP to the actuating position AP and wherein the second container 14 is deformed and the glass ampoule 12 is crushed. Flowable material M is then dispensed from the glass ampoule assembly 10 as described above.

As described above, the dispenser actuator assembly 100 can be used with a dispenser 10 such as a glass ampoule assembly 10. It is understood that the dispenser actuator assembly 100 can also be used with other types of dispensers 10 that utilize a rupturable feature in order to dispense flowable materials M from the dispenser 10. FIG. 46-48 show another dispenser 10 in the form of a plastic ampoule assembly 60. The plastic ampoule assembly has an outer wall 62 and a fracturable membrane 64 defining a chamber 66 for containing a flowable material M. The membrane 64 has a weld seam 68 formed during an injection molding process wherein a first segment of injected molding material abuts a second segment of injected molding material to form the weld seam 68 such as disclosed in U.S. Pat. No. 6,641,319, which patent is expressly incorporated herein. The membrane 64 having the weld seam 68 could also be formed in a conical shape such as disclosed in U.S. Pat. No. 10,392,163, which patent is expressly incorporated herein. It is understood that the plastic ampoule 60 can also be utilized an applicator 16 for dispensing the flowable material M. FIG. 47 discloses the dispenser actuator assembly 100 mounted on the plastic ampoule assembly 60. The dispenser actuator assembly 100 and actuator arms 132a, 132b are in the first neutral position NP. It is understood the mounting is such that the interface areas 158a, 158b are positioned proximate the fracturable membrane 64. Similar to the operation described above, after the dispenser actuator assembly 100 is mounted on the plastic ampoule 60, a user applies a compressive force F to the actuator arms 132a, 132b wherein the protrusions 150a, 150b at the interface areas 158a, 158b engage and deflect the outer wall 62 of the plastic ampoule 60 thereby applying the force proximate the membrane 64 wherein the weld seam 68 is fractured. Thus, the actuator arms 132a, 132b move the from the neutral position NP to the actuating position AP. Upon fracturing of the weld seam 68, the flowable material M can pass through the membrane 64 and into the applicator 16 to be dispensed from the plastic ampoule 60. It is understood that the protrusions 150a, 150b are positioned proximate the membrane 64 to apply the force F to the membrane 64 to fracture the weld seam 68.

Figure 49:
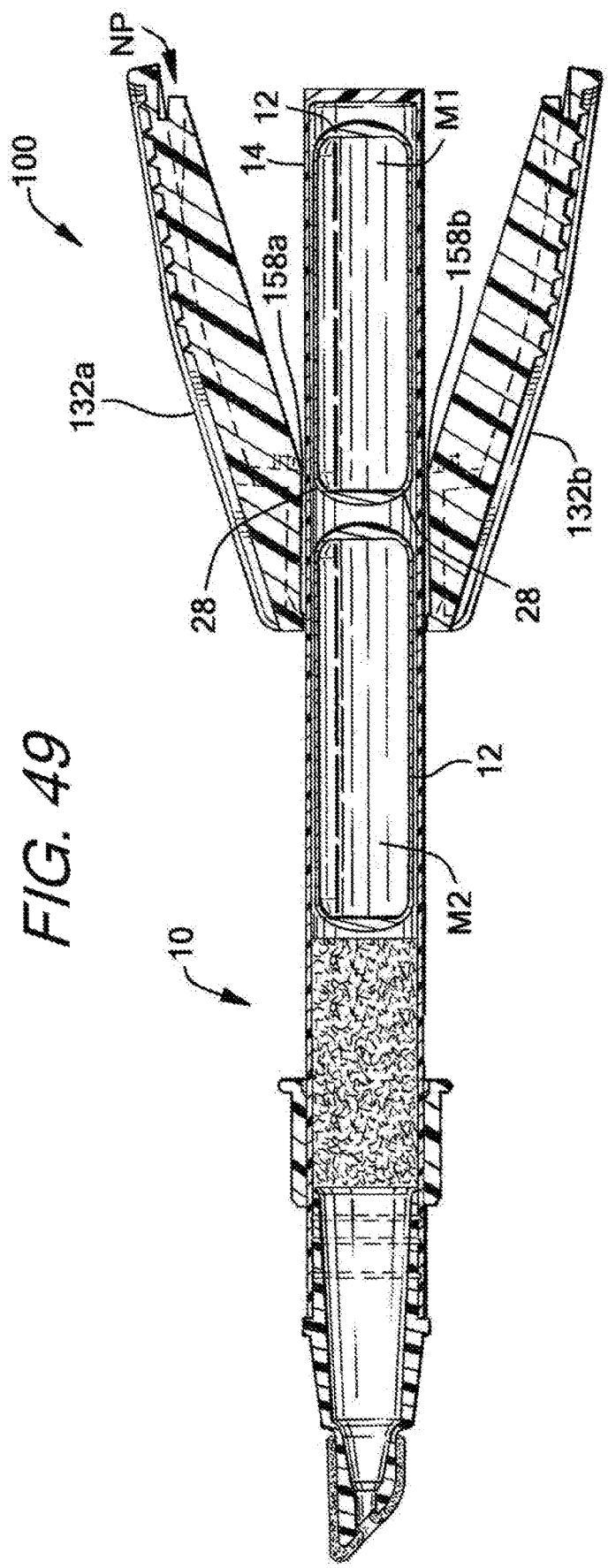
FIG. 49 is a side cross-sectional view of the dispenser actuator assembly mounted on an alternative embodiment of the dispenser in the form of a tandem glass ampoule assembly.
Figure 50:
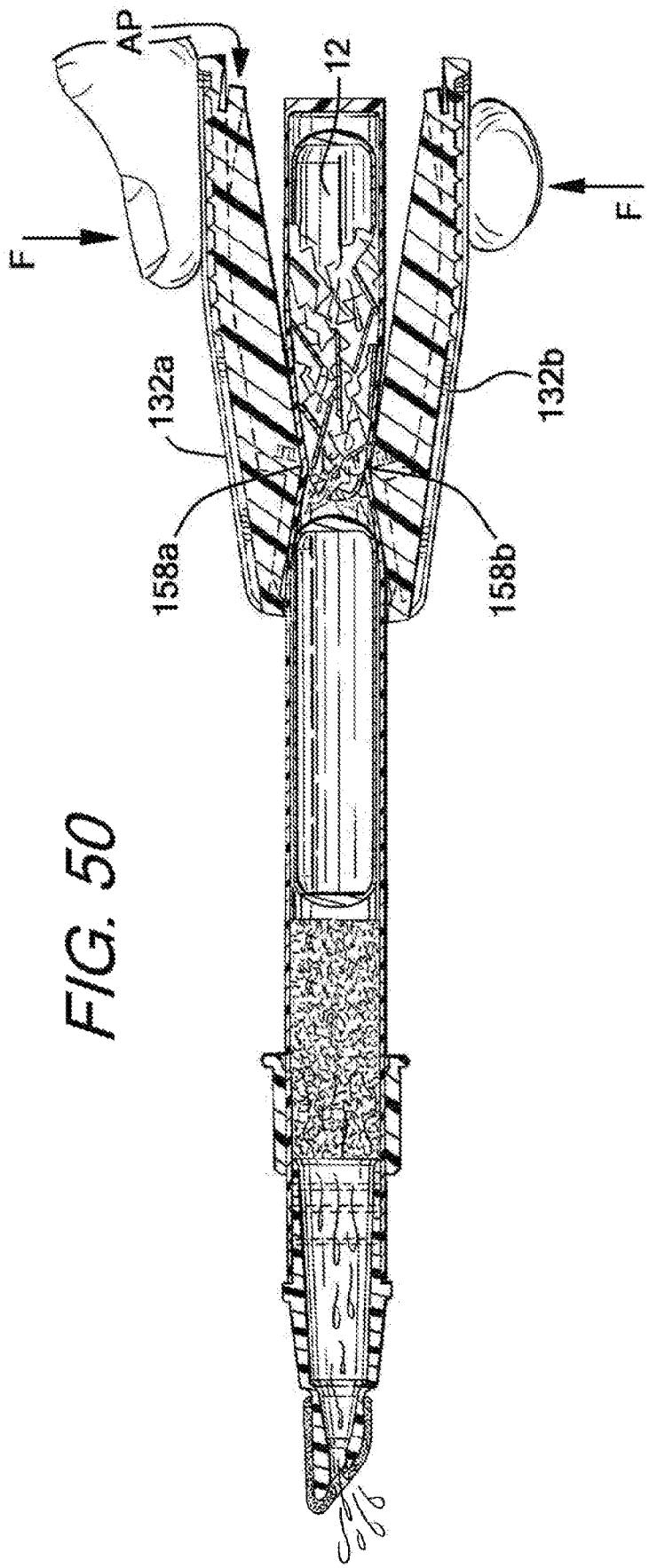
FIG. 50 is a side cross-sectional view of the dispenser actuator assembly mounted on the dispenser of FIG. 49 and showing actuation of the dispenser actuator assembly wherein a rear glass ampoule in the dispenser is crushed.
Figure 51:
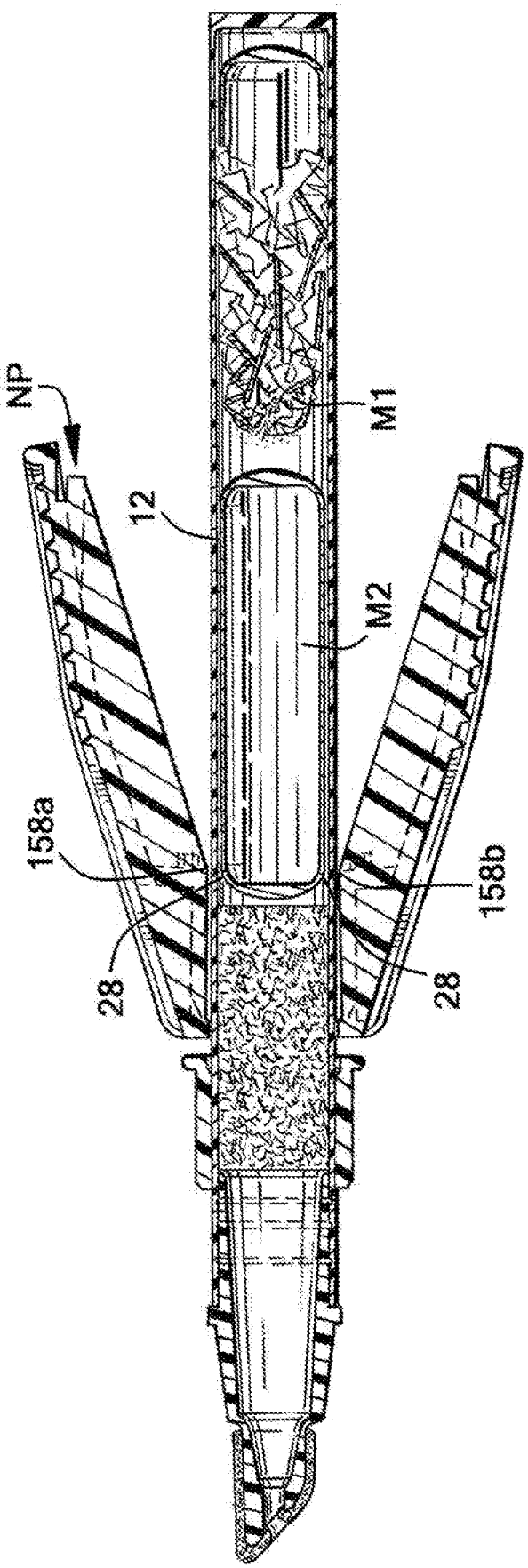
FIG. 51 is a side cross-sectional view of the dispenser actuator assembly mounted on the dispenser of FIG. 49 wherein the dispenser actuator assembly is moved up on the glass ampoule assembly proximate a front glass ampoule.

FIGS. 49-52 disclose use of the dispenser actuator assembly 100 in use with another alternative embodiment of a glass ampoule assembly 10. The structure of the glass ampoule assembly 10 is generally similar in structure to the glass ampoule assembly 100 of FIGS. 1-4. The glass ampoule assembly 10 in FIGS. 49-52 utilizes multiple glass ampoules 12 in a tandem unit for a two-part flowable material configuration. Thus, the second container 14 contains a rear glass ampoule 12 and a front glass ampoule 12. The rear glass ampoule 12 contains a first flowable material M1. The front glass ampoule 12 contains a second flowable material M2. FIG. 49 shows the dispenser actuator assembly 100 mounted on the glass ampoule assembly 10 wherein the interface areas 158a, 158b of the protrusions 150a, 150b are positioned proximate a first interface 28 of the rear glass ampoule 12. This represents the neutral position NP. FIG. 50 shows a user applying a force F to the actuator arms 132a, 132b to move from the neutral position NP to the actuating position AP to crush the rear glass ampoule 12. After crushing the rear glass ampoule 12, the user can slide the dispenser actuator assembly 100 along the second container 14 of the glass ampoule assembly 10 wherein the interface areas 158a, 158b are positioned proximate the first interface area 28 of the front glass ampoule 12. This configuration is shown in FIG. 51. FIG. 52 shows the user applying a force F to the actuator arms 132a, 132b from a second neutral position NP to a second actuating position AP to crush the front glass ampoule 12. After crushing the rear glass ampoule 12 and the front glass ampoule 12, the respective flowable materials M1, M2 of the ampoules 12 can mix together to form a mixture MX. The user may shake the glass ampoule assembly 10 to assist in the mixing to form the mixture MX. The user can dispense the mixture MX from the applicator 16 of the glass ampoule assembly 10 onto a receiving surface as described above.

The dispenser actuator assembly 100 provides several benefits. The actuator assembly provides mechanical advantage for a user to crush, rupture or fracture the dispenser. The actuator arms can vary in length and resiliency to provide a desired mechanical force in rupturing the dispenser. Because the dispenser actuator assembly allows for a user to apply an increased force than from finger pressure alone, the assembly can be used to rupture more robustly designed dispensers. Such dispensers may be designed to crush under an increased force to minimize the chances of inadvertent rupture. In addition, the dispenser actuator assembly is designed to crush the glass ampoule at the optimal location at the interface area proximate the domed-portion of the glass ampoule to enhance the rupturing of the glass ampoule. Furthermore, as the user engages the actuator arms of the assembly rather than directly engaging the outer container of the dispenser, the chances that glass shards from the crushed glass ampoule can injure the fingers or hand of the user is minimized. The dispenser actuator assembly can also be adjustably mounted along a length of the glass ampoule assembly. For example, the dispenser actuator assembly can be slid along a length of the outer container of the glass ampoule assembly to a desired location. This helps in further manipulating flowable material from the glass ampoule assembly. In addition, the dispenser actuator assembly 100 can be removable attached to the dispenser. Once the dispenser is crushed and the flowable material is dispensed from the dispenser, the dispenser actuator assembly can be removed from the dispenser and used to crush multiple other dispensers. It is understood as well that the dispenser actuator assembly 100 could be manufactured as a single-use assembly that is discarded. It is further understood that the assembly 100 can be positionally adjusted on the glass ampoule assembly 10 to manipulate flowable material as desired or break the glass ampoule at a particular location. It is further understood that the flex plate structure provides several benefits as discussed above including flexing across a greater distance on the plate as well as providing for movement of the actuator arms independently of the support of the glass ampoule assembly by the base member.

It is understood that any reference to an element using designations such as "first" or "second" or the like does not limit the quantity or order of those elements, unless such limitation is explicitly stated. These designations are used to distinguish between elements or other references to an element. Accordingly, a reference to a first element or a second element does not mean that only two elements may be employed or that the first element must precede the second element in some manner. In addition, a set of elements may comprise one or more elements. In addition, references to "top" or "bottom" or "front" or "rear" are used to reference relative positions of elements and should be construed as a limiting positional requirement.

It is further understood that the present description includes several different embodiments with different features depending on the embodiment being described. It is understood that the various features or structures can be combined among the various embodiments in further exemplary embodiments of the invention.

The dispenser 10 is permitted to be used in a wide variety of uses and applications, and contain and dispense a large variety of fluids and other flowable substances. The following is a non-exhaustive discussion regarding the many possible uses for the dispenser of the present invention, and in particular, the types of materials that are capable of being contained in the dispensers and dispensed therefrom. It is understood that related uses to those described below are also possible with the dispenser. It is also understood that the following discussion of potential uses is applicable to any of the dispenser embodiments disclosed and discussed herein.

The dispenser used with the dispenser actuator assembly of the present invention is designed to primarily contain and dispense flowable materials that are fluids. Other flowable materials can also be dispensed. For example, the flowable material could be a liquid, powder, gel or other type of flowable substance or flowable material. Also, in other embodiments such as dispensers containing multiple chambers for different flowable materials, the flowable materials M1, M2 could both be fluids. In another embodiment, the first flowable material M1 could be a liquid, and the second flowable material M2 could be a powder to be mixed with the fluid. Other combinations depending on the use are also permissible.

This permits the dispenser 10 to be used in a wide variety of uses and applications, and contain and dispense a large variety of fluids and other flowable substances. The following is a non-exhaustive discussion regarding the many possible uses for the dispenser of the present invention, and in particular, the types of materials that are capable of being contained in the dispensers and dispensed therefrom. It is understood that related uses to those described below are also possible with the dispenser. It is also understood that the following discussion of potential uses is applicable to any of the dispenser embodiments disclosed and discussed herein.

In one example, the dispenser of the present invention can be used in medical applications. In one particular exemplary embodiment, the dispenser may contain a surgical antiseptic such as for cleaning and preparing a body area for incision, and sometimes referred to as a surgical prep solution. One type of antiseptic may be chlorhexidine gluconate (CHG). This CHG-based antiseptic could also be combined with a medical sealant such as cyano-acrylic wherein the dispenser is used to contain and dispense cyano-acrylic chlorhexidine gluconate (CACHG). Other types of medical sealants could also be used. Other types of antiseptics could be iodine-based such as iodophoric skin tinctures, which are commercially available. Other antiseptics and antimicrobial agents could also include other iodine-based complexes, alcohol-based complexes or peroxides. Additional additives may also be used with the antiseptic such as colorants. A single chamber dispenser may be used in such an application, but a multi-chamber dispenser such as disclosed herein may also be used.

In another example, the dispenser of the present invention can be used in adhesive-type applications. The dispenser can dispense a flowable material or mixture that is an adhesive, epoxy, or sealant, such as an epoxy adhesive, craft glue, non-medical super glue and medical super glue. The dispenser could also be used with shoe glue, ceramic epoxy and formica repair glue. The dispenser could further be used for a variety of other adhesive dispensing applications, mastic-related resins or the like.

In another example, the dispenser of the present invention can be used in automotive applications. The dispenser can dispense a flowable material or mixture that is an automotive product, such as a rear view mirror repair kit, a vinyl repair kit, auto paints, an auto paint touch up kit, a window replacement kit, a scent or air freshener, a windshield wiper blade cleaner, a lock de-icer, a lock lubricant, a liquid car wax, a rubbing compound, a paint scratch remover, a glass/mirror scratch remover, oils, radiator stop-leak, a penetrating oil, or a tire repair patch adhesive. Other automotive applications could include acetone-based products such as windshield primer. Additional automotive applications could be for general auto/motorcycle or bicycle repair kits including chain oils.

In another example, the dispenser of the present invention can be used in chemistry-related applications. The dispenser can dispense a flowable material or mixture that is a chemistry material such as a laboratory chemical, a buffer solution, a rehydration solution of bacteria, a biological stain, or a rooting hormone. The dispenser may also be used as a chemical tester. In one such application, the dispenser can be used for testing drinks for various "date rape" drugs. Other types of chemical testers are also possible. The dispenser could be used to contain various types of chemicals including solvents. In a particular application, the additional material formulations used to form the dispenser allow the dispenser to store and dispense methyl ethyl ketone.

In another example, the dispenser of the present invention can be used to dispense a flowable material or mixture is a cosmetic and beauty supply/toiletry product. For example, the dispenser can be used for a nail polish, lip gloss, body cream, body gel, body paints, hand sanitizer, nail polish remover, liquid soaps, skin moisturizers, skin peels, tooth whiteners, hotel samples, mineral oils, toothpastes, mouthwash or sunscreens. The flowable material could also be a fragrance such as women's perfume or men's cologne. The flowable material could also be tattoo inks. The flowable material could be used for solutions for treating and/or removing tattoo ink.

The cosmetic applications could also include hair care type applications. In another particular example, the dispenser of the present invention can be used in a hair dye kit. Certain hair dye kits come in multiple components that are separately stored wherein the dispenser embodiment disclosed herein having a dividing wall that cooperates to define separate chambers can be utilized. Thus, the dispenser of the present invention can be used in a two-part hair care product such as a hair dye kit. A first flowable substance of the hair dye kit can be carried in the first chamber, and a second flowable substance of the hair dye kit can be carried in the second chamber. The membrane is ruptured wherein the two flowable substances can be mixed together to form a mixture or solution. The mixture or solution can then be dispensed from the dispenser onto the hair of a user. The dispenser can also dispense a flowable material or mixture in other hair care products, such as hair bleaches, hair streaking agent, hair highlighter, shampoos, other hair colorants, conditioners, hair gels, mousse, hair removers, or eyebrow dye.

In another example, the dispenser of the present invention can be used in crafting applications or stationary products. The dispenser can also dispense a large variety of stationery or craft products, such as magic markers, glitter gels, glitter markers, glitter glues, gel markers, craft clues, fabric dyes, fabric paints, permanent markers, dry erase markers, dry eraser cleaner, glue sticks, rubber cement, typographic correction fluids, ink dispensers and refills, paint pens, counterfeit bill detection pen, envelope squeeze moisturizers, adhesive label removers, highlighters, and ink jet printer refills.

In another example, the dispenser of the present invention can also dispense a flowable material or mixture that is an electronics-related product. For example, the electronics product could be a cleaning compound, a telephone receiver sanitizer, cell phone cleaner or protectants, a keyboard cleaner, a cassette recorder cleaner, audio/video disc cleaner, a mouse cleaner, or a liquid electrical tape.

In another example, the dispenser of the present invention can dispense a flowable material or mixture in food product applications. For example, the food product may be food additives, food colorings, coffee flavorings, cooling oils, spices, flavor extracts, food additives, drink additives, confections, cake gel, pastry gel, frostings, sprinkles, breath drops, condiments, sauces, liquors, alcohol mixes, energy drinks, or herbal teas and drinks.

In another example, the dispenser of the present invention can be used in home repair product and home improvement applications. The dispenser can also dispense a flowable material that is a home repair product, such as a caulking compounds or materials, a scratch touch up kit, a stain remover, a furniture repair product, a wood glue, a patch lock, screw anchor, wood tone putty or porcelain touch-up. The dispenser could also dispense a plumbing flux applicator, rust remover and tree wound treatment. In certain home repair or home improvement applications, the dispenser can be used in paint applications. The dispenser can dispense a variety of paint products such as general paints including interior/exterior paints, novelty paints, paint additives, wood stain samples, varnishes, stains, lacquers, caulk, paint mask fluid or paint remover.

In another example, the dispenser of the present invention can be used in household related products. For example, the dispenser could be used for cleaning agents, pest control products, a fish tank sealant or a fish tank treatment, a leak sealant, a nut/bolt locker, screw tightener/gap filler, a super glue remover or goo-b-gone. The dispenser could also be used for a colorant dispenser, or disinfectants, a plant food, fertilizers, bug repellants or a cat litter deodorant. The dispenser could also dispense toilet dyes and treatments, eyeglass cleaners, shoe polishes, clothing stain removers, carpet cleaners and spot removers, multi-purpose oils, and ultrasonic cleaner concentrate. The household product could include a variety of pet-related products including but not limited to an animal medicine dispenser, pet medications, animal measured food dispenser, pet shampoos or odor eliminator liquids. A large variety of pest control products can be dispensed by the dispenser, including insect attractants, pesticides, pet insect repellants, pest sterilizers, insect repellants, lady bug attractant and fly trap attractant. The household product could also include various types of polishes, reagents, indicators and other products.

In another example, the dispenser of the present invention can be used in lubricant applications. The dispenser can dispense a large variety of lubricants including industrial lubricants, oils, greases, graphite lubricants or a dielectric grease.

The dispenser of the present invention can also be used in other medical applications including medical related products, medicinal products and medicaments. Additional medical related product applications can include skin adhesive kits to be used in place of traditional stitching products. As discussed, the dispenser could also be used with topical antiseptics, antimicrobials and surgical scrub products. In addition, the dispenser 10 can dispense a large variety of medicinal products, such as blister medicines, cold sore treatments, insect sting and bite relief products, skin cleaning compounds, skin sealing solutions, skin rash lotions, nasal sanitizers, nasal medications, tissue markers, topical antimicrobials, topical demulcent, treatments for acne such as acne medications, umbilical area antiseptics, cough medicines, waterless hand sanitizers, toothache remedies, cold medicines, sublingual dosages or wart treatments. For example, the dispenser could contain a medicinal product containing hydrogen-peroxide used for dermatological conditions such as warts, seborrheic keratosis or similar skin conditions. The dispenser could also be used to dispense compositions for treating various other skin conditions. The dispenser could also be used in conjunction with a medical device product. Other medical related applications could include various types of dental related products including different types of compounds and treatments applied to a patients' teeth. The dispenser could also be used in veterinary related products.

In another example, the dispenser of the present invention can be used in novelty products. For example, the dispenser can contain materials in a glow-stick device. In such instance, the dispenser is a container that may contain multiple components separately stored until activation to create a glowing state in response to mixture of the components. Furthermore, the dispenser can dispense a flowable material or mixture that is a chemiluminescent light, a Christmas tree scent, a glitter gel, and a face paint. Other types of novelty paints could also be used with the dispenser.

In another example, the dispenser of the present invention can be used in sports products. The dispenser can dispense a variety of sports products including sports eye black, football hand glue, and baseball glove conditioner and pine tar. The dispenser can also dispense wildlife lures. The dispenser can be used in various camping related applications including portable lighting fuels for camp lights or other devices and tent repair kits. The dispenser can also be used in bingo or other game markers.

In another example, the dispenser of the present invention can be used in test kit applications. The dispenser can dispense a flowable material or mixture that is a test kit, such as a lead test kit, a drug kit, a radon test kit, a narcotic test kit, a swimming pool test kit (e.g., chlorine, pH, alkalinity etc.), a home water quality tester, a soil test kit, a gas leak detection fluid, a pregnancy tester, or a respirator test kit. The dispenser can also dispense a flowable material or mixture that as part of a medical device test kit, such as a culture media, a drug monitoring system, a microbiological reagent, a streptococcus test kit, or a residual disinfectant tester. The dispenser may also be used in diagnostic testing kits, explosive testing kits or other test kits. The dispenser can be used in breathalyzer tests, culture media samples and drug test kits.

In another example, the dispenser of the present invention can be used in personal care products or wellness-related products. The dispenser can also dispense a flowable material or mixture that is a personal care product, such as shaving cream or gel, aftershave lotion, skin conditioner, skin cream, skin moisturizer, petroleum jelly, insect repellant, personal lubricant, ear drops, eye drops, nose drops, corn medications, nail fungal medication, aging liquids, acne cream, contact lens cleaner, denture repair kit, finger nail repair kit, liquid soaps, sun screen, lip balm, tanning cream, self-tanning solutions, eye wash solution finger nail repair kits. The dispenser can also be used with aroma therapy products and homeopathic preparations. The dispenser can also dispense various vitamins, minerals, supplements and pet vitamins.

The dispenser can also dispense a flowable material or mixture in a variety of other miscellaneous applications. Such miscellaneous applications may include, but not be limited to use in connection with a suction device for culture sampling, taking various liquid samples or taking various swabbing samples. The dispenser could also be used for float and sinker devices, dye markers, microbiological reagents, and also for manufacturing parts assembly liquids and irrigation solutions. The dispenser may also be used as a chalk dispenser such as in construction applications.

Thus, the dispenser can be used in many different applications including mechanical, chemical, electrical or biomedical uses. The dispenser can dispense any variety of flowable materials including liquids and powders, and further including a liquid and a powder, two or more powders, or two or more liquids. The dispenser may be used as part of 2-part system (mix before use) including a liquid with a powder, a liquid with a liquid, a powder with a powder, or sealed inside another tube or product container or partially sealed, connected or attached to another container. The dispenser may also be used as part of a plunger dispensing system.

While the invention has been described in its preferred embodiments, it is to be understood that the words which have been used are words of description rather than limitation and that changes may be made within the purview of the appended claims without departing from the true scope and spirit of the invention in its broader aspects.

What is claimed is:

1. A dispenser and actuator assembly package assembly comprising:
    a dispenser comprising:
    a crushable glass ampoule containing a flowable material, the glass ampoule contained within an outer container, the outer container having a first open end and a second closed end, and an applicator positioned in the first open end,
    an actuator assembly comprising:
    a base member mounted on the outer container of the dispenser;
    an actuator assembly operably connected to the base member wherein the actuator assembly has a first actuator arm and a second actuator arm each pivotally connected to the base member, the first actuator arm and the second actuator arm extending from the base member in generally opposed relation to define a first position, the first actuator arm having a first protrusion depending therefrom and the second actuator arm having a second protrusion depending therefrom; and
    a blister package comprising:
    a blister layer defining a recess,
    wherein the actuator assembly mounted on the dispenser is received by the recess wherein a first recess space is defined in the recess between the first actuator arm and the outer container, and a second recess space is defined in the recess between the second actuator arm and the outer container;
    a first blocking member positioned in the first recess space preventing movement of the first actuator arm from the first position towards the outer container, and a second block member positioned in the second recess space preventing movement of the second actuator arm from the first position towards the outer container; and,
    a cover member secured to the blister layer enclosing the actuator assembly, dispenser, first blocking member and the second blocking member in the blister recess.

2. The dispenser and actuator assembly package assembly of claim 1 wherein the first blocking member is a separate member from the blister layer.

3. The dispenser and actuator assembly package assembly of claim 1 wherein the second blocking member is a separate member from the blister layer.

4. The dispenser and actuator assembly package assembly of claim 1 wherein the first blocking member is integrally formed in the blister layer.

5. The dispenser and actuator assembly package assembly of claim 1 wherein the second blocking member is integrally formed in the blister layer.

6. The dispenser and actuator assembly package assembly of claim 1 wherein the first protrusion of the first actuator member has a first inclined surface and the outer container has a straight cylindrical outer surface, and the first blocking member has a first angled surface and a first primary linear surface, wherein the first inclined surface of the first protrusion confronts and engages the first angled surface of the first blocking member and the straight cylindrical surface of the outer container confronts and engages the first primary linear surface of the first blocking member.

7. The dispenser and actuator assembly package assembly of claim 6 wherein the second protrusion of the second actuator member has a second inclined surface, and the second blocking member has a second angled surface and a second primary linear surface, wherein the first inclined surface of the second protrusion confronts and engages the second angled surface of the second blocking member and the straight cylindrical surface of the outer container confronts and engages the second primary linear surface of the second blocking member.

8. The dispenser and actuator assembly package assembly of claim 4 wherein the first protrusion of the first actuator member has a first inclined surface and the outer container has a straight cylindrical outer surface, and the first blocking member has a first angled surface and a first primary linear surface, wherein the first inclined surface of the first protrusion confronts and engages the first angled surface of the first blocking member and the straight cylindrical surface of the outer container confronts and engages the first primary linear surface of the first blocking member.

9. The dispenser and actuator assembly package assembly of claim 5 wherein the second protrusion of the second actuator member has a second inclined surface and the outer container has a straight cylindrical outer surface, and the second blocking member has a second angled surface and a second primary linear surface, wherein the second inclined surface of the second protrusion confronts and engages the second angled surface of the second blocking member and the straight cylindrical surface of the outer container confronts and engages the second primary linear surface of the second blocking member.

10. The dispenser and actuator assembly package assembly of claim 4 wherein the first blocking member has a circular cross-section.

11. The dispenser and actuator assembly package assembly of claim 5 wherein the second blocking member has a circular cross-section.

12. A dispenser and actuator assembly package assembly comprising:
   a dispenser comprising:
   a crushable glass ampoule containing a flowable material, the glass ampoule contained within an outer container, the outer container having a first open end and a second closed end, and an applicator positioned in the first open end,
   an actuator assembly comprising:
   a base member mounted on the outer container of the dispenser;
   an actuator assembly operably connected to the base member wherein the actuator assembly has a first actuator arm and a second actuator arm each pivotally connected to the base member, the first actuator arm and the second actuator arm extending from the base member in generally opposed relation to define a first position, the first actuator arm having a first protrusion depending therefrom and the second actuator arm having a second protrusion depending therefrom; and
   a blister package comprising:
   a blister layer defining a recess,
   wherein the actuator assembly mounted on the dispenser is received by the recess wherein a first recess space is defined in the recess between the first actuator arm and the outer container, and a second recess space is defined in the recess between the second actuator arm and the outer container,
   wherein the blister layer defines a first blocking member positioned in the first recess space preventing movement of the first actuator arm from the first position towards the outer container, wherein the blister layer defines a second blocking member positioned in the second recess space preventing movement of the second actuator arm from the first position towards the outer container; and,
   a cover member secured to the blister layer enclosing the actuator assembly and dispenser in the blister recess.

13. The dispenser and actuator assembly package assembly of claim 12 wherein the first protrusion of the first actuator member has a first inclined surface and the outer container has a straight cylindrical outer surface, and the first blocking member has a first angled surface and a first primary linear surface, wherein the first inclined surface of the first protrusion confronts and engages the first angled surface of the first blocking member and the straight cylindrical surface of the outer container confronts and engages the first primary linear surface of the first blocking member.

14. The dispenser and actuator assembly package assembly of claim 13 wherein the second protrusion of the second actuator member has a second inclined surface, and the second blocking member has an angled surface and a second primary linear surface, wherein the first inclined surface of the second protrusion confronts and engages the second angled surface of the second blocking member and the straight cylindrical surface of the outer container confronts and engages the second primary linear surface of the second blocking member.

* * * * *